US007973134B2

(12) United States Patent
Moritz et al.

(10) Patent No.: US 7,973,134 B2
(45) Date of Patent: Jul. 5, 2011

(54) REAGENTS FOR THE DETECTION OF PROTEIN PHOSPHORYLATION IN ANAPLASTIC LARGE CELL LYMPHOMA SIGNALING PATHWAYS

(75) Inventors: Albrecht Moritz, Salem, MA (US); Kimberly Lee, Seattle, WA (US); John Rush, Beverly, MA (US); Roberto Polakiewicz, Lexington, MA (US)

(73) Assignee: Cell Signaling Technology, Inc., Danvers, MA (US)

(*) Notice: Subject to any disclaimer, the term of this patent is extended or adjusted under 35 U.S.C. 154(b) by 904 days.

(21) Appl. No.: 11/503,096

(22) Filed: Aug. 11, 2006

(65) Prior Publication Data

US 2007/0072235 A1    Mar. 29, 2007

(51) Int. Cl.
*C07K 16/00* (2006.01)
*C07K 16/18* (2006.01)

(52) U.S. Cl. .................. 530/387.1; 530/387.9

(58) Field of Classification Search .................. None
See application file for complete search history.

(56) References Cited

U.S. PATENT DOCUMENTS

| | | |
|---|---|---|
| 3,940,475 A | 2/1976 | Gross et al. |
| 4,289,747 A | 9/1981 | Chu et al. |
| 4,349,893 A | 9/1982 | Wiegman et al. |
| 4,376,110 A | 3/1983 | David et al. |
| 4,474,893 A | 10/1984 | Reading et al. |
| 4,634,664 A | 1/1987 | Oestberg et al. |
| 4,634,666 A | 1/1987 | Engleman et al. |
| 4,659,678 A | 4/1987 | Forrest et al. |
| 4,676,980 A | 6/1987 | Segal et al. |
| 4,727,022 A | 2/1988 | Skold et al. |
| 4,816,397 A | 3/1989 | Boss et al. |
| 4,816,567 A | 3/1989 | Cabilly et al. |
| 4,946,778 A | 8/1990 | Ladner et al. |
| 5,004,692 A | 4/1991 | Tso et al. |
| 5,092,885 A | 3/1992 | Yamada et al. |
| 5,112,946 A | 5/1992 | Maione et al. |
| 5,192,744 A | 3/1993 | Bouck et al. |
| 5,202,352 A | 4/1993 | Okada et al. |
| 5,225,539 A | 7/1993 | Winter et al. |
| 5,260,203 A | 11/1993 | Ladner et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,675,063 A | 10/1997 | Knight et al. |
| 5,677,427 A | 10/1997 | Goldenberg et al. |
| 5,693,761 A | 12/1997 | Queen et al. |
| 5,693,762 A | 12/1997 | Queen et al. |
| 5,789,208 A | 8/1998 | Sharon et al. |
| 5,969,108 A | 10/1999 | McCafferty et al. |
| 6,103,889 A | 8/2000 | Whitlow et al. |
| 6,120,767 A | 9/2000 | Robinson et al. |
| 6,150,584 A | 11/2000 | Kucherlapati et al. |
| 6,180,370 B1 | 1/2001 | Queen et al. |
| 6,329,508 B1 | 12/2001 | Friden et al. |
| 6,331,415 B1 | 12/2001 | Cabilly et al. |
| 6,335,163 B1 | 1/2002 | Sharon et al. |
| 6,355,245 B1 | 3/2002 | Evans et al. |
| 6,395,718 B1 | 5/2002 | Slusher et al. |
| 6,407,213 B1 | 6/2002 | Carter et al. |
| 6,441,140 B1 | 8/2002 | Comb et al. |
| 6,462,075 B1 | 10/2002 | Bowen et al. |
| 6,465,431 B1 | 10/2002 | Thorn et al. |
| 6,475,784 B1 | 11/2002 | Papkoff et al. |
| 6,482,802 B1 | 11/2002 | Hu et al. |
| 6,482,810 B1 | 11/2002 | Brem et al. |
| 6,500,431 B1 | 12/2002 | Gill et al. |
| 6,500,924 B1 | 12/2002 | Brooks et al. |
| 6,518,298 B2 | 2/2003 | Green et al. |
| 6,521,439 B2 | 2/2003 | Folkman et al. |
| 6,525,019 B2 | 2/2003 | D'Amato et al. |
| 6,538,103 B1 | 3/2003 | Ji et al. |
| 6,544,758 B2 | 4/2003 | O'Reilly et al. |
| 6,544,947 B2 | 4/2003 | Holaday et al. |
| 6,548,477 B1 | 4/2003 | Olson et al. |
| 6,548,640 B1 | 4/2003 | Winter et al. |
| 6,559,126 B2 | 5/2003 | Tournaire et al. |
| 6,569,845 B1 | 5/2003 | Futamura et al. |
| 6,573,256 B2 | 6/2003 | Bishop et al. |

(Continued)

FOREIGN PATENT DOCUMENTS

EP          0120694          3/1984

(Continued)

OTHER PUBLICATIONS

PharMingen (Transduction Laboratories and PharMingen 1999 Cell Biology Sourcebook, 1999, pp. 242-245).*
Glenney et al (J of Immunological Methods, 1988, 109:277-285).*
Mammalian Gene Collection (MGC) Program Team "Generation and initial analysis of more than 15,000 full-length human and mouse cDNA sequences." Proc. Nat'l Acad. Sci. 99 (26): 16899-16903 (2002).
Haralambieva et al., "Tyrosine Phosphorylation in Human Lymphomas." The Histochemical Journal 34: 545-552 (2002).

(Continued)

*Primary Examiner* — Laura B Goddard
(74) *Attorney, Agent, or Firm* — Nancy Chiu Wilker

(57) ABSTRACT

The invention discloses 211 novel phosphorylation sites identified in signal transduction proteins and pathways underlying Anaplastic Large Cell Lymphoma (ALCL) involving the ALK-NPM translocation/fusion, and provides phosphorylation-site specific antibodies and heavy-isotope labeled peptides (AQUA peptides) for the selective detection and quantification of these phosphorylated sites/proteins, as well as methods of using the reagents for such purpose. Among the phosphorylation sites identified are sites occurring in the following protein types: Protein Kinases (including Receptor Tyrosine Kinases), Adaptor/Scaffold Proteins, Cellular Metabolism or Miscellaneous Enzymes, Oxidoreductases, Transcription Factors, Cytoskeletal Proteins, Translation Initiation Complexes, RNA Binding Proteins, Proteases, Acetyltransferases, G protein regulators/GTPases, Helicases, Apoptosis/Cell Cycle Regulation proteins, and Hydrolases.

3 Claims, 10 Drawing Sheets
(4 of 10 Drawing Sheet(s) Filed in Color)

U.S. PATENT DOCUMENTS

| | | | |
|---|---|---|---|
| 6,783,961 | B1 | 8/2004 | Edwards et al. |
| 6,867,007 | B2 | 3/2005 | Kauvar et al. |
| 6,884,869 | B2 | 4/2005 | Senter et al. |
| 6,979,557 | B2 | 12/2005 | Isogai et al. |
| 7,060,268 | B2 | 6/2006 | Andya et al. |
| 7,109,000 | B2 | 9/2006 | Edinger et al. |
| 7,198,896 | B2 | 4/2007 | Rush et al. |
| 7,300,753 | B2 | 11/2007 | Rush et al. |

FOREIGN PATENT DOCUMENTS

| | | |
|---|---|---|
| EP | 0239400 | 9/1987 |
| EP | 0404097 | 12/1990 |
| EP | 1184665 | 3/2002 |
| WO | WO 84/03508 | 9/1984 |
| WO | WO 85/03508 | 8/1985 |
| WO | WO 86/01533 | 3/1986 |
| WO | WO 91/10741 | 7/1991 |
| WO | WO 91/17271 | 11/1991 |
| WO | WO 92/01047 | 1/1992 |
| WO | WO 93/11161 | 6/1993 |
| WO | WO 93/12227 | 6/1993 |
| WO | WO 95/20401 | 8/1995 |
| WO | WO 96/27011 | 6/1996 |
| WO | WO 02/00729 | 3/2002 |
| WO | WO 03/016861 | 2/2003 |
| WO | WO 03/089474 | 10/2003 |
| WO | WO 03/106644 | 12/2003 |
| WO | WO 2004/009618 | 1/2004 |
| WO | WO 2004/039963 | 5/2004 |
| WO | WO 2004/066957 | 8/2004 |
| WO | WO 2004/091658 | 10/2004 |
| WO | WO 2005/056825 | 6/2005 |
| WO | WO 2005/083444 | 9/2005 |

OTHER PUBLICATIONS

Zamo et al., "Anaplastic lymphoma kinase (ALK) activates Stat3 and protects hematopoietic cells from cell death." Oncogene (2002) 21: 1038-1047.

Bai et al., "Nucleophosmin-Anaplastic Lymphoma Kinase of Large-Cell Anaplastic Lymphona is a Constitutively Active Tyrosine Kinase that Utilizes Phospholipase C-g to Mediate its Mitogenicity," Molecular and Cellular Biology 18(12): 6951-6961 (1998).

Fujimoto et al., "Characterization of the transforming activity of o80, a hyperphosphorylated protein in a Ki-1 lymphoma cell line with chromosomal translocation t(2;5);" Proc. Nat'l Acad. Sci. 93: 4181-4186 (1996).

Watanabe et al, "Four Tyrosine Residues in Phospholipase C-gamma 2, Identified as Btk-dependent Phosphorylation Sites, Are Required for B Cell Antigen Receptor-coupled Calcium Signaling," J. Biol. Chem. 276: 38595-38601 (2001).

Law et al., "Phospholipase C-gammal interacts with conserved phosphotyrosyl residues in the linker region of Syk and is a substrate for Syk", Mol. Cell. Biol. 16(4): 1305-1315 (Apr. 1996).

White, M.F. "The IRS-signalling system: A network of docking proteins that mediate insulin action," Molecular and Cellular Biochemistry 182: 3-11 (1998).

Van der Greer et al., "The SHC adaptor protein is highly phosphorylated at conserved, twin tyrosine residues (Y239/Y240) tht mediate protein-protein interactions," Current Biology 6(11): 1435-1444 (1996).

U.S. Appl. No. 10/408,486, filed Apr. 2003, Crosby et al.
U.S. Appl. No. 10/781,047, filed Feb. 17, 2004, Gygi et al.
U.S. Appl. No. 10/634,581, filed Aug. 2003, Johnson et al.
U.S. Appl. No. 10/821,234, filed Apr. 2004, Labat et al.
U.S. Appl. No. 11/077,717, filed Mar. 2005, Lam et al.
U.S. Appl. No. 11/089,368, filed Mar. 25, 2005, Ledbetter et al.
U.S. Appl. No. 11/049,630, filed Feb. 2, 2005, McKinsey et al.

Abu-Duhier et al., "Identification of novel FLT-3 Asp835 mutations in adult acute myeloid leukemia." Br. J. Haematol. 113: 983-988 (2001).

Hardy, et al., "Clinical and Molecular Genetic Analysis of 19 Wolfram Syndrome Kindreds Demonstrating a Wide Spectrum of Mutations in WFS1", Am. J. Hum. Genet. 65:1279-1290 (1999).

Dessein, et al., "Severe Hepatic Fibrosis in Schistoma mansoni Infection Is Controlled by a Major Locus That Is Closely Linked to the Interferon-y Receptor Gene", Am. J. Hum. Genet. 65:709-721, (1999).

Di Barletta, et al., "Different Mutations in the LMNA Gene Cause Autosomal Dominant and Autosomal Recessive Emery-Dreifuss Muscular Dystrophy", Am. J. Hum. Genet. 66:1407-1412 (2000).

Ebrahimi, et al., "Murine Gammaherpesvirus-68 Infection Causes Multi-Organ Fibrosis and Alters Leukocyte Trafficking in Interferon-y Receptor Knockout Mice", American Journal of Pathology, vol. 158, No. 6 Jun. 2001.

Jemal, et al., "Cancer Statistics 2005", CA: A Cancer Journal for Clinicians, Aug. 26, 2008.

Pollard, et al., "Using Single-Gene Deletions to Identify Checkpoints in the Progression of Systemic Autoimmunity", Annals of the New York Academy of Sciences, Apr. 2003; 987( ): 236-9.

Jaskiewicz, et al., "Expression of p53 Tumor Suppressor Gene, Oncoprotein c-erbB-2, Cellular Proliferation and Differentiation n Malignant and Benign Pancreatic Lesions", Anticancer Research 14: 1919-1922 (1994).

Agarwal, et al., "Inositol Hexaphosphate Inhibits Constitutive Activation of NF-xB in Androgen-independent Human Prostrate Carcinoma DU145 Cells", Anticancer Research 23: 3855-3862 (2003).

Arias-Romero, et al., "A tale of two Paks", Biol. Cell (2008) 100, 97-108.

Bache, et al., "Phosphorylation of Hrs downstream of the epidermal growth factor receptor", Eur. J. Biochem 269, 3881-3881 (2002).

Belsches, et al., "Role of c-Src Tyrosine Kinase in EEGF-Induced Mitogenesis." Frontiers in Bioscience 2,d501-518, Oct. 15, 1997.

G-Amlak, et al., "Reguation of myeloma cell growth through Akt/Gsk3/forkhead signaling pathway", Biochemical and Biophysical Research Sommunications 297 (2002) 760-764.

Radaeva, et al., "Interferon-y inhibits interferon-a signalling in hepatic cells: evidence for the involvement of STAT1 induction and hyperexpression of STAT1 in chronic hepatitis C", Biochem J. (2004) 379, 199-208.

Awasthi, et al., "Novel Function of Human RLIP76: ATP-Dependent Transport of Glutathione Conjugates and Doxorubicin", Biochemistry 200, 39, 9327-9334.

Jagani, et al., "Foxe tumor suppressors and BCR-ABL-induced leukemia: A matter of evasion of apoptosis", Biochimica et Biophysica Acta 1785 (2008) 63-84.

Hashimoto, et al., "The Breakpoint Cluster Region Gene on Chromosome 22q11 Is Associated with Bipolar Disorder", Biol Psychiatry, May 15, 2005;57(10):1097-102.

Bird, et al., "Single-Chain Antigen-Binding Proteins", Science, vol. 242: 423-426, Oct. 21, 1988.

Blood, et al., "Tumor interactions with the vasculature: angiogenesis and tumor metastasis." Biochemica et Biophysica Acta, 1032 (1990) 89-118.

Awasthi, et al., "RLIP76, a non-ABC transporter, and drug resistance in epilepsy", BMC Neuroscience, 2005 6.61.

Boder, et al., "Yeast surface display for screening combinatorial polypeptide libraries", Nature Biotechnology, vol. 15, 553-557, Jun. 1997.

Bordin, et al., "Band 3 is an anchor protein and a target for SHP-2 tyrosine phosphatase in human erythrocytes", Blood, vol. 100, No. 1, 276-282, Jul. 1, 2002.

Brand, et al., "Fluorescence Probes for STRUCTURE1", Annu.Rev. Biochem. 1972.41:843-868.

Brennan, et al., "Preparation of Bispecific Antibodies by Chemical Recombination of Monoclonal Immunoglobulin G1 Fragments", Science, vol. 229:81-83, Jul. 5, 1985.

Byers et al., "Rationale for clinical use of immunotoxins in cancer and autoimmune disease" Seminars in Cell Biology 2:59-70 (1991).

Calalb, et al.,"Tyrosine Phosphorylation of Focal Adhesion Kinase at Sites in the Catalytic Domain Regulates Kinase Activity: a Role for Src Family Kinases", Molecular and Cellular Biology, vol. 15, No. 2 Feb. 1995, p. 954-963.

Grand, et al., "p53-Binding Protein 1 Is Fused to the Platelet-Derived Growth Factor Receptor B in a Patient with a t(5;15)(q33;q22) and a Imagine-Responsive Eosinophilic Myeloproliferative Disorder", Cancer Research 64, 7216-7219, Oct. 15, 2004.

Carr, et al., "The Need for Guidelines in Publication of Peptide and Protein Identification Data", Molecular & Cellular Proteomics 3.6, 531-533, 2004.

Cell Signaling Technology, "Phospho-PLCgammal (Tyr783) Antibody" 2007 Cell Signaling Technology, Inc., Jul. 2000, 1-3.

Accili et al., "FoxOs at the Crossroads of Cellular Metabolism, Differentiation, and Transformation" Cell, vol. 117, 421-426, May 14, 2004, Copyright 2004 by Cell Press.

Chow et al., "Measurement of MAP Kinase Activation by Flow Cytometry Using Phospho-Specific Antibodies to MEK and ERK: Potential for Pharmacodynamic Monitoring of Signal Transduction Inhibitors", Cytometry (Communications in Clinical Cytometry) 46: 72-78 (2001).

Coia, et al., "Panning and selection of proteins using ribosome display", Journal of Immunological Methods 254 (2001) 191-197.

Crook, et al.,"Repressed by a NuRD", Nature Cel Biology vol. 8 No. 3 Mar. 2006, 212-214.

Cross, et al.,"Serine/Threonine Protein Kinases and Apoptosis", Experimental Cell Research 256, 34-41, 2000.

Czernik, et al.,"Production of Phosphorylation State-Specific Antibodies", Methods in Enzymology, vol. 201, 1991, 264-283.

Daley, et al, "Induction of Chronic Myelogenous Leukemia in Mice by the P210bcr/abl Gene of the Philadelphia Chromosome" Science, vol. 247, 1990, 824-830.

Denslow, et al., "The human Mi-2/NuRD complex and gene regulation", Oncogene (2007) 26, 5433-5438.

Dorahy, et al., "Capture by chemical crosslinkers provides evidence that integrin allbfl3 forms complex with protein tyrosine kinases in intact platelets" Biochem J. (1995) 389, 481-490 (Printed in Great Britain).

Druker, et al., "Imatinib as a Paradigm of Targeted Therapies", Adv. Cancer Res. 2004, 91 ( ): 1-30.

Edgar, et al., "Flotillin-1: gene structure c DNA cloning from human lung and the identification of alternative polyadenylation signals", The international Journal of Biochemisty & Cell Biology 33 (2001) 53-64.

Blanton, et al., "Schistosomal hepatic fibrosis and the interferon gamma receptor: a linkage analysis using single-nucleotide polymorphic markers", European Journal of Human Genetics (2005) 13, 660-668.

Song, et at., "Lamin A/C mutations associated with familial and sporadic cases of dilated cardiomyopathy in Koreans", Experimental and Molecular Medicine, vol. 39, No. 1, 114-120, Feb. 2007.

Fanger, et al., "Bispecific antibodies and targeted cellular cytotoxicity", Immunol Today, Feb. 1991;12(2):51-4.

Vadlamudi, et al., "Heregulin and HER2 signaling selectively activates c-Src phosphorylation at tyrosine 215" FEBS Letters 543 (2003) 76-80.

Yang, et al "ERK promotes tumorigenesis by inhibiting FOXO3a via MDM2-mediated degradation." Nat Cell Biol. Feb. 2008;10(2):138-48.

Fujita N. et al., "MTA3 and the Mi-2/NuRD complex regulate cell fate during B lymphocyte differentiation." (2004)CELL 119:75-86.

Fujita N. et al., "MTA3; a Mi-2/NuRD Complex Subunit, Regulates an Invasive Growth Pathway in Breast Cancer." (2003) Cell 113:207-19.

Meinhart, et al "A Structural Perspective of CTD Function." Genes Dev. Jun. 2005 15;19(12):1401-15.

Gerber et al., "Absolute quantification of proteins and phosphoproteins from cell lysates by tandem MS.", PNAS, Jun. 2003.

Graves et al. "protein phosphorylation and signal transduction." Pharmacol. Ther. 82: 111-21 (1999).

Griffiths et al. "Human anti-self antibodies with high specificity from phage display libraries." EMBO L., 12:725-734 (1993).

Griffiths et al. "Isolation of high affinity human antibodies directly from large synthetic repertoires." EMBO J. 13:3245-3260 (1994).

Gruber et al. "Efficient tumor cell lysis mediated by a bispecific single chain antibody expressed in *Escherichia coli*." J. Immunol., 152:5368 (1994).

Gu et al. "Phosphotyrosine profiling identifies the KG-1 cell line as a model for the study of FGFR1 fusions in acute myeloid leukemia." Blood First Edition Paper and supplemental table 1, pre-published online Aug. 31, 2006; DOI 10.1182/blood-2006-06-026666, see p. 3 of Table 1, litening under "Hsp70".

Hanes J. et al. "Picomolar affinity antibodies from a fully synthetic naive library selected and evolved by ribosome display." Nat. Biotechnol. 18(12):1287-92(2000).

Heessen S., Fornerod M., "The inner nuclear envelope as a transcription factor resting place." EMBO Rep. 8:914-9 (2007).

Kakumu, et al "Interferon-gamma receptors on T cells in patients with chronic liver disease." Hepatogastroenterology Aug.;35(4):158-61(1988).

Hollinger et al., "Diabodies: small bivalent and bispecific antibody fragments." Proc. Natl. Acaf. Sci. USA, 90:6444-8(1993).

Burwinkel et al "Phosphorylase-kinase-deficient liver glycogenosis with an unusual biochemical phenotype in blood cells associated with a missense mutation in the beta subunit gene (PHKB)." Hum Genet Dec.;101(2):170-4 (1997).

Blume-Jensen et al., "Oncogenic kinase signalling." Nature 411: 355-65 (2001).

Huse w. "Generation of a Large Combinatorial Library of the Immunoglobulin Repertoire in Phage Lambda." Science 246:1275-1281 (1989).

Ingber et al., "Inhibition of Angiogenesis Through Modulation of Collagen Metabolism." Lab. Invest., 59:44-51 (1988).

Htun Van Der Horst, et al "Tyrosine phosphorylation of PYK2 mediates heregulin-induced glioma invasion: novel heregulin/HER3-stimulated signaling pathway in glioma." Int. J Cancer Feb. 20;113(5):689-98 (2005).

Irby et al., "Role of Src expression and activation in human cancer." Oncogene 16: 5636-642 (2000).

Jullien-Flores "Bridging Ral GTPase to Rho pathways" RLIP76, a Ral effector with CDC42/Rac GTPase-activating protein activity. J Cell Chem Sep. 22, 1995;270(38):22473-7.

Hu, et al "HSF-1 interacts with Ral-binding protein 1 in a stress-responsive, multiprotein complex with HSP90 in vivo" J Cell Chem. May 9, 2003;278(19):17299-306.

Birkenkamp, et al "FOXO3a induces differentiation of Bcr-Abl-transformed cells through transcriptional down-regulation of Id1." J Biol. Chem. Jan. 26, 2007;282(4):2211-20.

Goldfinger, et al "RLIP76 (RalBP1) is an R-Ras effector that mediates adhesion-dependent Rac activation and cell migration." J Cell Biol. Sep. 11, 2006;174(6):877-88.

Dorman, et al "Viral infections in interferon-gamma receptor deficiency." The Journal of Pediatrics Nov.;135(5):640-3(2006).

Kim H. et al., "Epidermal growth factor-dependent association of phosphatidylinositol 3-kinase with the erbB3 gene product" J Biol. Chem., 269(40)24747-24755(1994).

Kohler, et al "Derivation of specific antibody-producing tissue culture and tumor lines by cell fusion." Eur. J. Immunol. 6:511 (1976).

Kostelny et al., "Formation of a Bispecific Antibody By The Use Of Leucine Zippers." J. Immunol., 148(5):1547-1557 (1992).

Dorman, et al "Clinical features of dominant and recessive interferon gamma receptor 1 deficiencies." Lancet Dec. 11-17, 2004;364(9451):2113-21.

Merrifield "Solid Phase Peptide Synthesis I, The Synthesis of a Tetrapeptide." J. Am. Chem. Soc. 85:21-49 (1962).

Milstein and Cuello "Hybrid hybridomas and their use in immunohistochemistry." Nature, 305:537-540(1983).

Radziwill, et al "The Bcr kinase downregulates Ras signaling by phosphorylating AF-6 and binding to its PDZ domain." Mol. Cell Biol. Jul. 2003;23(13):4663-42.

Morrison et al., "Chimeric human antibody molecules: Mouse antigen-binding domains with human constant region domains." Proc. Nat'l Acad. Sci. 81: 6851(1984).

Moses et al., "Identification of an Inhibitor of Neovascularization from cartilage." Science, 248:1408-1410 (1990).

Mullinax et al., "Identification of human antibody fragment clones specific for tetanus toxoid in a bacteriophage gamma immunoexpression library." Proc. Nat'l Acad. Sci. 87: 8095(1990).

Nakamura, Y., "Codon usage tabulated from international DNA sequence databases: status for the year 2000." Nucleic Acids Res. Jan. 1;28:292 (2000).

Nardi, et al., "Mechanisms and implications of imatinib resistance mutations in BCR-ABL." Curr. Opin. Hematol. 11:35-43(2003).

Shackleton, et al "LMNA, encoding lamin A/C, is mutated in partial lipodystrophy." Nat. Genet. Feb. 2000;24(2):153-6.

Shankaran, et al "IFN gamma and lymphocytes prevent primary tumour development and shape tumour immunogenicity." Nature Apr. 26, 2001; 410(6832): 1107-11.

Feske, et al "A mutation in Orai1 causes immune deficiency by abrogating CRAC channel function." Nature May 11, 2006;441 (7090):179-85.

Neuberger, et al "Recombinant antibodies possessing novel effector functions." Nature. Dec. 13-19, 1984; 312(5995):604-8.

Newman et al., "Primatization of Recombinant Antibodies for Immunotherapy of human Diseases: A Macaque/Human Chimeric Antibody Against Human CD4." BioTechnology, 10: 1455-1460(1992).

Nissim et al., "Antibody fragments from a 'single pot' phage display library as immunochemical reagents." EMBO J. Feb. 1, 1994;13(3):692-8.

Ostberg, et al.,"Human x (Mouse x Human) Hybridomas Stably Producing Human Antibodies", Hybridoma, vol. 2, No. 4, 1983, 361-367.

Olayioye, et al.,"The ErbB signaling network: receptor heterodimerization in development and cancer", The EMBO Journal vol. 19 No. 13 pp. 3159-3167, 2000.

Liu, et al., "Induction of prosurvival molecules by apoptotic stimuli: involvement of FOX03a and ROS", Oncogene (2005) 24, 2020-2031.

Order, et al., "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985).

Paweletz, et al., "Reverse phase protein microarrays which capture disease progression show activation of pro-survival pathways at the cancer invasion front", Oncogene (2001) 20, 1981-1989.

Pluckthun et al., "Antibodies from *Escherichia coli*" The Pharmacology of Monoclonal Antibodies, vol. 113, Rosenburg and Moore, eds. (Springer-Verlag: New York, 1994), pp. 269-315.

Prigent, et al., "Identification of c-erbB-3 binding sites for phosphatidylinositol 3'-kinase and SHC using an EGF receptor/c-erbB-3 chimera" The EMBO Journal vol. 13 No. 12 pp. 2831-2841, 1994.

Cao, Kan "A lamin A protein isoform over expressed in Hutchinson-Gilford progeria syndrome interferes with mitosis in progeria and normal cells" Proc. Natl. Acad. Sci U S A. Mar. 20, 2007;104(12):4949-54.

Dechat, H. "Alterations in mitosis and cell cycle progression caused by a mutant lamin A known to accelerate human aging." Proc. Natl. Acad. Sci U S A. Mar. 20, 2007;104(12):4955-60.

Hanes, J. "In vitro selection and evolution of functional proteins by using ribosome display" Proc. Natl. Acad. Sci. U. S. A. 94(10):4937-42 (1997).

Hanes, J. "Ribosome display efficiently selects and evolves high-affinity antibodies in vitro from immune libraries." Proc. Natl. Acad. Sci. U. S. A. 95(24):14130-5 (1998).

Masui, et al., "A possible association between missense polymorphism of the breakpoint cluser region gene and lithium prophylaxis in bipolar disorder", Progress in Neuro-Psychopharmacogy & Biological Psychiatry 32 (2008) 204-208.

Reddy, et al., "Transcriptional repression mediated by repositioning of genes to the nuclear lamina" Vole 452 Mar. 13, 2008 doi:10.1038/Nature 06727.

Rosnet, et al.,"Hematopoietic Receptors of Class III Receptor-type Tyrosine Kinases", Critical Reviews in Ontogenesis, 4 (6): 595-613 (1993).

Schaller, et al.,"Autophosphorylation of the Focal Adhesion Kinase, pp125FAK Directs SH2-Dependent Binding of pp6Osrc", Molecular and Cellular Biology, Mar. 1994, p. 1680-1688.

Schindler, et al., "Structural Mechanism for STI-571 Inhibition of Abelson Tyrosine Kinase", Science 289: 1938-1942 (2000).

Schreiber, et al., "Target-Oriented and Diversity-Oriented Organic Synthesis in Drug Discovery", Science 287, 1964-1969 (2000).

Castrillon, et al., "Suppression of Ovarian Follicle Activation in Mice by the Transcription Factor Foxo3a", Science 301, 215-218 2003.

Shalaby, et al., "Development of Humanized Bispecitic Antibodies Reactive with Cytotoxic Lymphocytes and Tumor Cells Overexpressing the HER2 Protooncogene", J. Exp. Med. vol. 175 Jan. 1992 217-225.

Shen, et al.,"Evidence for SH3 domain directed binding and phosphorylation of Sam68 by Src", Oncogene 18 4647-4653 (1999).

Spira, et al.,"The identification of monoclonal class switch variants by Sib Selection and an ELISA Assay", Journal of Immunological Methods, 74 (1984) 307-315.

Steplewski, et al., "Isolation and characterization of anti-monosialoganglioside monoclonal antibody 19-9 class-switch variants", Proc. Nat'l. Acad. Sci., USA vol. 82 pp. 8653-8657, Dec. 1985.

Stryer, et al., "Fluorescence Spectroscopy of Proteins" Science, vol. 162 1968 526-533.

Suresh, et al., "Bispecific monoclonal antibodies from hybrid hybridomas" Methods in Enzymology, vol. 121 1986 210-228.

Tutt, et al., "Trispecific F(ab'), Derivatives That Use Cooperative Signaling Via the TCR/CD3 Complex and CD2 to Activate and Redirect Resting Cytotoxic T Cells'" The Jouhnal of Immunology 147(1):60-9 (1991).

Upstate, et al., "Antibodies for Phosphorylation & Beyond", Internet Article, Jun. 2004, 1-16.

Vadlamudi, et al., "Heregulin and HER2 signaling selectively activates c-Src phosphorylation at tyrosine 215" Febs Letters 543. 2003, 76-80.

Vijapurkar, et al.,"Roles of mitogen-activated protein kinase and phosphoinositide 3'kinase in ErbB2/ErbB3 coreceptor-mediated heregulin signaling" Experimental Cell Research 284, 2003, 291-302.

Walker. et al., "Interaction of Human IgG Chimeric Antibodies With the Human FcRII Receptors: Requirements for Antibody-Mediated Host Cell-Target Cell Interaction" Molecular Immunology , vol. 26 No. 4, pp. 403-411 1989.

Wetzel, et al., Evaluation of CML model cell lines ad imatinib mesylate response: Determinants of signaling profiles. Journal of Immunological Methods, 2005.

Yamamoto, et al., "Activating mutation of D835 within the activation loop of FLT3 in human hematologic malignancies" Blood, Apr. 15, 2001 vol. 97, No. 8 2434-2439.

Yang, et al., "Lysine acetylation and the bromodomian: a new partnership for signaling", BioEssays, 2004, vol. 26, Iss 10, 1076-1087.

Yeatman, et at, "A Renaissance for SRC", Nature Reviews 4: 2004, 470-480.

Yeung, et al., "Quantitative Screening of Yeast Surface-Displayed Polypeptide Libraries by Magnetic Bead Capture" Biotechnol. Prog. 2002, 18(2):212-20.

Yokota, et al., "Internal tandem duplication of the FLT3 gene is preferentially seen in acute myeloid leukemia and myelodysplastic syndrome among various hematological malignancies. A study on a large series of patients and cell lines", Leukemia 1997 11: 1605-1609.

Zapata, et al., "Engineering linear F (ab')2 fragments for efficient production in *Escherichia coli* and enhanced antiproliferative activity" Protein Engineering vol. 8 No. 10 pp. 1057-1062, 1995.

Zhang, et al., "Phosphoprotein Analysis Using Antibodies Broadly Reactive against Phosphorylated Motifs" Journal of Biological Chemistry, 2002, vol. 227, pp. 39379-39387.

Khoury, et al "Differential Expression and Clinical Significance of Tyrosine-phosphorylated STAT3 in ALK+ and ALK− Anaplastic Large Cell Lymphoma" Clinical Cancer Research 9: 3692-3699 (2003).

Zhang , et al "Multilevel Dysregulation of STAT3 Activation in Anaplastic Lymphoma Kinas-Positive T/Null-Cell Lymphoma" The Journal of Immunology 168: 466-474 (2002).

Salomon, et al "Profiling of tyrosine phosphorylation pathways in human cells using mass spectrometry" Proc. Natl. Acad. Sci. 100(2): 443-448 (2003).

Kentrup, et al "Dyrk, a Dual Specificity Protein Kinase with Unique Structural Features Whose Activity is Dependent on Tyrosine Residues between Subdomains VII and VIII" The Journal of Biological Chemistry 271(7): 3488-3495 (1996).

Guimera, et al "Human Minibrain Homologue (MNBH/DYRK1): Characterization, Alternative Splicing, Differential Tissue Expression, and Overexpression in Down Syndrome" Genomics 57: 407-418 (1999).

Haralambieva, et al "Tyrosine phosphorylation in human lymphomas" The Histochemical Journal 34: 545-552 (2002).

Rush, et al "Immunoaffinity profiling of tyrosine phosphorylation in cancer cells" Nature Biotechnology 23(1): 94-101 (2005).

Chiarle, et al "NPM-ALK transgenic mice spontaneously develop T-cell lymphomas and plasma cell tumors" Blood 101(5): 1919-1927 (2003).

Ouyang, et al "Identification and Characterization of a Nuclear Interacting Partner of Anaplastic Lymphoma Kinase (NIPA)" The Journal of Biological Chemistry 278(32): 30028-30036 (2003).

* cited by examiner

FIGURE 2

| | A | B | C | D | F | G | H | I |
|---|---|---|---|---|---|---|---|---|
| 1 | Protein Name (short) | Protein Name (full) | Accession Number | Protein Type | Phospho-Residue | Phosphorylation Site Sequence | SEQ ID NO: | Cell Line |
| 2 | ELP3 | elongation protein 3 homolog | Q9BVF7 | Acetyltransferase | Y202 | GHTSNNIyEAVKYSE | SEQ ID NO: 1 | Both |
| 3 | GCN5-like 2 | GCN5 | Q92830 | Acetyltransferase | Y734 | LKDPDQLyTTLKNLL | SEQ ID NO: 2 | SU-DHL1 |
| 4 | MAK3P | hypothet. protein FLJ13194 | Q9GZZ1 | Acetyltransferase | Y110 | DGTFDNIyLHVQISN | SEQ ID NO: 3 | SU-DHL1 |
| 5 | transglutaminase 2 | transglutaminase | P21980 | Acetyltransferase | Y369 | QEKSEGTyCCGPVPV | SEQ ID NO: 4 | SU-DHL1 |
| 6 | coronin 1C | coronin, actin-bind. pro. 1C | Q9ULV4 | Actin binding protein | Y301 | EITDESPyVHYLNTF | SEQ ID NO: 5 | SU-DHL1 |
| 7 | GMF-beta | glia maturation factor, beta | P17774 | Actin binding protein | Y83 | HDDGRVSyPLCFIFS | SEQ ID NO: 6 | Karpas 299 |
| 8 | L-plastin | plastin | P13796 | Actin binding protein | Y124 | SYSEEEKyAFVNWIN | SEQ ID NO: 7 | SU-DHL1 |
| 9 | WDR1 | WD repeat domain 1 | O75083 | Actin binding protein | Y238 | KAHDGGIyAISWSPD | SEQ ID NO: 8 | Both |
| 10 | profilin 1 | profilin 1 | P07737 | Actin binding protein; Cytoskeletal protein | Y128 | GLINKKCyEMASHLR | SEQ ID NO: 9 | Both |
| 11 | CD2AP | CD2-associated protein | Q9Y5K6 | Adaptor/scaffold | Y88 | LVQRISTyGLPAGGI | SEQ ID NO: 10 | Karpas 299 |
| 12 | CGRP-RCP | calcitonin rel. pep. comp. | O75575 | Adaptor/scaffold | Y47 | QNLNTTTyETLKYIS | SEQ ID NO: 11 | SU-DHL1 |
| 13 | Crk | Crk | P46108 | Adaptor/scaffold | Y239 | NLQNGPIyARVIQKR | SEQ ID NO: 12 | SU-DHL1 |
| 14 | Hrs | HGF reg. tyr. kinase subs. | O14964 | Adaptor/scaffold | Y216 | VRVCEPCyEQLNRKA | SEQ ID NO: 13 | Both |
| 15 | Intersectin 2 | intersectin 2 isoform 1 | Q9NZM3 | Adaptor/scaffold | Y858 | QPASVTDyQNVSFSN | SEQ ID NO: 14 | SU-DHL1 |
| 16 | Intersectin 2 | intersectin 2 isoform 1 | Q9NZM3 | Adaptor/scaffold | Y967 | REEPEALyAAVNKKP | SEQ ID NO: 15 | SU-DHL1 |
| 17 | IRS-1 | insulin receptor substrate 1 | P35568 | Adaptor/scaffold | Y46 | GGPARLEyYENEKKW | SEQ ID NO: 16 | SU-DHL1 |
| 18 | IRS-1 | insulin receptor substrate 1 | P35568 | Adaptor/scaffold | Y662 | QRVDPNGyMMMSPSG | SEQ ID NO: 17 | SU-DHL1 |
| 19 | RACK1 | G protein, beta poly. 2-like 1 | P25388 | Adaptor/scaffold | Y228 | LNEGKHLyTLDGGDI | SEQ ID NO: 18 | SU-DHL1 |
| 20 | TSAd | T lymphocyte adaptor | Q9NP31 | Adaptor/scaffold | Y216 | SQDPNPQySPIIKQG | SEQ ID NO: 19 | Karpas 299 |
| 21 | TSAd | T lymphocyte adaptor | Q9NP31 | Adaptor/scaffold | Y305 | GEAPSNIyVEVEDEG | SEQ ID NO: 20 | Karpas 299 |
| 22 | TSAd | T lymphocyte adaptor | Q9NP31 | Adaptor/scaffold | Y39 | RSCQNLGyTAASPQA | SEQ ID NO: 21 | Karpas 299 |
| 23 | VAM-1 | MAGUK protein p55T | Q9NZW5 | Adaptor/scaffold | Y500 | SARIQRAyNHYFDLI | SEQ ID NO: 22 | SU-DHL1 |
| 24 | laminin receptor 1 | laminin receptor 1 | P08865 | Adhesion; Receptor, misc. | Y139 | QPLTEASyVNLPTIA | SEQ ID NO: 23 | Both |
| 25 | FAF1 | FAS-associated fac. 1 iso. a | Q9UNN5 | Apoptosis | Y225 | QEVKRNVyDLTSIPV | SEQ ID NO: 24 | Both |
| 26 | programmed cell death 4 | programmed cell death 4 | Q8TAR5 | Apoptosis | Y152 | DDQENCVyETVVLPL | SEQ ID NO: 25 | SU-DHL1 |
| 27 | Casp8 | caspase 8 isoform A | Q14790 | Apoptosis; Protease (non-proteasomal) | Y334 | DGQEAPIyELTSQFT | SEQ ID NO: 26 | Karpas 299 |
| 28 | nucleolysin, TIA-1-related | T-cluster binding protein | Q01085 | Apoptosis; RNA binding protein | Y50 | EHTSNDPyCFVEFYE | SEQ ID NO: 27 | SU-DHL1 |
| 29 | annexin A1 | annexin I | P04083 | Calcium-binding protein | Y206 | DSDARALyEAGERRK | SEQ ID NO: 28 | SU-DHL1 |
| 30 | MKLP1 | mitotic kinesin-like 1 | Q02241 | Calcium-binding protein; Motor protein | Y29 | LKDPVGVyCRVRPLG | SEQ ID NO: 29 | SU-DHL1 |
| 31 | CUL-3 | cullin 3 | Q13618 | Cell cycle regulation | Y58 | GLSFEELyRNAYTMV | SEQ ID NO: 30 | Karpas 299 |
| 32 | VGCNL1 | voltage gated channel like 1 | Q8IZF0 | Channel, calcium | Y497 | PALEDFVyKIFGPGK | SEQ ID NO: 31 | SU-DHL1 |
| 33 | VDAC-1 | voltage dep. anion channel | P21796 | Channel, misc. | Y194 | TEFGGSIyQKVNKKL | SEQ ID NO: 32 | SU-DHL1 |
| 34 | VDAC-3 | voltage-dep. anion channel 3 | Q9Y277 | Channel, misc. | Y195 | TEFGGSIyQKVNEKI | SEQ ID NO: 33 | SU-DHL1 |
| 35 | HSP60 | heat shock 60kDa protein 1 | P10809 | Chaperone | Y227 | DRGYISPyFINTSKG | SEQ ID NO: 34 | SU-DHL1 |
| 36 | HSP70RY | heat shock 70kDa protein 4 | P34932 | Chaperone | Y336 | KLKKEDIyAVEIVGG | SEQ ID NO: 35 | SU-DHL1 |
| 37 | HSP70RY | heat shock 70kDa protein 4 | P34932 | Chaperone | Y89 | AEKSNLAyDIVQLPT | SEQ ID NO: 36 | Karpas 299 |
| 38 | HSP90-beta | HSP90 beta AND heat shock 90kD prot. 1, beta | P08238 | Chaperone | Y483 | KETQKSIyYITGESK | SEQ ID NO: 37 | SU-DHL1 |
| 39 | TCP-1-theta | chaperonin containing TCP1 | P50990 | Chaperone | Y505 | LDTYLGKyWAIKLAT | SEQ ID NO: 38 | SU-DHL1 |
| 40 | tetratricopeptide repeat protein 2 | tetratricopep. repeat dom. 2 | Q99615 | Chaperone | Y40 | DYNEAYNyYTKAIDM | SEQ ID NO: 39 | Both |
| 41 | prohibitin, D | B-cell associated protein | Q99623 | Chaperone; RNA binding protein | Y128 | YQRLGLDyEERVLPS | SEQ ID NO: 40 | SU-DHL1 |
| 42 | MIF | macrophage migr. inhib. fac. | P14174 | Cytokine | Y36 | ATGKPPQyIAVHVVP | SEQ ID NO: 41 | SU-DHL1 |
| 43 | PBEF | colony-enhancing fact. iso. a | P43490 | Cytokine | Y188 | GNLDGLEyKLHDFGY | SEQ ID NO: 42 | Both |
| 44 | actin, alpha 1 | alpha 1 actin precursor | P02568 | Cytoskeletal protein | Y220 | DIKEKLCyVALDFEN | SEQ ID NO: 43 | SU-DHL1 |
| 45 | actin, beta | beta actin | P02570 | Cytoskeletal protein | Y218 | DIKEKLCyVALDFEQ | SEQ ID NO: 44 | Both |
| 46 | actin, beta | beta actin | P02570 | Cytoskeletal protein | Y294 | VDIRKDLyANTVLSG | SEQ ID NO: 45 | Both |
| 47 | Arp3 | ARP3 homolog | P32391 | Cytoskeletal protein | Y231 | AKAVKERySYVCPDL | SEQ ID NO: 46 | SU-DHL1 |
| 48 | Bicd2 | coiled-coil protein BICD2 | Q8TD16 | Cytoskeletal protein | Y424 | DSHEDGDyYEVDING | SEQ ID NO: 47 | SU-DHL1 |
| 49 | cofilin 1 | cofilin 1 | P23528 | Cytoskeletal protein | Y140 | HELQANCyEEVKDRC | SEQ ID NO: 48 | Both |
| 50 | EMAP-4 | echin. microtub. assoc. like 4 | Q9HC35 | Cytoskeletal protein | Y226 | IINQEGEyIKMFMRG | SEQ ID NO: 49 | Both |
| 51 | similar to beta-actin | alpha 1 actin precursor | XP_301899 | Cytoskeletal protein | Y53 | GMGQKDSyVGNEAQS | SEQ ID NO: 50 | Both |
| 52 | stomatin-like protein 2 | stomatin (EPB72)-like 2 | Q9UJZ1 | Cytoskeletal protein | Y124 | YGVEDPEyAVTQLAQ | SEQ ID NO: 51 | SU-DHL1 |

FIGURE 2
(Continued)

| | Protein Name (short) | Protein Name (full) | Accession Number | Protein Type | Phospho-Residue | Phosphorylation Site Sequence | SEQ ID NO: | Cell Line |
|---|---|---|---|---|---|---|---|---|
| 53 | talin 1 | talin 1 | Q9Y490 | Cytoskeletal protein | Y70 | EAGKALDyYMLRNGD | SEQ ID NO: 52 | SU-DHL1 |
| 54 | tubulin, alpha-1 | tubulin, alpha 1 | P05209 | Cytoskeletal protein | Y272 | IHFPLATyAPVISAE | SEQ ID NO: 53 | Karpas 299 |
| 55 | tubulin, gamma complex component 2 | gamma-tubulin com. pro. 2 | Q9BSJ2 | Cytoskeletal protein | Y83 | RNLDPLVyLLSKLTE | SEQ ID NO: 54 | SU-DHL1 |
| 56 | VASP | vasodilator-stim. p-protein | P50552 | Cytoskeletal protein | Y38 | QAFSRVQIYHNPTAN | SEQ ID NO: 55 | Both |
| 57 | vimentin | vimentin | P08670 | Cytoskeletal protein | Y116 | LNDRFANyIDKVRFL | SEQ ID NO: 56 | SU-DHL1 |
| 58 | profilin 1 | profilin 1 | P07737 | Cytoskeletal protein; Actin binding protein | Y128 | GLINKKCyEMASHLR | SEQ ID NO: 57 | Both |
| 59 | H4 | histone H4 | P02304 | DNA binding protein | Y51 | KRISGLIyEETRGVL | SEQ ID NO: 58 | Both |
| 60 | RoXaN | Rotavirus 'X' assoc. protein | Q9UGR2 | DNA binding protein | Y664 | KVWLLQQySGMTHED | SEQ ID NO: 59 | Both |
| 61 | zinc finger, CCHC domain-containing 3 | CCHC domain containing 3 | Q9NUD5 | DNA binding protein | Y202 | GMDPSDIyAVIQIPG | SEQ ID NO: 60 | SU-DHL1 |
| 62 | hnRNP U | hnRNP U isoform b | Q00839 | DNA binding protein; RNA binding protein | Y472 | YFPIPEEyTFIQNVP | SEQ ID NO: 61 | Both |
| 63 | APE1 | APEX nuclease | P27695 | DNA repair | Y261 | HLYPNTPyAYTFWTY | SEQ ID NO: 62 | SU-DHL1 |
| 64 | aldolase A | aldolase A | P04075 | Enzyme, cellular metabolism | Y203 | HDLKRCQyVTEKVLA | SEQ ID NO: 63 | SU-DHL1 |
| 65 | enolase, alpha | enolase 1 | P06733 | Enzyme, cellular metabolism | Y286 | YKSFIKDyPVVSIED | SEQ ID NO: 64 | Both |
| 66 | enolase, alpha | enolase 1 | P06733 | Enzyme, cellular metabolism | Y43 | SGASTGIyEALELRD | SEQ ID NO: 65 | Both |
| 67 | enolase, neural | enolase 2 | P09104 | Enzyme, cellular metabolism | Y43 | SGASTGIyEALELRD | SEQ ID NO: 66 | SU-DHL1 |
| 68 | G6PD | G6PDH | P11413 | Enzyme, cellular metabolism | Y400 | VQPNEAVyTKMMTKK | SEQ ID NO: 67 | Both |
| 69 | GAPDH | G3PDH | P04406 | Enzyme, cellular metabolism | Y41 | DPFIDLNyMVYMFQY | SEQ ID NO: 68 | SU-DHL1 |
| 70 | GART | phosphoribosyl. synthetase | P22102 | Enzyme, cellular metabolism | Y348 | SKGYPGDyTKGVEIT | SEQ ID NO: 69 | SU-DHL1 |
| 71 | IMP dehydrogenase 2 | IMP dehydrogenase 2 | P12268 | Enzyme, cellular metabolism | Y400 | TTEAPGEyFFSDGIR | SEQ ID NO: 70 | SU-DHL1 |
| 72 | LDH-A | lactate dehydrogenase A | P00338 | Enzyme, cellular metabolism | Y238 | KQVVESAyEVIKLKG | SEQ ID NO: 71 | Both |
| 73 | LDH-B | lactate dehydrogenase B | P07195 | Enzyme, cellular metabolism | Y239 | KMVVESAyEVIKLKG | SEQ ID NO: 72 | Both |
| 74 | PFK-B | phosphofructokinase, liver | P17858 | Enzyme, cellular metabolism | Y633 | RNEKCHDyYTTEFLY | SEQ ID NO: 73 | SU-DHL1 |
| 75 | phosphoglycerate kinase 1 | phosphoglycerate kinase 1 | P00558 | Enzyme, cellular metabolism | Y195 | LMKKELNyFAKALES | SEQ ID NO: 74 | SU-DHL1 |
| 76 | pyruvate kinase M | Pyruvate kinase-3 | P14618 | Enzyme, cellular metabolism | Y104 | FASDPIyRPVAVAL | SEQ ID NO: 75 | Both |
| 77 | pyruvate kinase M | Pyruvate kinase-3 | P14618 | Enzyme, cellular metabolism | Y389 | REAEAAIyHLQLFEE | SEQ ID NO: 76 | Both |
| 78 | pyruvate kinase M | pyruvate kinase M1 | P14618 | Enzyme, cellular metabolism | Y465 | TARQAHLyRGIFPVL | SEQ ID NO: 77 | SU-DHL1 |
| 79 | pyruvate kinase M | Pyruvate kinase-3 | P14618 | Enzyme, cellular metabolism | Y82 | FSHGTHEyHAETIKN | SEQ ID NO: 78 | Karpas 299 |
| 80 | Nit2 | Nit protein 2 | Q9NQR4 | Enzyme, misc. | Y145 | FSTFDTPyCRVGLGI | SEQ ID NO: 79 | SU-DHL1 |
| 81 | PFKP | phosphofructokinase | Q01813 | Enzyme, misc. | Y651 | NYTTDFIyQLYSEEG | SEQ ID NO: 80 | SU-DHL1 |
| 82 | ATP-citrate lyase | ATP citrate lyase | P53396 | Enzyme, misc.; Lyase | Y131 | YATREGDyVLFHHEG | SEQ ID NO: 81 | SU-DHL1 |
| 83 | ATP-citrate lyase | ATP citrate lyase | P53396 | Enzyme, misc.; Lyase | Y682 | SRTTDGVyEGVAIGG | SEQ ID NO: 82 | SU-DHL1 |
| 84 | Dcp1b | decapping enzyme Dcp1b | Q8IZD4 | Enzyme, misc.; RNA binding protein | Y110 | RNARLSIyGIWFYDK | SEQ ID NO: 83 | Both |
| 85 | Dcp1b | decapping enzyme Dcp1b | Q8IZD4 | Enzyme, misc.; RNA binding protein | Y133 | LMKNLTQyEQLKAHQ | SEQ ID NO: 84 | SU-DHL1 |
| 86 | Dcp1b | decapping enzyme Dcp1b | Q8IZD4 | Enzyme, misc.; RNA binding protein | Y191 | ITSSSAIyDNPNLIK | SEQ ID NO: 85 | Both |
| 87 | Rab GDI alpha | GDP dissociation inhibitor 1 | P31150 | G protein regulator, misc. | Y333 | VNRKSDIyVCMISYA | SEQ ID NO: 86 | SU-DHL1 |
| 88 | Ran | Ran AND RAN protein | P17080 | G protein, monomeric (non-Rab) | Y147 | RKKNLQYyDISAKSN | SEQ ID NO: 87 | SU-DHL1 |
| 89 | TBC1D1 | TBC1 domain member 1 | Q86TI0 | GTPase activating protein, misc. | Y113 | HNSHDPSyFACLIKE | SEQ ID NO: 88 | SU-DHL1 |
| 90 | RasGAP | RAS p21 | P20936 | GTPase activating protein, Ras | Y615 | VKHFTNPyCNIYLNS | SEQ ID NO: 89 | Both |
| 91 | VAV1 | vav 1 oncogene | P15498 | Guanine nucleotide exchange factor, Rac/Rho | Y826 | GWWRGFIyGRVGWFP | SEQ ID NO: 90 | SU-DHL1 |
| 92 | Dicer1 | dicer1 | Q9UPY3 | Helicase | Y654 | ELPDGTFySTLYLPI | SEQ ID NO: 91 | SU-DHL1 |
| 93 | Werner helicase interacting protein | putative helicase RUVBL | Q9Y5S5 | Helicase | Y534 | EGGEDPLyVARRLVR | SEQ ID NO: 92 | SU-DHL1 |
| 94 | Werner helicase interacting protein | putative helicase RUVBL | Q9Y5S5 | Helicase | Y562 | LTQAVAAyQGCHFMG | SEQ ID NO: 93 | SU-DHL1 |
| 95 | DDX5 | DEAD/H box polypep. 5 | P17844 | Helicase; RNA binding protein | Y297 | AEDFLKDyIHINIGA | SEQ ID NO: 94 | SU-DHL1 |
| 96 | HDAC1 | histone deacetylase 1 | Q13547 | Hydrolase, esterase | Y221 | IGAGKGKyYAVNYPL | SEQ ID NO: 95 | SU-DHL1 |
| 97 | deoxycytidylate deaminase | dCMP deaminase | P32321 | Hydrolase, non-esterase | Y79 | ENKLDTKyPYVCHAE | SEQ ID NO: 96 | SU-DHL1 |
| 98 | oligoribonuclease | small fragment nuclease | Q9Y3B8 | Hydrolase, non-esterase | Y122 | ITLQQAEyEFLSFVR | SEQ ID NO: 97 | SU-DHL1 |
| 99 | oligoribonuclease | small fragment nuclease | Q9Y3B8 | Hydrolase, non-esterase | Y184 | RRWYPEEyEFAPKKA | SEQ ID NO: 98 | SU-DHL1 |
| 100 | UDPase | lysosomal apyrase-like 1 | Q9Y227 | Hydrolase, non-esterase | Y385 | QQNGQTIyLRGTGDF | SEQ ID NO: 99 | SU-DHL1 |
| 101 | cysteinyl-tRNA synthetase | cysteine-tRNA synthetase | P49589 | Ligase | Y260 | QKIVDNGyGYVSNGS | SEQ ID NO: 100 | SU-DHL1 |
| 102 | glutaminyl-tRNA synthetase | glutaminyl-tRNA synthetase | P47897 | Ligase | Y491 | YGRLNLHyAVVSKRK | SEQ ID NO: 101 | SU-DHL1 |
| 103 | succinyl-CoA synthetase, betaA chain | succinate-CoA ligase | Q9P2R7 | Ligase | Y84 | AKSPDEAyAIAKKLG | SEQ ID NO: 102 | SU-DHL1 |

FIGURE 2
(Continued)

| | Protein Name (short) | Protein Name (full) | Accession Number | Protein Type | Phospho-Residue | Phosphorylation Site Sequence | SEQ ID NO: | Cell Line |
|---|---|---|---|---|---|---|---|---|
| 104 | E-FABP | fatty acid binding protein 5 | Q01469 | Lipid binding protein | Y131 | NVTCTRIyEKVE | SEQ ID NO: 103 | SU-DHL1 |
| 105 | vigilin | HDL binding protein AND vigilin | Q00341 | Lipid binding protein; RNA binding protein; Transporter, facilitator | Y437 | DLINRMDyVEINIDH | SEQ ID NO: 104 | Both |
| 106 | ATP-citrate lyase | ATP citrate lyase | P53396 | Lyase; Enzyme, misc. | Y131 | YATREGDyVLFHHEG | SEQ ID NO: 105 | SU-DHL1 |
| 107 | ATP-citrate lyase | ATP citrate lyase | P53396 | Lyase; Enzyme, misc. | Y682 | SRTTDGVyFGVAIGG | SEQ ID NO: 106 | SU-DHL1 |
| 108 | MDS024 | MDS024 protein | Q9HC13 | Methyltransferase; RNA binding protein | Y44 | FASSQETyGKSPFWI | SEQ ID NO: 107 | SU-DHL1 |
| 109 | MKLP1 | mitotic kinesin-like 1 | O02241 | Motor protein; Calcium-binding protein | Y29 | LKDPVGVyCRVRPLG | SEQ ID NO: 108 | SU-DHL1 |
| 110 | glutathione reductase | glutathione reductase | P00390 | Oxidoreductase | Y65 | AAGAVASyDYLVIGG | SEQ ID NO: 109 | Both |
| 111 | malate dehydrogenase 2 | mito. malate dehydrogenase | P40926 | Oxidoreductase | Y56 | LVSRLTLyDIAHTPG | SEQ ID NO: 110 | SU-DHL1 |
| 112 | thioredoxin reductase 1 | thioredoxin reductase 1 | Q16881 | Oxidoreductase | Y11 | PEDLPKSyDYDLIII | SEQ ID NO: 111 | Both |
| 113 | thioredoxin reductase 1 | thioredoxin reductase 1 | Q16881 | Oxidoreductase | Y13 | DLPKSYDyDLIIGG | SEQ ID NO: 112 | Both |
| 114 | thioredoxin reductase 1 | thioredoxin reductase 1 | Q16881 | Oxidoreductase | Y131 | KVVYENAyGQFIGPH | SEQ ID NO: 113 | Both |
| 115 | thioredoxin reductase 1 | thioredoxin reductase 1 | Q16881 | Oxidoreductase | Y422 | SRDNNKCyAKIICNT | SEQ ID NO: 114 | SU-DHL1 |
| 116 | nudix-type motif 5 | nudix-type motif 5 | Q9UKK9 | Phosphatase | Y74 | VLQRTLHyECIVLVK | SEQ ID NO: 115 | Both |
| 117 | INPP4 | inos. polyphos.-4-ppase I | O15326 | Phosphatase, lipid | Y355 | DGGSDQNyDIVTIGA | SEQ ID NO: 116 | Karpas 299 |
| 118 | Casp8 | caspase 8 isoform A | Q14790 | Protease (non-proteasomal); Apoptosis | Y334 | DGQEAPIyELTSQFT | SEQ ID NO: 117 | Karpas 299 |
| 119 | Proteasome component C3 | proteasome alpha 2 subunit | P25787 | Protease (proteasomal subunit) | Y23 | GKLVQIEyALAAVAG | SEQ ID NO: 118 | Both |
| 120 | Proteasome component C3 | proteasome alpha 2 subunit | P25787 | Protease (proteasomal subunit) | Y97 | RKLAQQYyLVYQEPI | SEQ ID NO: 119 | SU-DHL1 |
| 121 | proteasome component C8 | proteasome subunit C8 | P25788 | Protease (proteasomal subunit) | Y160 | PSGVSYGyWGCAIGK | SEQ ID NO: 120 | SU-DHL1 |
| 122 | proteasome component N3 | proteasome beta 4 subunit | P28070 | Protease (proteasomal subunit) | Y102 | MLGASGDyADFQYLK | SEQ ID NO: 121 | Both |
| 123 | proteasome component Poh1 | 26S proteasome-assoc. pad 1 | O00487 | Protease (proteasomal subunit) | Y32 | VDTAEQVyISSLALL | SEQ ID NO: 122 | SU-DHL1 |
| 124 | proteasome component Z | proteasome subunit Z | Q99436 | Protease (proteasomal subunit) | Y154 | DVTGPHLySIYPHGS | SEQ ID NO: 123 | SU-DHL1 |
| 125 | A6r | protein tyrosine kinase 9-like | Q9Y3F5 | Protein kinase | Y309 | ELTAEFLyDEVHPKQ | SEQ ID NO: 124 | Both |
| 126 | A6 | protein tyrosine kinase 9 | Q12792 | Protein kinase, dual-specificity | Y327 | ELTADFLyEEVHPKQ | SEQ ID NO: 125 | SU-DHL1 |
| 127 | DYRK1A | DYRK1A | Q13627 | Protein kinase, dual-specificity | Y145 | DGYDDDNyDYIVKNG | SEQ ID NO: 126 | Both |
| 128 | DYRK3 | DYRK3 | O43781 | Protein kinase, dual-specificity | Y209 | RDHLAYRyEVLKIIG | SEQ ID NO: 127 | SU-DHL1 |
| 129 | Cdc2 | cdc2 | P06493 | Protein kinase, Ser/Thr (non-receptor) | Y19 | EGTYGVVyKGRHKTT | SEQ ID NO: 128 | Both |
| 130 | GSK3-alpha | GSK3 alpha | P49840 | Protein kinase, Ser/Thr (non-receptor) | Y279 | RGEPNVSyICSRYYR | SEQ ID NO: 129 | Both |
| 131 | HIPK1 | HIPK 1 | Q86Z02 | Protein kinase, Ser/Thr (non-receptor) | Y352 | SKAVCSTyLQSRYYR | SEQ ID NO: 130 | SU-DHL1 |
| 132 | HIPK3 | HIPK 3 | O14632 | Protein kinase, Ser/Thr (non-receptor) | Y359 | SKTVCSTyLQSRYYR | SEQ ID NO: 131 | SU-DHL1 |
| 133 | PRP4 | PRP4K | Q13523 | Protein kinase, Ser/Thr (non-receptor) | Y849 | ADNDITPyLVSRFYR | SEQ ID NO: 132 | Both |
| 134 | SgK223 | FLJ00269 protein | Q86YV5 | Protein kinase, Ser/Thr (non-receptor) | Y390 | ATQPEPIyAESTKRK | SEQ ID NO: 133 | Karpas 299 |
| 135 | Ack | activated p21cdc42Hs kinase | Q07912 | Protein kinase, tyrosine (non-receptor) | Y518 | GGVKKPTyDPVSEDQ | SEQ ID NO: 134 | SU-DHL1 |
| 136 | Jak3 | Janus kinase 3 | P52333 | Protein kinase, tyrosine (non-receptor) | Y785 | NSLISSDyELLSDPT | SEQ ID NO: 135 | Both |
| 137 | SHP-2 | SHP2 | Q06124 | Protein phosphatase, tyrosine (non-receptor) | Y62 | KIQNTGDyYDLYGGE | SEQ ID NO: 136 | Both |
| 138 | laminin receptor 1 | laminin receptor 1 | P08865 | Receptor, misc.; Adhesion | Y139 | QPLTEASyVNLPTIA | SEQ ID NO: 137 | Both |
| 139 | ALK | anaplastic lymphoma kinase | Q9UM73 | Receptor tyrosine kinase | Y1078 | MELQSPEyKLSKLRT | SEQ ID NO: 138 | SU-DHL1 |
| 140 | ALK | anaplastic lymphoma kinase | Q9UM73 | Receptor tyrosine kinase | Y1092 | TSTIMTDyNPNYCFA | SEQ ID NO: 139 | Both |
| 141 | ALK | anaplastic lymphoma kinase | Q9UM73 | Receptor tyrosine kinase | Y1131 | HGAFGEVyEGQVSGM | SEQ ID NO: 140 | Both |
| 142 | ALK | anaplastic lymphoma kinase | Q9UM73 | Receptor tyrosine kinase | Y1278 | FGMARDIyRASYYRK | SEQ ID NO: 141 | SU-DHL1 |
| 143 | ALK | anaplastic lymphoma kinase | Q9UM73 | Receptor tyrosine kinase | Y1282 | RDIYRASyYRKGGCA | SEQ ID NO: 142 | SU-DHL1 |
| 144 | ALK | anaplastic lymphoma kinase | Q9UM73 | Receptor tyrosine kinase | Y1584 | FPCGNVNyGYQQQGL | SEQ ID NO: 143 | Both |
| 145 | hnRNP H | hnRNP H1 | P31943 | RNA binding protein | Y306 | RATENDIyNFFSPLN | SEQ ID NO: 144 | Both |
| 146 | hnRNP-A1 | hnRNP A1B | P09651 | RNA binding protein | Y346 | PYGGGGQyFAKPRNQ | SEQ ID NO: 145 | SU-DHL1 |
| 147 | LSm2 | U6 small nuclear RNA assoc. | Q9Y333 | RNA binding protein | Y35 | TLHSVDQyLNIKLTD | SEQ ID NO: 146 | Karpas 299 |
| 148 | mRNA cleavage factor Im | pre-mRNA cleavage fac. Im | O43809 | RNA binding protein | Y40 | LERTINLvPLTNYTF | SEQ ID NO: 147 | SU-DHL1 |
| 149 | mRNA cleavage factor, 50 kDa subunit | cleavage stim. factor sub. 1 | Q05048 | RNA binding protein | Y367 | VFNHTEDyVLLPDER | SEQ ID NO: 148 | Both |
| 150 | MVP | major vault protein | Q14764 | RNA binding protein | Y13 | FIIRIPPyHYIHVLD | SEQ ID NO: 149 | Karpas 299 |
| 151 | PABP 1 | poly(A) BP, cytoplasmic 1 | P11940 | RNA binding protein | Y364 | IVATKPLyVALAQRK | SEQ ID NO: 150 | SU-DHL1 |
| 152 | PABP 1 | Poly(A)-binding protein 1 | P11940 | RNA binding protein | Y54 | ITRRSLGyAYVNFQQ | SEQ ID NO: 151 | Both |
| 153 | PABP 4 | PABP4 | Q13310 | RNA binding protein | Y140 | DENGSKGyAFVHFET | SEQ ID NO: 152 | SU-DHL1 |
| 154 | RNA-binding protein S1 | RNA-binding protein S1 | Q15287 | RNA binding protein | Y205 | HPHLSKGyAYVEFEN | SEQ ID NO: 153 | Both |

FIGURE 2
(Continued)

| | A | B | C | D | F | G | H | I |
|---|---|---|---|---|---|---|---|---|
| 1 | Protein Name (short) | Protein Name (full) | Accession Number | Protein Type | Phospho-Residue | Phosphorylation Site Sequence | SEQ ID NO: | Cell Line |
| 155 | snRNP B | snRNP polypeptide B | P08579 | RNA binding protein | Y151 | VPDYPPNyILFLNNL | SEQ ID NO: 154 | SU-DHL1 |
| 156 | splicing factor 2 | splicing factor, Arg/Ser-rich1 | Q07955 | RNA binding protein | Y188 | SHEGETAyIRVKVDG | SEQ ID NO: 155 | SU-DHL1 |
| 157 | splicing factor 3A subunit 1 | splicing factor 3a, subunit 1 | Q15459 | RNA binding protein | Y759 | AGKQKLQyEGIFIKD | SEQ ID NO: 156 | Both |
| 158 | splicing factor 3A subunit 3 | splicing factor 3a, subunit 3 | Q12874 | RNA binding protein | Y414 | NCEICGNyTYRGPKA | SEQ ID NO: 157 | Both |
| 159 | splicing factor 3B subunit 4 | splicing factor 3b, subunit 4 | Q15427 | RNA binding protein | Y56 | VTGQHQGyGFVEFLS | SEQ ID NO: 158 | SU-DHL1 |
| 160 | splicing factor 3B, 14 kDa subunit | splicing factor 3B | Q9Y3B4 | RNA binding protein | Y86 | GFNVCNRyLVVLYYN | SEQ ID NO: 159 | SU-DHL1 |
| 161 | splicing factor, Arg/Ser-rich 4 | splicing factor R/S-rich 4 | Q08170 | RNA binding protein | Y53 | RDADDAVyELNGKDL | SEQ ID NO: 160 | Karpas 299 |
| 162 | nucleolysin, TIA-1-related | T-cluster binding protein | Q01085 | RNA binding protein; Apoptosis | Y50 | EHTSNDPyCFVEFYE | SEQ ID NO: 161 | SU-DHL1 |
| 163 | prohibitin, D | B-cell associated protein | Q99623 | RNA binding protein; Chaperone | Y128 | YQRLGLDyEERVLPS | SEQ ID NO: 162 | SU-DHL1 |
| 164 | hnRNP U | hnRNP U isoform b | Q00839 | RNA binding protein; DNA binding protein | Y454 | YFPIPEEyTFIQNVP | SEQ ID NO: 163 | Both |
| 165 | Dcp1b | decapping enzyme Dcp1b | Q8IZD4 | RNA binding protein; Enzyme, misc. | Y110 | RNARLSIyGIWFYDK | SEQ ID NO: 164 | Both |
| 166 | Dcp1b | decapping enzyme Dcp1b | Q8IZD4 | RNA binding protein; Enzyme, misc. | Y133 | LMKNLTQyEQLKAHQ | SEQ ID NO: 165 | SU-DHL1 |
| 167 | Dcp1b | decapping enzyme Dcp1b | Q8IZD4 | RNA binding protein; Enzyme, misc. | Y191 | ITSSSAIyDNPNLIK | SEQ ID NO: 166 | Both |
| 168 | DDX5 | DEAD/H box polypep. 5 | P17844 | RNA binding protein; Helicase | Y297 | AEDFLKDyIHINIGA | SEQ ID NO: 167 | SU-DHL1 |
| 169 | MDS024 | MDS024 protein | Q9HC13 | RNA binding protein; Methyltransferase | Y44 | FASSQETyGKSPFWI | SEQ ID NO: 168 | SU-DHL1 |
| 170 | vigilin | HDL binding protein AND vigilin | Q00341 | RNA binding protein; Transporter, facilitator; Lipid binding protein | Y437 | DLINRMDyVEINIDH | SEQ ID NO: 169 | Both |
| 171 | GRF-1 | gluco. rec. DNA BF iso. 1a | Q9NRY4 | Transcription factor | Y1105 | RNEEENIySVPHDST | SEQ ID NO: 170 | SU-DHL1 |
| 172 | HZF2 | zinc finger protein 267 | Q14586 | Transcription factor | Y520 | IHTGENLyKCKVCAK | SEQ ID NO: 171 | Karpas 299 |
| 173 | transcription factor 20 | Transcription factor 20 | Q9UGU0 | Transcription factor | Y548 | STSSDTTyKGGASEK | SEQ ID NO: 172 | SU-DHL1 |
| 174 | zinc finger protein 147 | zinc finger protein 147 | Q14258 | Transcription factor | Y278 | NSKFDTIyQILLKKK | SEQ ID NO: 173 | Both |
| 175 | zinc finger protein 174 | zinc finger protein 174 | Q15697 | Transcription factor | Y382 | IHTGEKPyQCGQCGK | SEQ ID NO: 174 | SU-DHL1 |
| 176 | zinc finger protein 24 | zinc finger protein 24 | P17028 | Transcription factor | Y279 | IHSGEKPyGCVECGK | SEQ ID NO: 175 | Karpas 299 |
| 177 | zinc finger protein 24 | zinc finger protein 24 | P17028 | Transcription factor | Y335 | IHTGEKPyECVQCGK | SEQ ID NO: 176 | Both |
| 178 | zinc finger protein 264 | zinc finger protein 264 | O43296 | Transcription factor | Y231 | IHSGVKPyECTECGK | SEQ ID NO: 177 | SU-DHL1 |
| 179 | zinc finger protein 264 | zinc finger protein 264 | O43296 | Transcription factor | Y343 | VHSGENPyECLECGK | SEQ ID NO: 178 | Both |
| 180 | zinc finger protein 264 | hypothetical prot. FLJ20079 AND zinc finger protein 264 | O43296 | Transcription factor | Y483 | IHTGEKPyECVECGK | SEQ ID NO: 179 | Both |
| 181 | zinc finger protein 264 | zinc finger protein 264 | O43296 | Transcription factor | Y511 | IHSGEKPyECVECGK | SEQ ID NO: 180 | Both |
| 182 | Sui1 | eIF1 | P41567 | Transcription initiation complex | Y30 | LPAGTEDyIHIRIQQ | SEQ ID NO: 181 | Both |
| 183 | SSRP1 | structure spec. recog. pro. 1 | Q08945 | Transcription initiation complex; Transcription, coactivator/corepressor | Y311 | KNMSGSLyEMVSRVM | SEQ ID NO: 182 | SU-DHL1 |
| 184 | EBNA-2 coactivator | EBNA-2 co-activator | Q13122 | Transcription, coactivator/corepressor | Y84 | KTPQGREyGMIYLGK | SEQ ID NO: 183 | SU-DHL1 |
| 185 | TRIP13 | thyroid receptor int. pro. 13 | Q15645 | Transcription, coactivator/corepressor | Y58 | HNIVFGDyTWTEFDE | SEQ ID NO: 184 | Karpas 299 |
| 186 | SSRP1 | structure spec. recog. pro. 1 | Q08945 | Transcription, coactivator/corepressor; Transcription initiation complex | Y311 | KNMSGSLyEMVSRVM | SEQ ID NO: 185 | SU-DHL1 |
| 187 | DNA primase 2A | primase, polypep. 2A, 58kDa | P49643 | Transferase | Y381 | NPPSQGDyHGCPFRH | SEQ ID NO: 186 | Both |
| 188 | farnesyltransferase beta | farnesyltransferase, beta | P49356 | Transferase | Y300 | NKLVDGCySFWQAGL | SEQ ID NO: 187 | Both |
| 189 | glycogen branching enzyme | Glycogen branching enzyme | Q04446 | Transferase | Y173 | REGDNVNyDWIHWDP | SEQ ID NO: 188 | Both |
| 190 | spermine synthase | spermine synthase | P52788 | Transferase | Y147 | VYDFDSPyQNIKILH | SEQ ID NO: 189 | SU-DHL1 |
| 191 | transketolase | transketolase | P29401 | Transferase | Y275 | EQIIQEIySQIQSKK | SEQ ID NO: 190 | Both |
| 192 | eEF1A-2 | elongation factor 1-alpha | Q05639 | Translation initiation complex | Y141 | REHALLAyTLGVKQL | SEQ ID NO: 191 | Both |
| 193 | eIF3-beta | eIF3 subunit 2-beta | Q13347 | Translation initiation complex | Y308 | SSGGEDGyVRIHYFD | SEQ ID NO: 192 | SU-DHL1 |
| 194 | eIF3-eta | eIF3 subunit 9 eta | P55884 | Translation initiation complex | Y525 | HWQKNGDyLCVKVDR | SEQ ID NO: 193 | SU-DHL1 |
| 195 | eIF3-zeta | eIF3 subunit 7 | O15371 | Translation initiation complex | Y318 | NLAMEATyINHNFSQ | SEQ ID NO: 194 | SU-DHL1 |
| 196 | eIF6 | integrin-binding prot. iso. | P56537 | Translation initiation complex | Y113 | NVTTCNDyVALVHPD | SEQ ID NO: 195 | SU-DHL1 |
| 197 | ribosomal protein L12 | ribosomal protein L12 | P30050 | Translation initiation complex | Y14 | PNEIKVVyLRCTGGE | SEQ ID NO: 196 | SU-DHL1 |
| 198 | ribosomal protein L18a | ribosomal protein L18a | Q02543 | Translation initiation complex | Y63 | KSSGEIVyCGQVFEK | SEQ ID NO: 197 | Both |
| 199 | ribosomal protein L23 | ribosomal protein L23 | P23131 | Translation initiation complex | Y38 | NTGAKNLyIISVKGI | SEQ ID NO: 198 | SU-DHL1 |
| 200 | ribosomal protein L31 | ribosomal protein L31 | P12947 | Translation initiation complex | Y103 | EDSPNKLyTLVTYVP | SEQ ID NO: 199 | Both |
| 201 | ribosomal protein L31 | ribosomal protein L31 | P12947 | Translation initiation complex | Y108 | KLYTLVTyVPVTTFK | SEQ ID NO: 200 | Karpas 299 |
| 202 | ribosomal protein L7 | ribosomal protein L7 | P18124 | Translation initiation complex | Y139 | MLRIVEPyIAWGYPN | SEQ ID NO: 201 | Both |
| 203 | ribosomal protein L7 | ribosomal protein L7 | P18124 | Translation initiation complex | Y195 | EDLIHEIyTVGKRFK | SEQ ID NO: 202 | Karpas 299 |
| 204 | ribosomal protein L8 | ribosomal protein L8 | P25120 | Translation initiation complex | Y132 | LARASGNyATVISHN | SEQ ID NO: 203 | Both |
| 205 | ribosomal protein P0 | ribosomal protein P0 | P05388 | Translation initiation complex | Y24 | IIQLLDDyPKCFIVG | SEQ ID NO: 204 | Both |
| 206 | ribosomal protein S10 | ribosomal protein S10 | P46783 | Translation initiation complex | Y12 | KKNRIAIyELLFKEG | SEQ ID NO: 205 | Both |

FIGURE 2
(Continued)

| | A | B | C | D | F | G | H | I |
|---|---|---|---|---|---|---|---|---|
| 1 | Protein Name (short) | Protein Name (full) | Accession Number | Protein Type | Phospho-Residue | Phosphorylation Site Sequence | SEQ ID NO: | Cell Line |
| 207 | ribosomal protein S13 | ribosomal protein S13 | Q02546 | Translation initiation complex | Y37 | DDVKEQIyKLAKKGL | SEQ ID NO: 206 | SU-DHL1 |
| 208 | RanBP7 | RAN-binding protein 7 | O95373 | Transporter, facilitator | Y311 | LLKVLYQyKEKQYMA | SEQ ID NO: 207 | SU-DHL1 |
| 209 | vigilin | HDL binding protein AND vigilin | Q00341 | Transporter, facilitator; RNA binding protein; Lipid binding protein | Y437 | DLINRMDyVEINIDH | SEQ ID NO: 208 | Both |
| 210 | sequestosome 1 | sequestosome 1 | Q13501 | Ubiquitin conjugating system | Y148 | KCSVCPDyDLCSVCE | SEQ ID NO: 209 | Karpas 299 |
| 211 | adaptin, beta | adaptin, beta 2 | P21851 | Vesicle protein | Y737 | THRQGHIyMEMNFTN | SEQ ID NO: 210 | SU-DHL1 |
| 212 | HEP-COP | alpha coat protein | P53621 | Vesicle protein | Y249 | VDTCRGHvNNVSCAV | SEQ ID NO: 211 | SU-DHL1 |

SEQUENCE LISTING

<160> NUMBER OF SEQ ID NOS: 211

<210> SEQ ID NO 1
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 1

Gly His Thr Ser Asn Asn Ile Tyr Glu Ala Val Lys Tyr Ser Glu
1               5                   10                  15

<210> SEQ ID NO 2
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 2

Leu Lys Asp Pro Asp Gln Leu Tyr Thr Thr Leu Lys Asn Leu Leu
1               5                   10                  15

<210> SEQ ID NO 3
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 3

Asp Gly Thr Phe Asp Asn Ile Tyr Leu His Val Gln Ile Ser Asn
1               5                   10                  15

<210> SEQ ID NO 4
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 4

Gln Glu Lys Ser Glu Gly Thr Tyr Cys Cys Gly Pro Val Pro Val
1               5                   10                  15

<210> SEQ ID NO 5
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 5

```
Glu Ile Thr Asp Glu Ser Pro Tyr Val His Tyr Leu Asn Thr Phe
1               5                   10                  15

<210> SEQ ID NO 6
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 6

His Asp Asp Gly Arg Val Ser Tyr Pro Leu Cys Phe Ile Phe Ser
1               5                   10                  15

<210> SEQ ID NO 7
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 7

Ser Tyr Ser Glu Glu Lys Tyr Ala Phe Val Asn Trp Ile Asn
1               5                   10                  15

<210> SEQ ID NO 8
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 8

Lys Ala His Asp Gly Gly Ile Tyr Ala Ile Ser Trp Ser Pro Asp
1               5                   10                  15

<210> SEQ ID NO 9
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 9

Gly Leu Ile Asn Lys Lys Cys Tyr Glu Met Ala Ser His Leu Arg
1               5                   10                  15

<210> SEQ ID NO 10
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 10
```

-continued

Leu Val Gln Arg Ile Ser Thr Tyr Gly Leu Pro Ala Gly Gly Ile
1               5                   10                  15

<210> SEQ ID NO 11
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 11

Gln Asn Leu Asn Thr Ile Thr Tyr Glu Thr Leu Lys Tyr Ile Ser
1               5                   10                  15

<210> SEQ ID NO 12
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 12

Asn Leu Gln Asn Gly Pro Ile Tyr Ala Arg Val Ile Gln Lys Arg
1               5                   10                  15

<210> SEQ ID NO 13
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 13

Val Arg Val Cys Glu Pro Cys Tyr Glu Gln Leu Asn Arg Lys Ala
1               5                   10                  15

<210> SEQ ID NO 14
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 14

Gln Pro Ala Ser Val Thr Asp Tyr Gln Asn Val Ser Phe Ser Asn
1               5                   10                  15

<210> SEQ ID NO 15
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 15

```
Arg Glu Glu Pro Glu Ala Leu Tyr Ala Ala Val Asn Lys Lys Pro
1               5                   10                  15

<210> SEQ ID NO 16
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 16

Gly Gly Pro Ala Arg Leu Glu Tyr Tyr Glu Asn Glu Lys Lys Trp
1               5                   10                  15

<210> SEQ ID NO 17
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 17

Gln Arg Val Asp Pro Asn Gly Tyr Met Met Met Ser Pro Ser Gly
1               5                   10                  15

<210> SEQ ID NO 18
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 18

Leu Asn Glu Gly Lys His Leu Tyr Thr Leu Asp Gly Gly Asp Ile
1               5                   10                  15

<210> SEQ ID NO 19
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 19

Ser Gln Asp Pro Asn Pro Gln Tyr Ser Pro Ile Ile Lys Gln Gly
1               5                   10                  15

<210> SEQ ID NO 20
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 20
```

```
Gly Glu Ala Pro Ser Asn Ile Tyr Val Glu Val Glu Asp Glu Gly
1               5                   10                  15
```

<210> SEQ ID NO 21
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 21

```
Arg Ser Cys Gln Asn Leu Gly Tyr Thr Ala Ala Ser Pro Gln Ala
1               5                   10                  15
```

<210> SEQ ID NO 22
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 22

```
Ser Ala Arg Ile Gln Arg Ala Tyr Asn His Tyr Phe Asp Leu Ile
1               5                   10                  15
```

<210> SEQ ID NO 23
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 23

```
Gln Pro Leu Thr Glu Ala Ser Tyr Val Asn Leu Pro Thr Ile Ala
1               5                   10                  15
```

<210> SEQ ID NO 24
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 24

```
Gln Glu Val Lys Arg Asn Val Tyr Asp Leu Thr Ser Ile Pro Val
1               5                   10                  15
```

<210> SEQ ID NO 25
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 25

```
Asp Asp Gln Glu Asn Cys Val Tyr Glu Thr Val Val Leu Pro Leu
1               5                   10                  15
```

<210> SEQ ID NO 26
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 26

```
Asp Gly Gln Glu Ala Pro Ile Tyr Glu Leu Thr Ser Gln Phe Thr
1               5                   10                  15
```

<210> SEQ ID NO 27
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 27

```
Glu His Thr Ser Asn Asp Pro Tyr Cys Phe Val Glu Phe Tyr Glu
1               5                   10                  15
```

<210> SEQ ID NO 28
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 28

```
Asp Ser Asp Ala Arg Ala Leu Tyr Glu Ala Gly Glu Arg Arg Lys
1               5                   10                  15
```

<210> SEQ ID NO 29
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 29

```
Leu Lys Asp Pro Val Gly Val Tyr Cys Arg Val Arg Pro Leu Gly
1               5                   10                  15
```

<210> SEQ ID NO 30
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 30

Gly Leu Ser Phe Glu Glu Leu Tyr Arg Asn Ala Tyr Thr Met Val
1               5                   10                  15

<210> SEQ ID NO 31
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 31

Pro Ala Leu Glu Asp Phe Val Tyr Lys Ile Phe Gly Pro Gly Lys
1               5                   10                  15

<210> SEQ ID NO 32
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 32

Thr Glu Phe Gly Gly Ser Ile Tyr Gln Lys Val Asn Lys Lys Leu
1               5                   10                  15

<210> SEQ ID NO 33
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 33

Thr Glu Phe Gly Gly Ser Ile Tyr Gln Lys Val Asn Glu Lys Ile
1               5                   10                  15

<210> SEQ ID NO 34
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 34

Asp Arg Gly Tyr Ile Ser Pro Tyr Phe Ile Asn Thr Ser Lys Gly
1               5                   10                  15

<210> SEQ ID NO 35
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 35

Lys Leu Lys Lys Glu Asp Ile Tyr Ala Val Glu Ile Val Gly Gly
1               5                   10                  15

<210> SEQ ID NO 36
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 36

Ala Glu Lys Ser Asn Leu Ala Tyr Asp Ile Val Gln Leu Pro Thr
1               5                   10                  15

<210> SEQ ID NO 37
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 37

Lys Glu Thr Gln Lys Ser Ile Tyr Tyr Ile Thr Gly Glu Ser Lys
1               5                   10                  15

<210> SEQ ID NO 38
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 38

Leu Asp Thr Tyr Leu Gly Lys Tyr Trp Ala Ile Lys Leu Ala Thr
1               5                   10                  15

<210> SEQ ID NO 39
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 39

Asp Tyr Asn Glu Ala Tyr Asn Tyr Tyr Thr Lys Ala Ile Asp Met
1               5                   10                  15

<210> SEQ ID NO 40
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 40

```
Tyr Gln Arg Leu Gly Leu Asp Tyr Glu Glu Arg Val Leu Pro Ser
1               5                   10                  15

<210> SEQ ID NO 41
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 41

Ala Thr Gly Lys Pro Pro Gln Tyr Ile Ala Val His Val Val Pro
1               5                   10                  15

<210> SEQ ID NO 42
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 42

Gly Asn Leu Asp Gly Leu Glu Tyr Lys Leu His Asp Phe Gly Tyr
1               5                   10                  15

<210> SEQ ID NO 43
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 43

Asp Ile Lys Glu Lys Leu Cys Tyr Val Ala Leu Asp Phe Glu Asn
1               5                   10                  15

<210> SEQ ID NO 44
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 44

Asp Ile Lys Glu Lys Leu Cys Tyr Val Ala Leu Asp Phe Glu Gln
1               5                   10                  15

<210> SEQ ID NO 45
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 45
```

```
Val Asp Ile Arg Lys Asp Leu Tyr Ala Asn Thr Val Leu Ser Gly
1               5                   10                  15

<210> SEQ ID NO 46
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 46

Ala Lys Ala Val Lys Glu Arg Tyr Ser Tyr Val Cys Pro Asp Leu
1               5                   10                  15

<210> SEQ ID NO 47
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 47

Asp Ser His Glu Asp Gly Asp Tyr Tyr Glu Val Asp Ile Asn Gly
1               5                   10                  15

<210> SEQ ID NO 48
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 48

His Glu Leu Gln Ala Asn Cys Tyr Glu Glu Val Lys Asp Arg Cys
1               5                   10                  15

<210> SEQ ID NO 49
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 49

Ile Ile Asn Gln Glu Gly Glu Tyr Ile Lys Met Phe Met Arg Gly
1               5                   10                  15

<210> SEQ ID NO 50
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 50
```

```
Gly Met Gly Gln Lys Asp Ser Tyr Val Gly Asn Glu Ala Gln Ser
1               5                   10                  15
```

<210> SEQ ID NO 51
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 51

```
Tyr Gly Val Glu Asp Pro Glu Tyr Ala Val Thr Gln Leu Ala Gln
1               5                   10                  15
```

<210> SEQ ID NO 52
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 52

```
Glu Ala Gly Lys Ala Leu Asp Tyr Tyr Met Leu Arg Asn Gly Asp
1               5                   10                  15
```

<210> SEQ ID NO 53
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 53

```
Ile His Phe Pro Leu Ala Thr Tyr Ala Pro Val Ile Ser Ala Glu
1               5                   10                  15
```

<210> SEQ ID NO 54
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 54

```
Arg Asn Leu Asp Pro Leu Val Tyr Leu Leu Ser Lys Leu Thr Glu
1               5                   10                  15
```

<210> SEQ ID NO 55
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 55

```
Gln Ala Phe Ser Arg Val Gln Ile Tyr His Asn Pro Thr Ala Asn
1               5                  10                  15
```

<210> SEQ ID NO 56
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 56

```
Leu Asn Asp Arg Phe Ala Asn Tyr Ile Asp Lys Val Arg Phe Leu
1               5                  10                  15
```

<210> SEQ ID NO 57
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 57

```
Gly Leu Ile Asn Lys Lys Cys Tyr Glu Met Ala Ser His Leu Arg
1               5                  10                  15
```

<210> SEQ ID NO 58
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 58

```
Lys Arg Ile Ser Gly Leu Ile Tyr Glu Glu Thr Arg Gly Val Leu
1               5                  10                  15
```

<210> SEQ ID NO 59
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 59

```
Lys Val Trp Leu Leu Gln Gln Tyr Ser Gly Met Thr His Glu Asp
1               5                  10                  15
```

<210> SEQ ID NO 60
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 60

```
Gly Met Asp Pro Ser Asp Ile Tyr Ala Val Ile Gln Ile Pro Gly
1               5                   10                  15

<210> SEQ ID NO 61
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 61

Tyr Phe Pro Ile Pro Glu Glu Tyr Thr Phe Ile Gln Asn Val Pro
1               5                   10                  15

<210> SEQ ID NO 62
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 62

His Leu Tyr Pro Asn Thr Pro Tyr Ala Tyr Thr Phe Trp Thr Tyr
1               5                   10                  15

<210> SEQ ID NO 63
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 63

His Asp Leu Lys Arg Cys Gln Tyr Val Thr Glu Lys Val Leu Ala
1               5                   10                  15

<210> SEQ ID NO 64
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 64

Tyr Lys Ser Phe Ile Lys Asp Tyr Pro Val Val Ser Ile Glu Asp
1               5                   10                  15

<210> SEQ ID NO 65
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 65
```

```
Ser Gly Ala Ser Thr Gly Ile Tyr Glu Ala Leu Glu Leu Arg Asp
1               5                   10                  15

<210> SEQ ID NO 66
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 66

Ser Gly Ala Ser Thr Gly Ile Tyr Glu Ala Leu Glu Leu Arg Asp
1               5                   10                  15

<210> SEQ ID NO 67
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 67

Val Gln Pro Asn Glu Ala Val Tyr Thr Lys Met Met Thr Lys Lys
1               5                   10                  15

<210> SEQ ID NO 68
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 68

Asp Pro Phe Ile Asp Leu Asn Tyr Met Val Tyr Met Phe Gln Tyr
1               5                   10                  15

<210> SEQ ID NO 69
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 69

Ser Lys Gly Tyr Pro Gly Asp Tyr Thr Lys Gly Val Glu Ile Thr
1               5                   10                  15

<210> SEQ ID NO 70
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 70
```

```
Thr Thr Glu Ala Pro Gly Glu Tyr Phe Phe Ser Asp Gly Ile Arg
1               5                   10                  15

<210> SEQ ID NO 71
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 71

Lys Gln Val Val Glu Ser Ala Tyr Glu Val Ile Lys Leu Lys Gly
1               5                   10                  15

<210> SEQ ID NO 72
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 72

Lys Met Val Val Glu Ser Ala Tyr Glu Val Ile Lys Leu Lys Gly
1               5                   10                  15

<210> SEQ ID NO 73
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 73

Arg Asn Glu Lys Cys His Asp Tyr Tyr Thr Thr Glu Phe Leu Tyr
1               5                   10                  15

<210> SEQ ID NO 74
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 74

Leu Met Lys Lys Glu Leu Asn Tyr Phe Ala Lys Ala Leu Glu Ser
1               5                   10                  15

<210> SEQ ID NO 75
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 75
```

```
Phe Ala Ser Asp Pro Ile Leu Tyr Arg Pro Val Ala Val Ala Leu
1               5                   10                  15

<210> SEQ ID NO 76
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 76

Arg Glu Ala Glu Ala Ala Ile Tyr His Leu Gln Leu Phe Glu Glu
1               5                   10                  15

<210> SEQ ID NO 77
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 77

Thr Ala Arg Gln Ala His Leu Tyr Arg Gly Ile Phe Pro Val Leu
1               5                   10                  15

<210> SEQ ID NO 78
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; ; tyrosine at position 8
      is phosphorylatable

<400> SEQUENCE: 78

Phe Ser His Gly Thr His Glu Tyr His Ala Glu Thr Ile Lys Asn
1               5                   10                  15

<210> SEQ ID NO 79
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 79

Phe Ser Thr Phe Asp Thr Pro Tyr Cys Arg Val Gly Leu Gly Ile
1               5                   10                  15

<210> SEQ ID NO 80
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 80
```

```
Asn Tyr Thr Thr Asp Phe Ile Tyr Gln Leu Tyr Ser Glu Glu Gly
1               5                   10                  15

<210> SEQ ID NO 81
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 81

Tyr Ala Thr Arg Glu Gly Asp Tyr Val Leu Phe His His Glu Gly
1               5                   10                  15

<210> SEQ ID NO 82
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 82

Ser Arg Thr Thr Asp Gly Val Tyr Glu Gly Val Ala Ile Gly Gly
1               5                   10                  15

<210> SEQ ID NO 83
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 83

Arg Asn Ala Arg Leu Ser Ile Tyr Gly Ile Trp Phe Tyr Asp Lys
1               5                   10                  15

<210> SEQ ID NO 84
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 84

Leu Met Lys Asn Leu Thr Gln Tyr Glu Gln Leu Lys Ala His Gln
1               5                   10                  15

<210> SEQ ID NO 85
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 85
```

-continued

```
Ile Thr Ser Ser Ser Ala Ile Tyr Asp Asn Pro Asn Leu Ile Lys
1               5                   10                  15

<210> SEQ ID NO 86
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 86

Val Asn Arg Lys Ser Asp Ile Tyr Val Cys Met Ile Ser Tyr Ala
1               5                   10                  15

<210> SEQ ID NO 87
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 87

Arg Lys Lys Asn Leu Gln Tyr Tyr Asp Ile Ser Ala Lys Ser Asn
1               5                   10                  15

<210> SEQ ID NO 88
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 88

His Asn Ser His Asp Pro Ser Tyr Phe Ala Cys Leu Ile Lys Glu
1               5                   10                  15

<210> SEQ ID NO 89
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 89

Val Lys His Phe Thr Asn Pro Tyr Cys Asn Ile Tyr Leu Asn Ser
1               5                   10                  15

<210> SEQ ID NO 90
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 90
```

```
Gly Trp Trp Arg Gly Glu Ile Tyr Gly Arg Val Gly Trp Phe Pro
1               5                   10                  15

<210> SEQ ID NO 91
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 91

Glu Leu Pro Asp Gly Thr Phe Tyr Ser Thr Leu Tyr Leu Pro Ile
1               5                   10                  15

<210> SEQ ID NO 92
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 92

Glu Gly Gly Glu Asp Pro Leu Tyr Val Ala Arg Arg Leu Val Arg
1               5                   10                  15

<210> SEQ ID NO 93
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 93

Leu Thr Gln Ala Val Ala Ala Tyr Gln Gly Cys His Phe Met Gly
1               5                   10                  15

<210> SEQ ID NO 94
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 94

Ala Glu Asp Phe Leu Lys Asp Tyr Ile His Ile Asn Ile Gly Ala
1               5                   10                  15

<210> SEQ ID NO 95
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 95
```

```
Ile Gly Ala Gly Lys Gly Lys Tyr Tyr Ala Val Asn Tyr Pro Leu
1               5                   10                  15

<210> SEQ ID NO 96
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 96

Glu Asn Lys Leu Asp Thr Lys Tyr Pro Tyr Val Cys His Ala Glu
1               5                   10                  15

<210> SEQ ID NO 97
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 97

Ile Thr Leu Gln Gln Ala Glu Tyr Glu Phe Leu Ser Phe Val Arg
1               5                   10                  15

<210> SEQ ID NO 98
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 98

Arg Arg Trp Tyr Pro Glu Glu Tyr Glu Phe Ala Pro Lys Lys Ala
1               5                   10                  15

<210> SEQ ID NO 99
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 99

Gln Gln Asn Gly Gln Thr Ile Tyr Leu Arg Gly Thr Gly Asp Phe
1               5                   10                  15

<210> SEQ ID NO 100
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 100
```

```
Gln Lys Ile Val Asp Asn Gly Tyr Gly Tyr Val Ser Asn Gly Ser
1               5                   10                  15

<210> SEQ ID NO 101
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 101

Tyr Gly Arg Leu Asn Leu His Tyr Ala Val Val Ser Lys Arg Lys
1               5                   10                  15

<210> SEQ ID NO 102
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 102

Ala Lys Ser Pro Asp Glu Ala Tyr Ala Ile Ala Lys Lys Leu Gly
1               5                   10                  15

<210> SEQ ID NO 103
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 103

Asn Val Thr Cys Thr Arg Ile Tyr Glu Lys Val Glu
1               5                   10

<210> SEQ ID NO 104
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 104

Asp Leu Ile Asn Arg Met Asp Tyr Val Glu Ile Asn Ile Asp His
1               5                   10                  15

<210> SEQ ID NO 105
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 105
```

```
Tyr Ala Thr Arg Glu Gly Asp Tyr Val Leu Phe His His Glu Gly
1               5                   10                  15
```

<210> SEQ ID NO 106
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 106

```
Ser Arg Thr Thr Asp Gly Val Tyr Glu Gly Val Ala Ile Gly Gly
1               5                   10                  15
```

<210> SEQ ID NO 107
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 107

```
Phe Ala Ser Ser Gln Glu Thr Tyr Gly Lys Ser Pro Phe Trp Ile
1               5                   10                  15
```

<210> SEQ ID NO 108
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 108

```
Leu Lys Asp Pro Val Gly Val Tyr Cys Arg Val Arg Pro Leu Gly
1               5                   10                  15
```

<210> SEQ ID NO 109
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 109

```
Ala Ala Gly Ala Val Ala Ser Tyr Asp Tyr Leu Val Ile Gly Gly
1               5                   10                  15
```

<210> SEQ ID NO 110
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 110

```
Leu Val Ser Arg Leu Thr Leu Tyr Asp Ile Ala His Thr Pro Gly
1               5                   10                  15

<210> SEQ ID NO 111
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 111

Pro Glu Asp Leu Pro Lys Ser Tyr Asp Tyr Asp Leu Ile Ile Ile
1               5                   10                  15

<210> SEQ ID NO 112
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 112

Asp Leu Pro Lys Ser Tyr Asp Tyr Asp Leu Ile Ile Ile Gly Gly
1               5                   10                  15

<210> SEQ ID NO 113
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 113

Lys Val Val Tyr Glu Asn Ala Tyr Gly Gln Phe Ile Gly Pro His
1               5                   10                  15

<210> SEQ ID NO 114
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 114

Ser Arg Asp Asn Asn Lys Cys Tyr Ala Lys Ile Ile Cys Asn Thr
1               5                   10                  15

<210> SEQ ID NO 115
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 115
```

-continued

```
Val Leu Gln Arg Thr Leu His Tyr Glu Cys Ile Val Leu Val Lys
1               5                   10                  15
```

<210> SEQ ID NO 116
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 116

```
Asp Gly Gly Ser Asp Gln Asn Tyr Asp Ile Val Thr Ile Gly Ala
1               5                   10                  15
```

<210> SEQ ID NO 117
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 117

```
Asp Gly Gln Glu Ala Pro Ile Tyr Glu Leu Thr Ser Gln Phe Thr
1               5                   10                  15
```

<210> SEQ ID NO 118
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 118

```
Gly Lys Leu Val Gln Ile Glu Tyr Ala Leu Ala Ala Val Ala Gly
1               5                   10                  15
```

<210> SEQ ID NO 119
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 119

```
Arg Lys Leu Ala Gln Gln Tyr Tyr Leu Val Tyr Gln Glu Pro Ile
1               5                   10                  15
```

<210> SEQ ID NO 120
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 120

```
Pro Ser Gly Val Ser Tyr Gly Tyr Trp Gly Cys Ala Ile Gly Lys
1               5                   10                  15
```

<210> SEQ ID NO 121
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 121

```
Met Leu Gly Ala Ser Gly Asp Tyr Ala Asp Phe Gln Tyr Leu Lys
1               5                   10                  15
```

<210> SEQ ID NO 122
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 122

```
Val Asp Thr Ala Glu Gln Val Tyr Ile Ser Ser Leu Ala Leu Leu
1               5                   10                  15
```

<210> SEQ ID NO 123
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 123

```
Asp Val Thr Gly Pro His Leu Tyr Ser Ile Tyr Pro His Gly Ser
1               5                   10                  15
```

<210> SEQ ID NO 124
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 124

```
Glu Leu Thr Ala Glu Phe Leu Tyr Asp Glu Val His Pro Lys Gln
1               5                   10                  15
```

<210> SEQ ID NO 125
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 125

-continued

```
Glu Leu Thr Ala Asp Phe Leu Tyr Glu Glu Val His Pro Lys Gln
1               5                   10                  15

<210> SEQ ID NO 126
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 126

Asp Gly Tyr Asp Asp Asp Asn Tyr Asp Tyr Ile Val Lys Asn Gly
1               5                   10                  15

<210> SEQ ID NO 127
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 127

Arg Asp His Leu Ala Tyr Arg Tyr Glu Val Leu Lys Ile Ile Gly
1               5                   10                  15

<210> SEQ ID NO 128
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 128

Glu Gly Thr Tyr Gly Val Val Tyr Lys Gly Arg His Lys Thr Thr
1               5                   10                  15

<210> SEQ ID NO 129
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 129

Arg Gly Glu Pro Asn Val Ser Tyr Ile Cys Ser Arg Tyr Tyr Arg
1               5                   10                  15

<210> SEQ ID NO 130
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 130
```

Ser Lys Ala Val Cys Ser Thr Tyr Leu Gln Ser Arg Tyr Tyr Arg
1               5                   10                  15

<210> SEQ ID NO 131
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 131

Ser Lys Thr Val Cys Ser Thr Tyr Leu Gln Ser Arg Tyr Tyr Arg
1               5                   10                  15

<210> SEQ ID NO 132
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 132

Ala Asp Asn Asp Ile Thr Pro Tyr Leu Val Ser Arg Phe Tyr Arg
1               5                   10                  15

<210> SEQ ID NO 133
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 133

Ala Thr Gln Pro Glu Pro Ile Tyr Ala Glu Ser Thr Lys Arg Lys
1               5                   10                  15

<210> SEQ ID NO 134
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 134

Gly Gly Val Lys Lys Pro Thr Tyr Asp Pro Val Ser Glu Asp Gln
1               5                   10                  15

<210> SEQ ID NO 135
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 135

```
Asn Ser Leu Ile Ser Ser Asp Tyr Glu Leu Leu Ser Asp Pro Thr
1               5                   10                  15

<210> SEQ ID NO 136
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 136

Lys Ile Gln Asn Thr Gly Asp Tyr Tyr Asp Leu Tyr Gly Gly Glu
1               5                   10                  15

<210> SEQ ID NO 137
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; ; tyrosine at position 8 is
      phosphorylatable

<400> SEQUENCE: 137

Gln Pro Leu Thr Glu Ala Ser Tyr Val Asn Leu Pro Thr Ile Ala
1               5                   10                  15

<210> SEQ ID NO 138
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 138

Met Glu Leu Gln Ser Pro Glu Tyr Lys Leu Ser Lys Leu Arg Thr
1               5                   10                  15

<210> SEQ ID NO 139
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 139

Thr Ser Thr Ile Met Thr Asp Tyr Asn Pro Asn Tyr Cys Phe Ala
1               5                   10                  15

<210> SEQ ID NO 140
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 140
```

-continued

```
His Gly Ala Phe Gly Glu Val Tyr Glu Gly Gln Val Ser Gly Met
1               5                   10                  15

<210> SEQ ID NO 141
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 141

Phe Gly Met Ala Arg Asp Ile Tyr Arg Ala Ser Tyr Tyr Arg Lys
1               5                   10                  15

<210> SEQ ID NO 142
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 142

Arg Asp Ile Tyr Arg Ala Ser Tyr Tyr Arg Lys Gly Gly Cys Ala
1               5                   10                  15

<210> SEQ ID NO 143
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 143

Phe Pro Cys Gly Asn Val Asn Tyr Gly Tyr Gln Gln Gln Gly Leu
1               5                   10                  15

<210> SEQ ID NO 144
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 144

Arg Ala Thr Glu Asn Asp Ile Tyr Asn Phe Phe Ser Pro Leu Asn
1               5                   10                  15

<210> SEQ ID NO 145
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 145
```

```
Pro Tyr Gly Gly Gly Gln Tyr Phe Ala Lys Pro Arg Asn Gln
1               5                   10                  15
```

<210> SEQ ID NO 146
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 146

```
Thr Leu His Ser Val Asp Gln Tyr Leu Asn Ile Lys Leu Thr Asp
1               5                   10                  15
```

<210> SEQ ID NO 147
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 147

```
Leu Glu Arg Thr Ile Asn Leu Tyr Pro Leu Thr Asn Tyr Thr Phe
1               5                   10                  15
```

<210> SEQ ID NO 148
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 148

```
Val Phe Asn His Thr Glu Asp Tyr Val Leu Leu Pro Asp Glu Arg
1               5                   10                  15
```

<210> SEQ ID NO 149
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 149

```
Phe Ile Ile Arg Ile Pro Pro Tyr His Tyr Ile His Val Leu Asp
1               5                   10                  15
```

<210> SEQ ID NO 150
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 150

-continued

Ile Val Ala Thr Lys Pro Leu Tyr Val Ala Leu Ala Gln Arg Lys
1               5                   10                  15

<210> SEQ ID NO 151
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 151

Ile Thr Arg Arg Ser Leu Gly Tyr Ala Tyr Val Asn Phe Gln Gln
1               5                   10                  15

<210> SEQ ID NO 152
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 152

Asp Glu Asn Gly Ser Lys Gly Tyr Ala Phe Val His Phe Glu Thr
1               5                   10                  15

<210> SEQ ID NO 153
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 153

His Pro His Leu Ser Lys Gly Tyr Ala Tyr Val Glu Phe Glu Asn
1               5                   10                  15

<210> SEQ ID NO 154
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 154

Val Pro Asp Tyr Pro Pro Asn Tyr Ile Leu Phe Leu Asn Asn Leu
1               5                   10                  15

<210> SEQ ID NO 155
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 155

Ser His Glu Gly Glu Thr Ala Tyr Ile Arg Val Lys Val Asp Gly
1               5                   10                  15

<210> SEQ ID NO 156
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 156

Ala Gly Lys Gln Lys Leu Gln Tyr Glu Gly Ile Phe Ile Lys Asp
1               5                   10                  15

<210> SEQ ID NO 157
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 157

Asn Cys Glu Ile Cys Gly Asn Tyr Thr Tyr Arg Gly Pro Lys Ala
1               5                   10                  15

<210> SEQ ID NO 158
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 158

Val Thr Gly Gln His Gln Gly Tyr Gly Phe Val Glu Phe Leu Ser
1               5                   10                  15

<210> SEQ ID NO 159
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 159

Gly Phe Asn Val Cys Asn Arg Tyr Leu Val Val Leu Tyr Tyr Asn
1               5                   10                  15

<210> SEQ ID NO 160
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 160

Arg Asp Ala Asp Asp Ala Val Tyr Glu Leu Asn Gly Lys Asp Leu
1               5                   10                  15

<210> SEQ ID NO 161
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 161

Glu His Thr Ser Asn Asp Pro Tyr Cys Phe Val Glu Phe Tyr Glu
1               5                   10                  15

<210> SEQ ID NO 162
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 162

Tyr Gln Arg Leu Gly Leu Asp Tyr Glu Glu Arg Val Leu Pro Ser
1               5                   10                  15

<210> SEQ ID NO 163
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 163

Tyr Phe Pro Ile Pro Glu Glu Tyr Thr Phe Ile Gln Asn Val Pro
1               5                   10                  15

<210> SEQ ID NO 164
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 164

Arg Asn Ala Arg Leu Ser Ile Tyr Gly Ile Trp Phe Tyr Asp Lys
1               5                   10                  15

<210> SEQ ID NO 165
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 165

```
Leu Met Lys Asn Leu Thr Gln Tyr Glu Gln Leu Lys Ala His Gln
1               5                   10                  15
```

<210> SEQ ID NO 166
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 166

```
Ile Thr Ser Ser Ser Ala Ile Tyr Asp Asn Pro Asn Leu Ile Lys
1               5                   10                  15
```

<210> SEQ ID NO 167
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 167

```
Ala Glu Asp Phe Leu Lys Asp Tyr Ile His Ile Asn Ile Gly Ala
1               5                   10                  15
```

<210> SEQ ID NO 168
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 168

```
Phe Ala Ser Ser Gln Glu Thr Tyr Gly Lys Ser Pro Phe Trp Ile
1               5                   10                  15
```

<210> SEQ ID NO 169
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 169

```
Asp Leu Ile Asn Arg Met Asp Tyr Val Glu Ile Asn Ile Asp His
1               5                   10                  15
```

<210> SEQ ID NO 170
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 170

Arg Asn Glu Glu Glu Asn Ile Tyr Ser Val Pro His Asp Ser Thr
1               5                   10                  15

<210> SEQ ID NO 171
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 171

Ile His Thr Gly Glu Asn Leu Tyr Lys Cys Lys Val Cys Ala Lys
1               5                   10                  15

<210> SEQ ID NO 172
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 172

Ser Thr Ser Ser Asp Thr Thr Tyr Lys Gly Gly Ala Ser Glu Lys
1               5                   10                  15

<210> SEQ ID NO 173
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 173

Asn Ser Lys Phe Asp Thr Ile Tyr Gln Ile Leu Leu Lys Lys Lys
1               5                   10                  15

<210> SEQ ID NO 174
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 174

Ile His Thr Gly Glu Lys Pro Tyr Gln Cys Gly Gln Cys Gly Lys
1               5                   10                  15

<210> SEQ ID NO 175
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 175

```
Ile His Ser Gly Glu Lys Pro Tyr Gly Cys Val Glu Cys Gly Lys
1               5                   10                  15
```

<210> SEQ ID NO 176
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 176

```
Ile His Thr Gly Glu Lys Pro Tyr Glu Cys Val Gln Cys Gly Lys
1               5                   10                  15
```

<210> SEQ ID NO 177
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 177

```
Ile His Ser Gly Val Lys Pro Tyr Glu Cys Thr Glu Cys Gly Lys
1               5                   10                  15
```

<210> SEQ ID NO 178
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 178

```
Val His Ser Gly Glu Asn Pro Tyr Glu Cys Leu Glu Cys Gly Lys
1               5                   10                  15
```

<210> SEQ ID NO 179
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 179

```
Ile His Thr Gly Glu Lys Pro Tyr Glu Cys Val Glu Cys Gly Lys
1               5                   10                  15
```

<210> SEQ ID NO 180
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 180

```
Ile His Ser Gly Glu Lys Pro Tyr Glu Cys Val Glu Cys Gly Lys
1               5                   10                  15
```

<210> SEQ ID NO 181
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 181

```
Leu Pro Ala Gly Thr Glu Asp Tyr Ile His Ile Arg Ile Gln Gln
1               5                   10                  15
```

<210> SEQ ID NO 182
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 182

```
Lys Asn Met Ser Gly Ser Leu Tyr Glu Met Val Ser Arg Val Met
1               5                   10                  15
```

<210> SEQ ID NO 183
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 183

```
Lys Thr Pro Gln Gly Arg Glu Tyr Gly Met Ile Tyr Leu Gly Lys
1               5                   10                  15
```

<210> SEQ ID NO 184
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 184

```
His Asn Ile Val Phe Gly Asp Tyr Thr Trp Thr Glu Phe Asp Glu
1               5                   10                  15
```

<210> SEQ ID NO 185
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 185

Lys Asn Met Ser Gly Ser Leu Tyr Glu Met Val Ser Arg Val Met
1               5                   10                  15

<210> SEQ ID NO 186
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 186

Asn Pro Pro Ser Gln Gly Asp Tyr His Gly Cys Pro Phe Arg His
1               5                   10                  15

<210> SEQ ID NO 187
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 187

Asn Lys Leu Val Asp Gly Cys Tyr Ser Phe Trp Gln Ala Gly Leu
1               5                   10                  15

<210> SEQ ID NO 188
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 188

Arg Glu Gly Asp Asn Val Asn Tyr Asp Trp Ile His Trp Asp Pro
1               5                   10                  15

<210> SEQ ID NO 189
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 189

Val Tyr Asp Glu Asp Ser Pro Tyr Gln Asn Ile Lys Ile Leu His
1               5                   10                  15

<210> SEQ ID NO 190
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 190

```
Glu Gln Ile Ile Gln Glu Ile Tyr Ser Gln Ile Gln Ser Lys Lys
1               5                   10                  15
```

<210> SEQ ID NO 191
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 191

```
Arg Glu His Ala Leu Leu Ala Tyr Thr Leu Gly Val Lys Gln Leu
1               5                   10                  15
```

<210> SEQ ID NO 192
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 192

```
Ser Ser Gly Gly Glu Asp Gly Tyr Val Arg Ile His Tyr Phe Asp
1               5                   10                  15
```

<210> SEQ ID NO 193
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 193

```
His Trp Gln Lys Asn Gly Asp Tyr Leu Cys Val Lys Val Asp Arg
1               5                   10                  15
```

<210> SEQ ID NO 194
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 194

```
Asn Leu Ala Met Glu Ala Thr Tyr Ile Asn His Asn Phe Ser Gln
1               5                   10                  15
```

<210> SEQ ID NO 195
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 195

-continued

Asn Val Thr Thr Cys Asn Asp Tyr Val Ala Leu Val His Pro Asp
1               5                   10                  15

<210> SEQ ID NO 196
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 196

Pro Asn Glu Ile Lys Val Val Tyr Leu Arg Cys Thr Gly Gly Glu
1               5                   10                  15

<210> SEQ ID NO 197
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 197

Lys Ser Ser Gly Glu Ile Val Tyr Cys Gly Gln Val Phe Glu Lys
1               5                   10                  15

<210> SEQ ID NO 198
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 198

Asn Thr Gly Ala Lys Asn Leu Tyr Ile Ile Ser Val Lys Gly Ile
1               5                   10                  15

<210> SEQ ID NO 199
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 199

Glu Asp Ser Pro Asn Lys Leu Tyr Thr Leu Val Thr Tyr Val Pro
1               5                   10                  15

<210> SEQ ID NO 200
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 200

-continued

```
Lys Leu Tyr Thr Leu Val Thr Tyr Val Pro Val Thr Thr Phe Lys
1               5                   10                  15
```

<210> SEQ ID NO 201
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 201

```
Met Leu Arg Ile Val Glu Pro Tyr Ile Ala Trp Gly Tyr Pro Asn
1               5                   10                  15
```

<210> SEQ ID NO 202
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 202

```
Glu Asp Leu Ile His Glu Ile Tyr Thr Val Gly Lys Arg Phe Lys
1               5                   10                  15
```

<210> SEQ ID NO 203
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 203

```
Leu Ala Arg Ala Ser Gly Asn Tyr Ala Thr Val Ile Ser His Asn
1               5                   10                  15
```

<210> SEQ ID NO 204
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 204

```
Ile Ile Gln Leu Leu Asp Asp Tyr Pro Lys Cys Phe Ile Val Gly
1               5                   10                  15
```

<210> SEQ ID NO 205
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 205

```
Lys Lys Asn Arg Ile Ala Ile Tyr Glu Leu Leu Phe Lys Glu Gly
1               5                   10                  15
```

<210> SEQ ID NO 206
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 206

```
Asp Asp Val Lys Glu Gln Ile Tyr Lys Leu Ala Lys Lys Gly Leu
1               5                   10                  15
```

<210> SEQ ID NO 207
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 207

```
Leu Leu Lys Val Leu Tyr Gln Tyr Lys Glu Lys Gln Tyr Met Ala
1               5                   10                  15
```

<210> SEQ ID NO 208
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 208

```
Asp Leu Ile Asn Arg Met Asp Tyr Val Glu Ile Asn Ile Asp His
1               5                   10                  15
```

<210> SEQ ID NO 209
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 209

```
Lys Cys Ser Val Cys Pro Asp Tyr Asp Leu Cys Ser Val Cys Glu
1               5                   10                  15
```

<210> SEQ ID NO 210
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 210

```
Thr His Arg Gln Gly His Ile Tyr Met Glu Met Asn Phe Thr Asn
1               5                   10                  15

<210> SEQ ID NO 211
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; tyrosine at position 8 is
      phosphorylatable

<400> SEQUENCE: 211

Val Asp Thr Cys Arg Gly His Tyr Asn Asn Val Ser Cys Ala Val
1               5                   10                  15
```

US 7,973,134 B2

REAGENTS FOR THE DETECTION OF PROTEIN PHOSPHORYLATION IN ANAPLASTIC LARGE CELL LYMPHOMA SIGNALING PATHWAYS

RELATED APPLICATIONS

This application claims the priority benefit of U.S. Ser. No. 10/777,893, filed Feb. 12, 2004 (now U.S. Pat. No. 7,300,753), and PCT/US04/21670 filed Jul. 7, 2004.

FIELD OF THE INVENTION

The invention relates generally to antibodies and peptide reagents for the detection of protein phosphorylation, and to protein phosphorylation in cancer.

BACKGROUND OF THE INVENTION

The activation of proteins by post-translational modification represents an important cellular mechanism for regulating most aspects of biological organization and control, including growth, development, homeostasis, and cellular communication. For example, protein phosphorylation plays a critical role in the etiology of many pathological conditions and diseases, including cancer, developmental disorders, autoimmune diseases, and diabetes. In spite of the importance of protein modification, it is not yet well understood at the molecular level. The reasons for this lack of understanding are, first, that the cellular modification system is extraordinarily complex, and second, that the technology necessary to unravel its complexity has not yet been fully developed.

The complexity of protein modification, including phosphorylation, on a proteome-wide scale derives from three factors: the large number of modifying proteins, e.g. kinases, encoded in the genome, the much larger number of sites on substrate proteins that are modified by these enzymes, and the dynamic nature of protein expression during growth, development, disease states, and aging. The human genome encodes, for example, over 520 different protein kinases, making them the most abundant class of enzymes known. See Hunter, Nature 411: 355-65 (2001). Each of these kinases phosphorylates specific serine, threonine, or tyrosine residues located within distinct amino acid sequences, or motifs, contained within different protein substrates. Most kinases phosphorylate many different proteins: it is estimated that one-third of all proteins encoded by the human genome are phosphorylated, and many are phosphorylated at multiple sites by different kinases. See Graves et al., Pharmacol. Ther. 82:111-21 (1999).

Many of these phosphorylation sites regulate critical biological processes and may prove to be important diagnostic or therapeutic targets for molecular medicine. For example, of the more than 100 dominant oncogenes identified to date, 46 are protein kinases. See Hunter, supra. Oncogenic kinases such as ErbB2 and Jak3, widely expressed in breast tumors and various leukemias, respectively, transform cells to the oncogenic phenotype at least in part because of their ability to phosphorylate cellular proteins. Understanding which proteins are modified by these kinases will greatly expand our understanding of the molecular mechanisms underlying oncogenic transformation. Thus, the ability to identify modification sites, e.g. phosphorylation sites, on a wide variety of cellular proteins is crucially important to understanding the key signaling proteins and pathways implicated in disease progression, for example cancer.

The efficient identification of protein phosphorylation sites relevant to disease has been aided by the recent development of a powerful new class of antibodies, called motif-specific, context-independent antibodies, which are capable of specifically binding short, recurring signaling motifs comprising one or more modified (e.g. phosphorylated) amino acids in many different proteins in which the motif recurs. See U.S. Pat. No. 6,441,140, Comb et al. Many of these powerful new antibodies are now available commercially. See CELL SIGNALING TECHNOLOGY, INC. 2003-04 Catalogue. More recently, a powerful new method for employing such motif-specific antibodies in immunoaffinity techniques coupled with mass spectrometric analysis to rapidly identify modified peptides from complex biological mixtures has been described. See U.S. Patent Publication No. 20030044848, Rush et al.). Such techniques will enable the rapid elucidation of protein activation and phosphorylation events underlying diseases, like cancer, that are driven by disruptions in signal transduction.

One form of cancer, in which underlying signal transduction events are involve but still poorly understood, is Anaplastic Large-Cell Lymphoma (ALCL). ALCL is a sub-type of non-Hodgkin's lymphomas (NHL), which are the 5$^{th}$ most common cancer in the United States, with over 53,000 new diagnoses annually (source: The Leukemia & Lymphoma Society (2004)). Worldwide, more than 166,000 cases of NHL are diagnosed annually, and over 93,000 annual deaths from this group of lymphomas (source: Globocan 2000: Cancer Incidence, Mortality & Prevalence, Version 1.0 (2001)). ALCL, a form of T-cell lymphoma (CD30+), is most prevalent among young children, representing about 15% of all pediatric non-Hodgkin's lymphomas (source: UMDNJ Hematopathology (2004)). It is an aggressive disease that can be either systemic or primary cutaneous, with median survival rates of about 5 years from diagnosis.

Approximately 50% to 60% of all ALCL cases are characterized by a translocation between chromosomes 2p23 and 5q35 leading to an abnormal fusion gene involving the anaplastic lymphoma kinase (ALK) gene and the nucleophosmin gene (NPM), itself involved in nucleo-cytoplasmic trafficking. See, e.g. Ouyang et al., J. Biol. Chem. 278: 300028-300036 (2003); Miller, ProPath "Anaplastic Lymphoma Kinase" (2003). The ALK-NPM fusion protein functions as a constitutively activated protein tyrosine kinase, leading to enhanced cellular proliferation and survival. It has recently been shown that ALK-NPM transgenic mice spontaneously develop T-cell lymphomas including ALCL. See Chiarle et al., Blood 101: 1919-1927 (2003).

A number of downstream signaling protein targets of ALK-NPM have identified as potentially involved in mediating cellular transformation in ALK-NPM positive ALCL, including Shc, IRS-1, Grb2, phospholipase C-γ, P13-kinase, and Stat3/5. See Ouyang et al. supra; Zamo et al., Oncogene 21: 1038-1047 (2002). ALK-NPM activates the AKT/PI3K anti-apoptotic signaling pathway. Transgenic mice experiments have established that Stat3 and Jak3 are constitutively activated in ALK-NPM positive transgenic mice that develop ALCL. See Chiarle et al., supra. However, despite the identification of some of the downstream targets of ALK-NPM, the molecular mechanisms of contributing to ALK-NPM-mediated oncogenesis in ALCL remain incompletely understood. See Ouyang et al., supra.

A few phosphotyrosine sites that allow NPM-ALK to interact with other signaling proteins have been reported, including Tyr1604, which is a binding site for phospholipase gamma (PLCgamma) (see Bai et al. Mol. Cell. Biol. 18: 6951-6961 (1998), and Tyr1096 and Tyr1507, which are the docking sites for SHC and IRS-1 respectively. See Fujimoto et al., *PNAS* 93: 4181-4186 (1996). PLCgamma, SHC and IRS-1 are known to be phosphorylated in the context of other signaling cascades and many of their phosphorylation sites have been identified. See Watanabe et al., *J. Biol. Chem.* 276: 38595-38601 (2001); Law et al., *Mol Cell Biol* 16: 1305-1315 (1996); van der Geer et al., *Curr. Biol.* 6: 1432-1444 (1996); White M F, *Mol. Cell. Biochem.* 182: 3-11 (1998). Another important factor directly phosphorylated by NPM-ALK fusion kinase is STAT3. Phosphorylation of STAT3 at Tyr705 has been shown to be important for oncogenic transformation. See Zamo A. et al. *Oncogene* 21: 1038-1047 (2002).

Nonetheless, the small number of ALCL-related phosphorylation sites that have been identified to date do not facilitate a complete and accurate understanding of how protein activation within ALK-NPM signaling pathways is driving this disease.

Accordingly, there is a continuing need to unravel the molecular mechanisms of ALK-NPM driven oncogenesis in ALCL, by identifying the downstream signaling proteins mediating cellular transformation in this disease. Identifying particular phosphorylation sites on such signaling proteins and providing new reagents, such as phospho-specific antibodies and AQUA peptides, to detect and quantify them remains particularly important to advancing our understanding of the biology of this disease.

Presently, diagnosis of ALCL is made by tissue biopsy and detection of T-cell markers, such as CD30 and/or CD4. However, mis-diagnosis can occur since some ALCL can be negative for certain markers and/or can be positive for keratin, a marker for carcinoma. Although the ALK-NPM genetic translocation itself can be detected, it is clear that other downstream effectors of ALCL, having diagnostic, predictive, or therapeutic value, remain to be elucidated. Accordingly, identification of downstream signaling molecules and phosphosites involved in ALK-NPM positive ALCL and development of new reagents to detect and quantify these sites and proteins may lead to improved diagnostic/prognostic markers, as well as novel drug targets, for the detection and treatment of this disease.

SUMMARY OF THE INVENTION

The invention discloses 211 novel phosphorylation sites identified in signal transduction proteins and pathways underlying Anaplastic Large Cell Lymphoma (ALCL) involving the ALK-NPM translocation/fusion, and provides new reagents, including phosphorylation-site specific antibodies and AQUA peptides, for the selective detection and quantification of these phosphorylated sites/proteins. Also provided are methods of using the reagents of the invention for the detection and quantification of the disclosed phosphorylation sites.

BRIEF DESCRIPTION OF THE DRAWINGS

This patent or application file contains at least one drawing executed in color. Copies of this patent or patent application publication with color drawing(s) will be provided by the United States Patent Office upon request and payment of the necessary fee.

FIG. 2—Is a table (corresponding to Table 1) enumerating the ALCL signaling protein phosphorylation sites disclosed herein: Column A=the abbreviated name of the parent protein; Column B=the full name of the parent protein; Column C=the SwissProt accession number for the protein (human sequence); Column D=the protein type/classification; Column F=the residue (in the parent protein amino acid sequence) at which phosphorylation occurs within the phosphorylation site; Column G=the phosphorylation site sequence encompassing the phosphorylatable residue; (residue at which phosphorylation occurs (and corresponding to the respective entry in Column F) appears in lowercase; and Column I=the ALCL cell line in which the phosphorylation site was discovered.

DETAILED DESCRIPTION OF THE INVENTION

Figure 1:
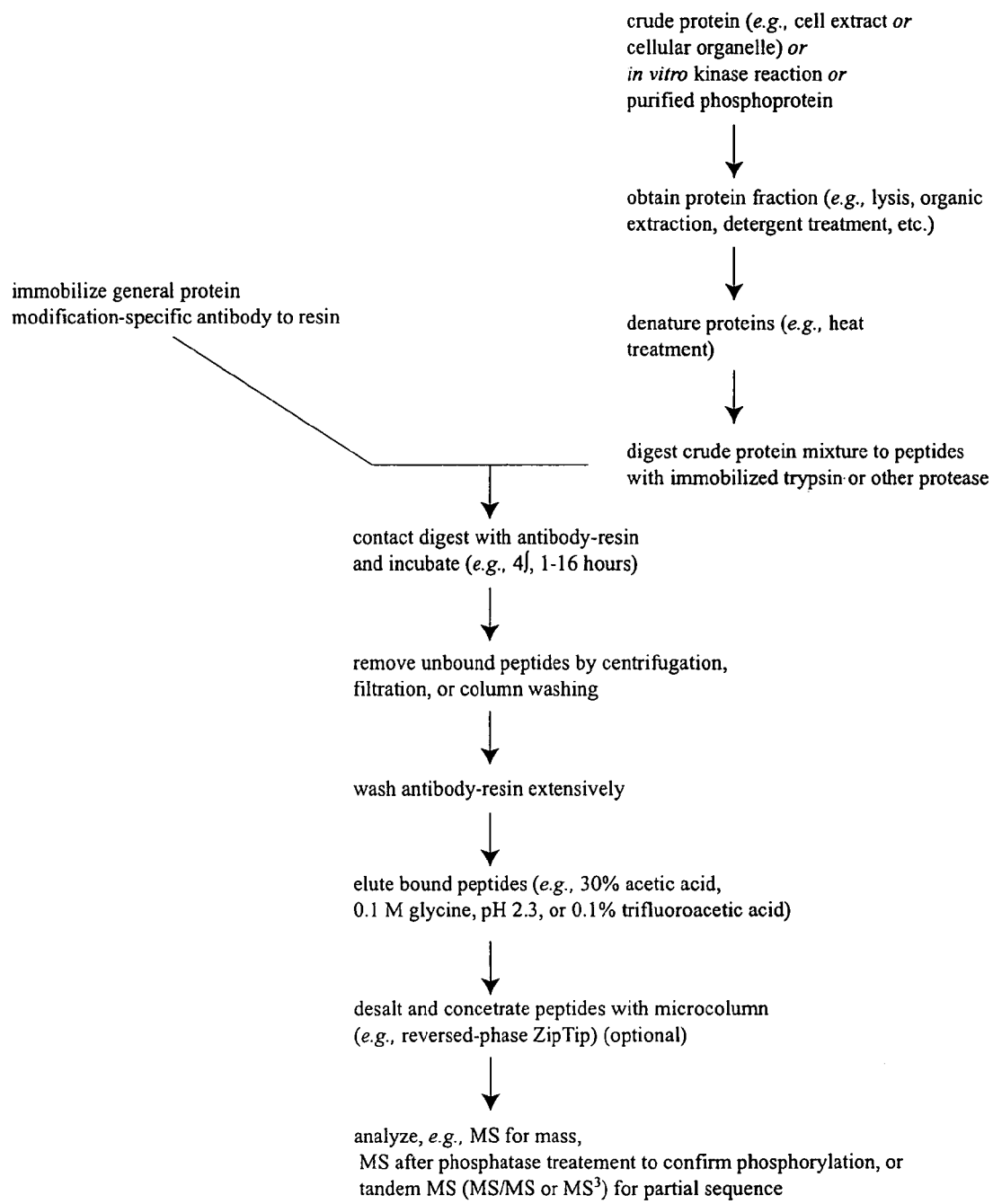
FIG. 1—Is a diagram broadly depicting the immunoaffinity isolation and mass-spectrometric characterization methodology (IAP) employed to identify the novel phosphorylation sites disclosed herein.
Figure 3:
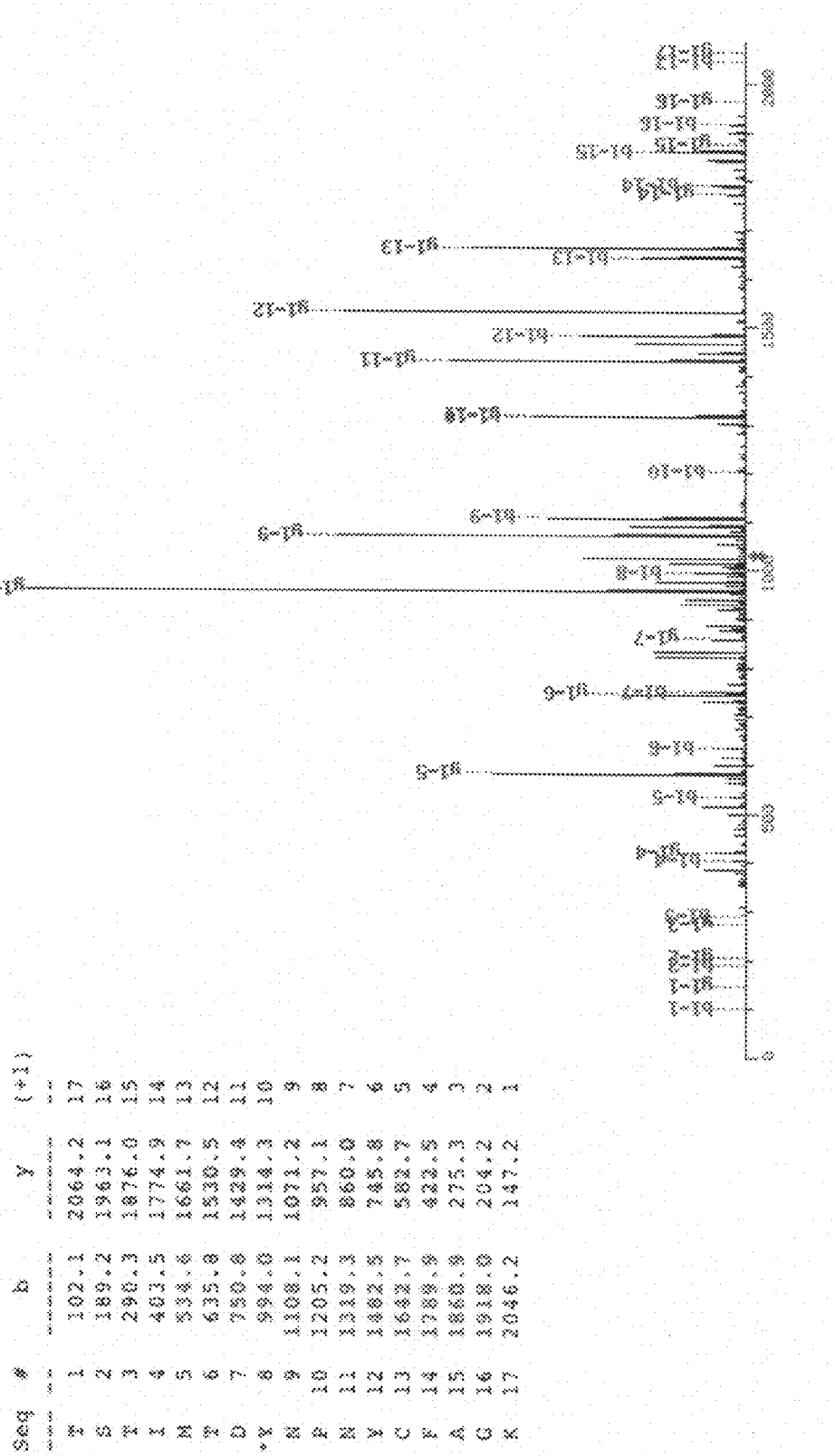
FIG. 3—is an exemplary mass spectrograph depicting the detection of the tyrosine 1092 phosphorylation site in ALK (see Row 140 in FIG. 2/Table 1), as further described in Example 1 (red and blue indicate ions detected in MS/MS spectrum).
Figure 4:
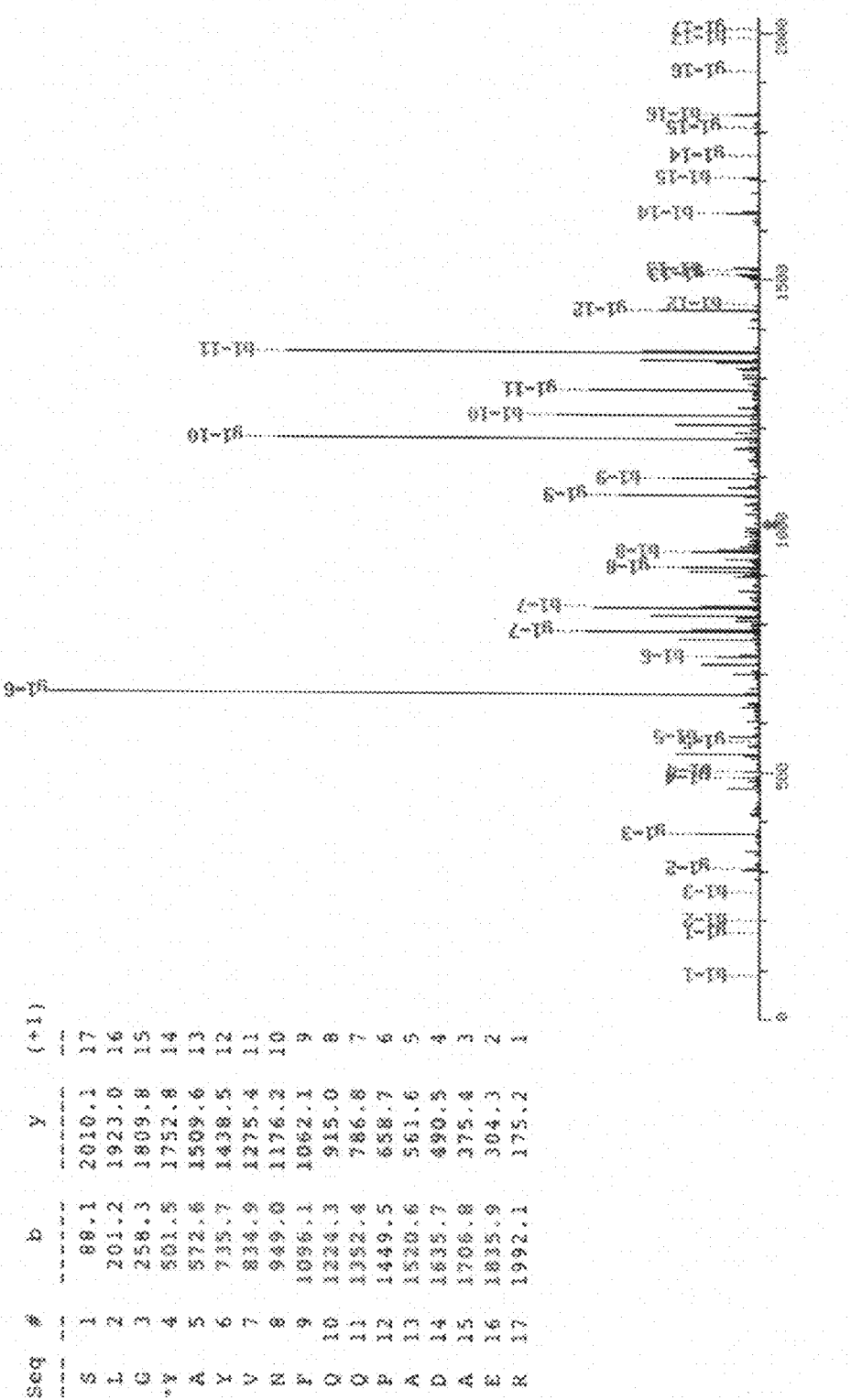
FIG. 4—is an exemplary mass spectrograph depicting the detection of the tyrosine 54 phosphorylation site in PABP1 (see Row 152 in FIG. 2/Table 1), as further described in Example 1 (red and blue indicate ions detected in MS/MS spectrum).
Figure 5:
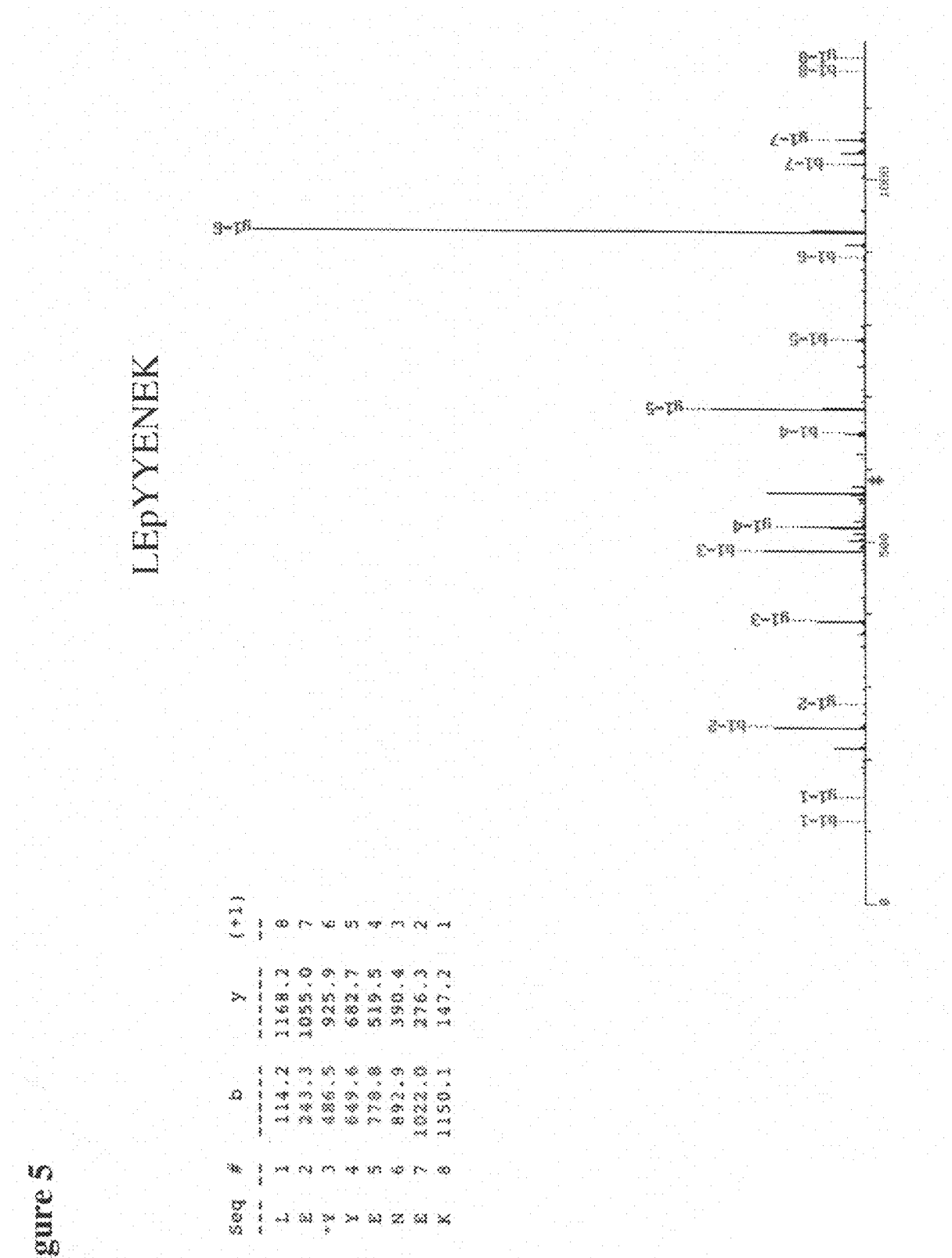
FIG. 5—is an exemplary mass spectrograph depicting the detection of the tyrosine 46 phosphorylation site in IRS1 (see Row 17 in FIG. 2/Table 1), as further described in Example 1 (red and blue indicate ions detected in MS/MS spectrum).
Figure 6:
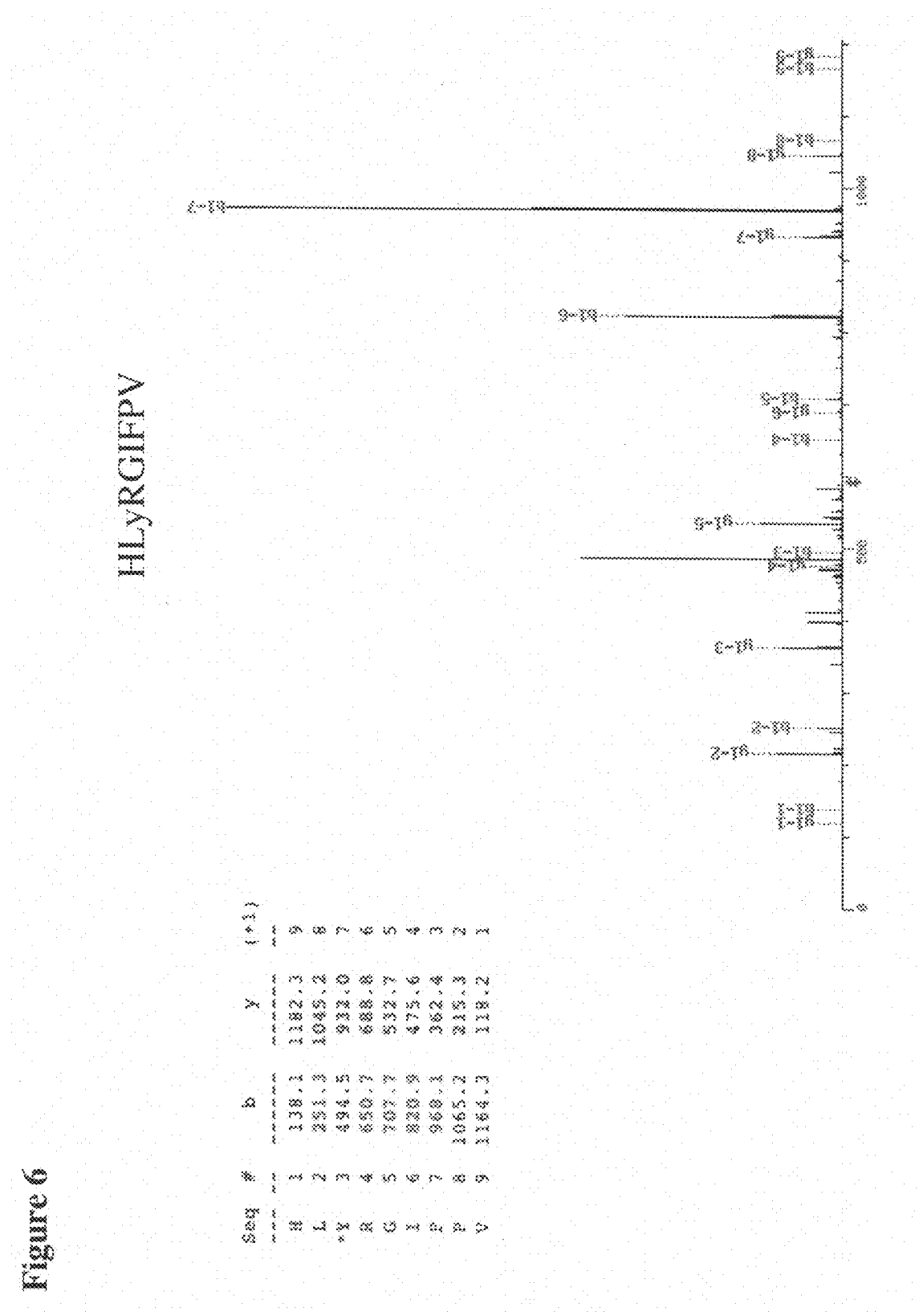
FIG. 6—is an exemplary mass spectrograph depicting the detection of the tyrosine 465 phosphorylation site in PKM (see Row 78 in FIG. 2/Table 1), as further described in Example 1 (red and blue indicate ions detected in MS/MS spectrum).

In accordance with the present invention, 211 novel protein phosphorylation sites in signaling pathways underlying ALK-NPM positive Anaplastic Large Cell Lymphoma (ALCL) oncogenesis have now been discovered. These newly described phosphorylation sites were identified by employing the techniques described in "Immunoaffinity Isolation of Modified Peptides From Complex Mixtures," U.S. Patent Publication No. 20030044848, Rush et al., using cellular extracts from two recognized ALCL cell lines, as further described below. The novel phosphorylation sites, and their corresponding parent proteins, disclosed herein are listed in Table I. These phosphorylation sites correspond to numerous different parent proteins (the full sequences of which (human) are all publicly available in SwissProt database and their Accession numbers listed in Column C of Table 1/FIG. 2), each of which fall into discrete protein type groups, for example Acetyltransferases, Helicases, Protein Kinases, and Transcription Factors (see Column D of Table 1), the phosphorylation of which is relevant to signal transduction activity in ALCL as disclosed herein.

The discovery of the 211 novel protein phosphorylation sites described herein enables the production, by standard methods, of new reagents, such as phosphorylation site-specific antibodies and AQUA peptides (heavy-isotope labeled peptides), capable of specifically detecting and/or quantifying these phosphorylated sites/proteins. Such reagents are highly useful, inter alia, for studying signal transduction events underlying the progression of ALCL. Accordingly, the invention provides novel reagents—phospho-specific antibodies and AQUA peptides—for the specific detection and/or quantification of an ALCL-related signaling protein/polypeptide only when phosphorylated (or only when not phosphorylated) at a particular phosphorylation site disclosed herein. The invention also provides methods of detecting and/or quantifying one or more phosphorylated ALCL-related signaling proteins using the phosphorylation-site specific antibodies and AQUA peptides of the invention.

In part, the invention provides an isolated phosphorylation site-specific antibody that specifically binds a given ALCL-related signaling protein only when phosphorylated (or not phosphorylated, respectively) at a particular amino acid enumerated in Column F of Table 1/FIG. 2 comprised within the phosphorylatable peptide site sequence enumerated in corresponding Column G. In further part, the invention provides a heavy-isotope labeled peptide (AQUA peptide) for the quantification of a given ALCL-related signaling protein, the labeled peptide comprising a particular phosphorylatable peptide site/sequence enumerated in Column G of Table 1/FIG. 2 herein. For example, among the reagents provided by the invention is an isolated phosphorylation site-specific antibody that specifically binds the Anaplastic Lymphoma Kinase (ALK) protein only when phosphorylated (or only when not phosphorylated) at tyrosine 1078 (see Row 139 (and Columns F and G) of Table 1/FIG. 2). By way of further example, among the group of reagents provided by the invention is an AQUA peptide for the quantification of phosphorylated ALK protein, the AQUA peptide comprising the phosphorylatable peptide sequence listed in Column G, Row 139, of Table 1/FIG. 2.

In one embodiment, the invention provides an isolated phosphorylation site-specific antibody that specifically binds an Anaplastic Large Cell Lymphoma (ALCL)-related signaling protein selected from Column A of Table 1 only when phosphorylated at the tyrosine listed in corresponding Column F of Table 1, comprised within the peptide sequence listed in corresponding Column G of Table 1 (SEQ ID NOs: 1-211), wherein said antibody does not bind said signaling protein when not phosphorylated at said tyrosine. In another embodiment, the invention provides an isolated phosphorylation site-specific antibody that specifically binds an ALCL-related signaling protein selected from Column A of Table 1 only when not phosphorylated at the tyrosine listed in corresponding Column F of Table 1, comprised within the peptide sequence listed in corresponding Column G of Table 1 (SEQ ID NOs: 1-211), wherein said antibody does not bind said signaling protein when phosphorylated at said tyrosine. Such reagents enable the specific detection of phosphorylation (or non-phosphorylation) of a novel phosphorylatable site disclosed herein. The invention further provides immortalized cell lines producing such antibodies. In one preferred embodiment, the immortalized cell line is a rabbit or mouse hybridoma.

In another embodiment, the invention provides a heavy-isotope labeled peptide (AQUA peptide) for the quantification of an ALCL-related signaling protein selected from Column A of Table 1, said labeled peptide comprising the phosphorylatable peptide sequence listed in corresponding Column G of Table 1 (SEQ ID NOs: 1-211), which sequence comprises the phosphorylatable tyrosine listed in corresponding Column F of Table 1. In certain preferred embodiments, the phosphorylatable tyrosine within the labeled peptide is phosphorylated, while in other preferred embodiments, the phosphorylatable tyrosine within the labeled peptide is not phosphorylated.

Reagents (antibodies and AQUA peptides) provided by the invention may conveniently be grouped by the type of ALCL-related signaling protein in which a given phosphorylation site (for which reagents are provided) occurs. The protein types for each respective protein (in which a phosphorylation site has been discovered) are provided in Column D of Table 1/FIG. 2, and include: Acetyltransferases, Actin Binding Proteins, Adaptor/Scaffold Proteins, Apoptosis Proteins, Calcium-Binding Proteins, Cell Cycle Regulation Proteins, Channel Proteins, Chaperone Proteins, Cytokines, Cytoskeletal Proteins, DNA Binding Proteins, DNA Repair Proteins, Cellular Metabolism and Miscellaneous Enzymes, G Proteins, GTPase Activating Proteins, Guanine Nucleotide Exchange Factors, Helicases, Hydrolases, Ligases, Lipid Binding Proteins, Lyases, Methyltransferases, Motor Proteins, Oxidoreductases, Phosphatases, Proteases, Protein Kinases (including Receptor Tyrosine Kinases), RNA Binding Proteins, Transcription Factors (including Initiation Complexes and Co-activator/Co-repressors), Transferases, Translation Initiation Complexes, Transporter Proteins, Ubiquitin Conjugating System Proteins, and Vesicle Proteins. Each of these distinct protein groups is considered a preferred subset of ALCL-related signal transduction protein phosphorylation sites disclosed herein, and reagents for their detection/quantification may be considered a preferred subset of reagents provided by the invention.

Particularly preferred subsets of the phosphorylation sites (and their corresponding proteins) disclosed herein are those occurring on the following protein types/groups listed in Column D of Table 1/FIG. 2: Protein Kinase(s) (including Receptor Tyrosine Kinase(s)), Adaptor/Scaffold Protein(s), Cellular Metabolism or Miscellaneous Enzyme(s), Oxidoreductase(s), Transcription Factor(s), Cytoskeletal Protein(s), Translation Initiation Complex(es), RNA Binding Protein(s), Protease(s), Acetyltransferase(s), and G protein regulator(s) and GTPase(s). Accordingly, among preferred subsets of reagents provided by the invention are isolated antibodies and AQUA peptides useful for the detection and/or quantification of the foregoing preferred protein/phosphorylation site subsets, as well as for the following preferred protein phosphorylation sites: FAF1 (Tyr225), CUL-2 (Y58), HSP60 (Y227), Dicer1 (Y654), and HDAC1 (Y221).

In one subset of preferred embodiments, there is provided:
(i) An isolated phosphorylation site-specific antibody that specifically binds a Protein Kinase selected from Column A, Rows 125-144, of Table 1 only when phosphorylated at the tyrosine listed in corresponding Column F, Rows 125-144, of Table 1, comprised within the phosphorylatable peptide sequence listed in corresponding Column G, Rows 125-144, of Table 1 (SEQ ID NOs: 124-143), wherein said antibody does not bind said protein when not phosphorylated at said tyrosine.
(ii) An equivalent antibody to (i) above that only binds the Protein Kinase when not phosphorylated at the disclosed site (and does not bind the protein when it is phosphorylated at the site).
(iii) A heavy-isotope labeled peptide (AQUA peptide) for the quantification of a Protein Kinase selected from Column A, Rows 125-144, said labeled peptide comprising the phosphorylatable peptide sequence listed in corresponding Column G, Rows 125-144, of Table 1 (SEQ ID NOs: 124-143), which sequence comprises the phosphorylatable tyrosine listed in corresponding Column F, Rows 125-144, of Table 1.

Among this preferred subset of reagents, antibodies and AQUA peptides for the detection/quantification of the following Protein Kinase phosphorylation sites are particularly preferred: DYRK1A (Y145), DYRK3 (Y209), HIPK1 (Y352), HIPK3 (Y359), PRP4 (Y849), Ack (Y518), NPM-ALK (Y1078, Y1092, Y1131, Y1131, 1278, Y1282, Y1584) (see SEQ ID NOs: 126, 127, 130-132, 134, and 138-143).

In a second subset of preferred embodiments there is provided:

(i) An antibody that specifically binds an Adaptor/Scaffold protein selected from Column A, Rows 11-23, of Table 1 only when phosphorylated at the tyrosine listed in corresponding Column F, Rows 11-23, of Table 1, comprised within the phosphorylatable peptide sequence listed in corresponding Column G, Rows 11-23, of Table 1 (SEQ ID NOs: 10-22), wherein said antibody does not bind said protein when not phosphorylated at said tyrosine.

(ii) An equivalent antibody to (i) above that only binds the Adaptor/Scaffold protein when not phosphorylated at the disclosed site (and does not bind the protein when it is phosphorylated at the site).

(iii) A heavy-isotope labeled peptide (AQUA peptide) for the quantification of an Adaptor/Scaffold protein selected from Column A, Rows 11-23, said labeled peptide comprising the phosphorylatable peptide sequence listed in corresponding Column G, Rows 11-23, of Table 1 (SEQ ID NOs: 10-22), which sequence comprises the phosphorylatable tyrosine listed in corresponding Column F, Rows 125-144, of Table 1.

Among this preferred subset of reagents, antibodies and AQUA peptides for the detection/quantification of the following Adaptor/Scaffold protein phosphorylation sites are particularly preferred: Crk (Y239), Hrs (Y216), IRS-1 (Y46), RACK1 (Y228) (see SEQ ID NOs: 12, 13, 16, and 18).

In another subset of preferred embodiments there is provided:

(i) An isolated phosphorylation site-specific antibody that specifically binds a Cellular Metabolism or Miscellaneous Enzyme selected from Column A, Rows 64-86, of Table 1 only when phosphorylated at the tyrosine listed in corresponding Column F, Rows 64-86, of Table 1, comprised within the phosphorylatable peptide sequence listed in corresponding Column G, Rows 64-86, of Table 1 (SEQ ID NOs: 63-85), wherein said antibody does not bind said protein when not phosphorylated at said tyrosine.

(ii) An equivalent antibody to (i) above that only binds the Cellular Metabolism or Miscellaneous Enzyme when not phosphorylated at the disclosed site (and does not bind the protein when it is phosphorylated at the site).

(iii) A heavy-isotope labeled peptide (AQUA peptide) for the quantification of a Cellular Metabolism or Miscellaneous Enzyme selected from Column A, Rows 64-86, said labeled peptide comprising the phosphorylatable peptide sequence listed in corresponding Column G, Rows 64-86, of Table 1 (SEQ ID NOs: 63-85), which sequence comprises the phosphorylatable tyrosine listed in corresponding Column F, Rows 64-86, of Table 1.

Among this preferred subset of reagents, antibodies and AQUA peptides for the detection/quantification of the following Cellular Metabolism or Miscellaneous Enzyme phosphorylation sites are particularly preferred: ATP-citrate lyase (Y131, Y682), Pyruvate kinase M (Y 104, Y389, Y465 Y82), GAPDH (Y41), PFK-B (Y633), G6PD (Y400) (see SEQ ID NOs: 81, 82, 75-78, 68, 73, and 67).

In still another subset of preferred embodiments there is provided:

(i) An isolated phosphorylation site-specific antibody that specifically binds an Oxidoreductase selected from Column A, Rows 110-115, of Table 1 only when phosphorylated at the tyrosine listed in corresponding Column F, Rows 110-115, of Table 1, comprised within the phosphorylatable peptide sequence listed in corresponding Column G, Rows 110-115, of Table 1 (SEQ ID NOs: 109-114), wherein said antibody does not bind said protein when not phosphorylated at said tyrosine.

(ii) An equivalent antibody to (i) above that only binds the Oxidoreductase when not phosphorylated at the disclosed site (and does not bind the protein when it is phosphorylated at the site).

(iii) A heavy-isotope labeled peptide (AQUA peptide) for the quantification of an Oxidoreductase selected from Column A, Rows 110-115, said labeled peptide comprising the phosphorylatable peptide sequence listed in corresponding Column G, Rows 110-115, of Table 1 (SEQ ID NOs: 109-114), which sequence comprises the phosphorylatable tyrosine listed in corresponding Column F, Rows 110-115, of Table 1.

Among this preferred subset of reagents, antibodies and AQUA peptides for the detection/quantification of the following Oxidoreductase phosphorylation sites are particularly preferred: gluthatione reductase (Y65), thioredoxin reductase (Y11, Y13, Y131, Y422), malate dehydrogenase 2 (Y56) (see SEQ ID NOs: 109, 111-114, and 110).

In still another subset of preferred embodiments there is provided:

(i) An isolated phosphorylation site-specific antibody that specifically binds a Transcription Factor selected from Column A, Rows 171-181, of Table 1 only when phosphorylated at the tyrosine listed in corresponding Column F, Rows 171-181, of Table 1, comprised within the phosphorylatable peptide sequence listed in corresponding Column G, Rows 171-181, of Table 1 (SEQ ID NOs: 170-180), wherein said antibody does not bind said protein when not phosphorylated at said tyrosine.

(ii) An equivalent antibody to (i) above that only binds the Transcription Factor when not phosphorylated at the disclosed site (and does not bind the protein when it is phosphorylated at the site).

(iii) A heavy-isotope labeled peptide (AQUA peptide) for the quantification of a Transcription Factor selected from Column A, Rows 171-181, said labeled peptide comprising the phosphorylatable peptide sequence listed in corresponding Column G, Rows 171-181, of Table 1 (SEQ ID NOs: 170-180), which sequence comprises the phosphorylatable tyrosine listed in corresponding Column F, Rows 171-181, of Table 1.

Among this preferred subset of reagents, antibodies and AQUA peptides for the detection/quantification of the following Transcription Factor phosphorylation sites are particularly preferred: GRF-1 (Y1105), HZF2 (Y520), zinc finger protein 264 (Y231, Y343, Y483, Y511) (see SEQ ID NOs: 170, 171, and 177-180).

In yet another subset of preferred embodiments, there is provided:

(i) An isolated phosphorylation site-specific antibody that specifically binds a Cytoskeletal Protein selected from Column A, Rows 44-58, of Table 1 only when phosphorylated at the tyrosine listed in corresponding Column F, Rows 44-58, of Table 1, comprised within the phosphorylatable peptide sequence listed in corresponding Column G, Rows 44-58, of Table 1 (SEQ ID NOs: 43-57), wherein said antibody does not bind said protein when not phosphorylated at said tyrosine.

(ii) An equivalent antibody to (i) above that only binds the Cytoskeletal Protein when not phosphorylated at the disclosed site (and does not bind the protein when it is phosphorylated at the site).

(iii) A heavy-isotope labeled peptide (AQUA peptide) for the quantification of an ALCL-related signaling protein that is a Cytoskeletal Protein selected from Column A, Rows 44-58, said labeled peptide comprising the phosphorylatable peptide sequence listed in corresponding Column G, Rows 44-58, of Table 1 (SEQ ID NOs: 43-57), which sequence comprises the phosphorylatable tyrosine listed in corresponding Column F, Rows 44-58, of Table 1.

Among this preferred subset of reagents, antibodies and AQUA peptides for the detection/quantification of the following Cytoskeletal Protein phosphorylation sites are particularly preferred: Arp3 (Y231), Cofilin1 (Y140), Talin (Y700), VASP (Y38), vimentin (Y116), profilin 1 (Y128) (see SEQ ID NOs: 46, 48, 52, 55, 56, and 57).

In yet another subset of preferred embodiments, there is provided:
(i) An isolated phosphorylation site-specific antibody that specifically binds a Translation Initiation Complex Protein selected from Column A, Rows 192-207, of Table 1 only when phosphorylated at the tyrosine listed in corresponding Column F, Rows 192-207, of Table 1, comprised within the phosphorylatable peptide sequence listed in corresponding Column G, Rows 192-207, of Table 1 (SEQ ID NOs: 191-206), wherein said antibody does not bind said protein when not phosphorylated at said tyrosine.
(ii) An equivalent antibody to (i) above that only binds the Translation Initiation Complex Protein when not phosphorylated at the disclosed site (and does not bind the protein when it is phosphorylated at the site).
(iii) A heavy-isotope labeled peptide (AQUA peptide) for the quantification of a Translation Initiation Complex Protein selected from Column A, Rows 192-207, said labeled peptide comprising the phosphorylatable peptide sequence listed in corresponding Column G, Rows 192-207, of Table 1 (SEQ ID NOs: 191-206), which sequence comprises the phosphorylatable tyrosine listed in corresponding Column F, Rows 192-207, of Table 1.

Among this preferred subset of reagents, antibodies and AQUA peptides for the detection/quantification of the following Translation Initiation Complex Protein phosphorylation sites are particularly preferred: eEF1A-2 (Y141); eIF3 beta (Y308); eIF3 eta (Y525); eIF3 zeta (Y318); eIF6 (Y113) (SEQ ID NOs: 191-195).

In a further subset of preferred embodiments, there is provided:
(i) An isolated phosphorylation site-specific antibody that specifically binds an RNA Binding Protein selected from Column A, Rows 145-170, of Table 1 only when phosphorylated at the tyrosine listed in corresponding Column F, Rows 145-170, of Table 1, comprised within the phosphorylatable peptide sequence listed in corresponding Column G, Rows 145-170, of Table 1 (SEQ ID NOs: 144-169), wherein said antibody does not bind said protein when not phosphorylated at said tyrosine.
(ii) An equivalent antibody to (i) above that only binds the RNA Binding Protein when not phosphorylated at the disclosed site (and does not bind the protein when it is phosphorylated at the site).
(iii) A heavy-isotope labeled peptide (AQUA peptide) for the quantification of an RNA Binding Protein selected from Column A, Rows 145-170, said labeled peptide comprising the phosphorylatable peptide sequence listed in corresponding Column G, Rows 145-170, of Table 1 (SEQ ID NOs: 144-169), which sequence comprises the phosphorylatable tyrosine listed in corresponding Column F, Rows 145-170, of Table 1.

Among this preferred subset of reagents, antibodies and AQUA peptides for the detection/quantification of the following RNA Binding Protein phosphorylation sites are particularly preferred: PABP1 (Y364, Y54); DDX5 (Y297), Prohibitin D (Y128) (SEQ ID NOs: 150, 151, 167, and 162).

In a further subset of preferred embodiments, there is provided:
(i) An isolated phosphorylation site-specific antibody that specifically binds an a Protease selected from Column A, Rows 118-124, of Table 1 only when phosphorylated at the tyrosine listed in corresponding Column F, Rows 118-124, of Table 1, comprised within the phosphorylatable peptide sequence listed in corresponding Column G, Rows 118-124, of Table 1 (SEQ ID NOs: 117-123), wherein said antibody does not bind said protein when not phosphorylated at said tyrosine.
(ii) An equivalent antibody to (i) above that only binds the Protease when not phosphorylated at the disclosed site (and does not bind the protein when it is phosphorylated at the site).
(iii) A heavy-isotope labeled peptide (AQUA peptide) for the quantification of a Protease selected from Column A, Rows 118-124, said labeled peptide comprising the phosphorylatable peptide sequence listed in corresponding Column G, Rows 118-124, of Table 1 (SEQ ID NOs: 117-123), which sequence comprises the phosphorylatable tyrosine listed in corresponding Column F, Rows 118-124, of Table 1.

Among this preferred subset of reagents, antibodies and AQUA peptides for the detection/quantification of the following Protease phosphorylation sites are particularly preferred: Caspase 8 (Y334); Proteasome Component C3 (Y23, Y97); Proteasome Component Poh1 (Y32) (see SEQ ID NOs: 117-119, and 122).

In still a further subset of preferred embodiments, there is provided:
(i) An isolated phosphorylation site-specific antibody that specifically binds an Acetyltransferase selected from Column A, Rows 2-5, of Table 1 only when phosphorylated at the tyrosine listed in corresponding Column F, Rows 2-5, of Table 1, comprised within the phosphorylatable peptide sequence listed in corresponding Column G, Rows 2-5, of Table 1 (SEQ ID NOs: 1-4), wherein said antibody does not bind said protein when not phosphorylated at said tyrosine.
(ii) An equivalent antibody to (i) above that only binds the Acetyltransferase when not phosphorylated at the disclosed site (and does not bind the protein when it is phosphorylated at the site).
(iii) A heavy-isotope labeled peptide (AQUA peptide) for the quantification of an Acetyltransferase selected from Column A, Rows 2-5, said labeled peptide comprising the phosphorylatable peptide sequence listed in corresponding Column G, Rows 2-5, of Table 1 (SEQ ID NOs: 1-4), which sequence comprises the phosphorylatable tyrosine listed in corresponding Column F, Rows 2-5, of Table 1.

Among this preferred subset of reagents, antibodies and AQUA peptides for the detection/quantification of the following Acetyltransferase phosphorylation sites are particularly preferred: MAK3P (Y110); ELP3 (Y202); GCN5-like 2 (Y734) (see SEQ ID NOs: 3, 1, 2).

In yet a further subset of preferred embodiments, there is provided:
(i) An isolated phosphorylation site-specific antibody that specifically binds a protein selected from the group consisting of FAF-1, CUL-3, HSP60, Dicer-1, and HDAC1 (Column A, Rows 25, 31, 35, 92, and 96, of Table 1) only when phosphorylated at the tyrosine listed in corresponding Column F, Rows 25, 31, 35, 92, and 96, of Table 1, comprised within the phosphorylatable peptide sequence listed in corresponding Column G, Rows 25, 31, 35, 92, and 96, of Table 1 (SEQ ID NOs: 24, 30, 34, 91, and 95), wherein said antibody does not bind said protein when not phosphorylated at said tyrosine.

(ii) An equivalent antibody to (i) above that only binds the FAF1, CUL-3, HSP60, Dicer-1, or HDAC1 protein when not phosphorylated at the disclosed site (and does not bind the protein when it is phosphorylated at the site).

(iii) A heavy-isotope labeled peptide (AQUA peptide) for the quantification of a protein selected from the group consisting of FAF1, CUL-3, HSP60, Dicer-1, and HDAC1, (Column A, Rows 25, 31, 35, 92, and 96, of Table 1), said labeled peptide comprising the phosphorylatable peptide sequence listed in corresponding Column G, Rows 25, 31, 35, 92, and 96, of Table 1 (SEQ ID NOs: (SEQ ID NOs: 24, 30, 34, 91, and 95), which sequence comprises the phosphorylatable tyrosine listed in corresponding Column F, Rows 25, 31, 35, 92, and 96, of Table 1.

In yet a further subset of preferred embodiments, there is provided:

(i) An isolated phosphorylation site-specific antibody that specifically binds a G protein regulator or GTPase selected from Column A, Rows 87-91, of Table 1 only when phosphorylated at the tyrosine listed in corresponding Column F, Rows 87-91, of Table 1, comprised within the phosphorylatable peptide sequence listed in corresponding Column G, Rows 87-91, of Table 1 (SEQ ID NOs: 86-90), wherein said antibody does not bind said protein when not phosphorylated at said tyrosine.

(ii) An equivalent antibody to (i) above that only binds the G protein regulator or GTPase when not phosphorylated at the disclosed site (and does not bind the protein when it is phosphorylated at the site).

(iii) A heavy-isotope labeled peptide (AQUA peptide) for the quantification of a G protein regulator or GTPase selected from Column A, Rows 87-91, said labeled peptide comprising the phosphorylatable peptide sequence listed in corresponding Column G, Rows 87-91, of Table 1 (SEQ ID NOs: 86-90), which sequence comprises the phosphorylatable tyrosine listed in corresponding Column F, Rows 87-91, of Table 1.

Among this preferred subset of reagents, antibodies and AQUA peptides for the detection/quantification of the following G protein regulator or GTPase phosphorylation sites are particularly preferred: Vav1 (Y826); RasGAP (Y615); Ran (Y147); RabGDI alpha (Y333) (see SEQ ID NOs: 90, 89, 87, and 86).

The invention also provides, in part, an immortalized cell line producing an antibody of the invention, for example, a cell line producing an antibody within any of the foregoing preferred subsets of antibodies. In one preferred embodiment, the immortalized cell line is a rabbit hybridoma or a mouse hybridoma.

In certain other preferred embodiments, a heavy-isotope labeled peptide (AQUA peptide) of the invention (for example, an AQUA peptide within an of the foregoing preferred subsets of AQUA peptides) comprises a disclosed site sequence wherein the phosphorylatable tyrosine is phosphorylated. In certain other preferred embodiments, a heavy-isotope labeled peptide of the invention comprises a disclosed site sequence wherein the phosphorylatable tyrosine is not phosphorylated.

The foregoing subsets of preferred reagents of the invention should not be construed as limiting the scope of the invention, which, as noted above, includes reagents for the detection and/or quantification of disclosed phosphorylation sites on any of the other protein type/group subsets (each a preferred subset) listed in Column D of Table 1/FIG. 2.

Also provided by the invention are methods for detecting or quantifying a signaling protein that is tyrosine-phosphorylated in human Anaplastic Large Cell Lymphoma (ALCL), said method comprising the step of utilizing one or more of the above-described reagents of the invention to detect or quantify one or more ALCL-related signaling protein(s) selected from Column A of Table 1 only when phosphorylated at the tyrosine listed in corresponding Column F of Table 1. In certain preferred embodiments of the methods of the invention, the reagents comprise a subset of preferred reagents as described above.

The identification of the disclosed novel ALCL-related phosphorylation sites, and the standard production and use of the reagents provided by the invention are described in further detail below and in the Examples that follow.

All cited references are hereby incorporated herein, in their entirety, by reference. The Examples are provided to further illustrate the invention, and do not in any way limit its scope, except as provided in the claims appended hereto.

TABLE 1

Newly-Discovered ALCL-Related Phosphorylation Sites.

| | A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|---|
| 1 | ELP3 | Q9BVF7 | Acetyltransferase | Y202 | GHTSNNIyEAVKYSE | SEQ ID NO: 1 |
| 2 | GCN5-like 2 | Q92830 | Acetyltransferase | Y734 | LKDPDQLyTTLKNLL | SEQ ID NO: 2 |
| 3 | MAK3P | Q9GZZ1 | Acetyltransferase | Y110 | DGTFDNIyLHVQISN | SEQ ID NO: 3 |
| 4 | transglutaminase 2 | P21980 | Acetyltransferase | Y369 | QEKSEGTyCCGPVPV | SEQ ID NO: 4 |
| 5 | coronin 1C | Q9ULV4 | Actin binding protein | Y301 | EITDESPyVHYLNTF | SEQ ID NO: 5 |
| 6 | GMF-beta | P17774 | Actin binding protein | Y83 | HDDGRVSyPLCFIFS | SEQ ID NO: 6 |
| 7 | L-plastin | P13796 | Actin binding protein | Y124 | SYSEEEKyAFVNWIN | SEQ ID NO: 7 |
| 8 | WDR1 | O75083 | Actin binding protein | Y238 | KAHDGGIyAISWSPD | SEQ ID NO: 8 |

TABLE 1-continued

Newly-Discovered ALCL-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 9 profilin 1 | P07737 | Actin binding protein; Cytoskeletal protein | Y128 | GLINKKCyEMASHLR | SEQ ID NO: 9 |
| 10 CD2AP | Q9Y5K6 | Adaptor/scaffold | Y88 | LVQRISTyGLPAGGI | SEQ ID NO: 10 |
| 11 CGRP-RCP | O75575 | Adaptor/scaffold | Y47 | QNLNTITyETLKYIS | SEQ ID NO: 11 |
| 12 Crk | P46108 | Adaptor/scaffold | Y239 | NLQNGPIyARVIQKR | SEQ ID NO: 12 |
| 13 Hrs | O14964 | Adaptor/scaffold | Y216 | VRVCEPCyEQLNRKA | SEQ ID NO: 13 |
| 14 Intersectin 2 | Q9NZM3 | Adaptor/scaffold | Y858 | QPASVTDyQNVSFSN | SEQ ID NO: 14 |
| 15 Intersectin 2 | Q9NZM3 | Adaptor/scaffold | Y967 | REEPEALyAAVNKKP | SEQ ID NO: 15 |
| 16 IRS-1 | P35568 | Adaptor/scaffold | Y46 | GGPARLEyYENEKKW | SEQ ID NO: 16 |
| 18 RACK1 | P25388 | Adaptor/scaffold | Y228 | LNEGKHLyTLDGGDI | SEQ ID NO: 18 |
| 19 TSAd | Q9NP31 | Adaptor/scaffold | Y216 | SQDPNPQySPIIKQG | SEQ ID NO: 19 |
| 20 TSAd | Q9NP31 | Adaptor/scaffold | Y305 | GEAPSNIyVEVEDEG | SEQ ID NO: 20 |
| 21 TSAd | Q9NP31 | Adaptor/scaffold | Y39 | RSCQNLGyTAASPQA | SEQ ID NO: 21 |
| 22 VAM-1 | Q9NZW5 | Adaptor/scaffold | Y500 | SARIQRAyNHYFDLI | SEQ ID NO: 22 |
| 23 laminin receptor 1 | P08865 | Adhesion; Receptor, misc. | Y139 | QPLTEASyVNLPTIA | SEQ ID NO: 23 |
| 24 FAF1 | Q9UNN5 | Apoptosis | Y225 | QEVKRNVyDLTSIPV | SEQ ID NO: 24 |
| 25 programmed cell death 4 | Q8TAR5 | Apoptosis | Y152 | DDQENCVyETVVLPL | SEQ ID NO: 25 |
| 26 Casp8 | Q14790 | Apoptosis; Protease (non-proteasomal) | Y334 | DGQEAPIyELTSQFT | SEQ ID NO: 26 |
| 27 nucleolysin, TIA-1-related | Q01085 | Apoptosis; RNA binding protein | Y50 | EHTSNDPyCFVEFYE | SEQ ID NO: 27 |
| 28 annexin A1 | P04083 | Calcium-binding protein | Y206 | DSDARALyEAGERRK | SEQ ID NO: 28 |
| 29 MKLP1 | Q02241 | Calcium-binding protein: Motor protein | Y29 | LKDPVGVyCRVRPLG | SEQ ID NO: 29 |
| 30 CUL-3 | Q13618 | Cell cycle regulation | Y58 | GLSFEELyRNAYTMV | SEQ ID NO: 30 |
| 31 VGCNL1 | Q8IZF0 | Channel, calcium | Y497 | PALEDFVyKIFGPGK | SEQ ID NO: 31 |
| 32 VDAC-1 | P21796 | Channel, misc. | Y194 | TEFGGSIyQKVNKKL | SEQ ID NO: 32 |
| 33 VDAC-3 | Q9Y277 | Channel, misc. | Y195 | TEFGGSIyQKVNEKI | SEQ ID NO: 33 |
| 34 HSP60 | P10809 | Chaperone | Y227 | DRGYISPyFINTSKG | SEQ ID NO: 34 |
| 35 HSP70RY | P34932 | Chaperone | Y336 | KLKKEDIyAVEIVGG | SEQ ID NO: 35 |
| 36 HSP70RY | P34932 | Chaperone | Y89 | AEKSNLAyDIVQLPT | SEQ ID NO: 36 |
| 37 HSP90-beta | P08238 | Chaperone | Y483 | KETQKSIyYITGESK | SEQ ID NO: 37 |
| 38 TCP-1-theta | P50990 | Chaperone | Y505 | LDTYLGKyWAIKLAT | SEQ ID NO: 38 |
| 39 tetratricopeptide repeat protein 2 | Q99615 | Chaperone | Y40 | DYNEAYNyYTKAIDM | SEQ ID NO: 39 |

TABLE 1-continued

Newly-Discovered ALCL-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 40 prohibitin, D | Q99623 | Chaperone; RNA binding protein | Y128 | YQRLGLDyEERVLPS | SEQ ID NO: 40 |
| 41 MIF | P14174 | Cytokine | Y36 | ATGKPPQyIAVHVVP | SEQ ID NO: 41 |
| 42 PBEF | P43490 | Cytokine | Y188 | GNLDGLEyKLHDFGY | SEQ ID NO: 42 |
| 43 actin, alpha 1 | P02568 | Cytoskeletal protein | Y220 | DIKEKLCyVALDFEN | SEQ ID NO: 43 |
| 44 actin, beta | P02570 | Cytoskeletal protein | Y218 | DIKEKLCyVALDFEQ | SEQ ID NO: 44 |
| 45 actin, beta | P02570 | Cytoskeletal protein | Y294 | VDIRKDLyANTVLSG | SEQ ID NO: 45 |
| 46 Arp3 | P32391 | Cytoskeletal protein | Y231 | AKAVKERySYVCPDL | SEQ ID NO: 46 |
| 47 Bicd2 | Q8TD16 | Cytoskeletal protein | Y424 | DSHEDGDyYEVDING | SEQ ID NO: 47 |
| 48 cofilin 1 | P23528 | Cytoskeletal protein | Y140 | HELQANCyEEVKDRC | SEQ ID NO: 48 |
| 49 EMAP-4 | Q9HC35 | Cytoskeletal protein | Y226 | IINQEGEyIKMFMRG | SEQ ID NO: 49 |
| 50 similar to beta-actin | XP_301899 | Cytoskeletal protein | Y53 | GMGQKDSyVGNEAQS | SEQ ID NO: 50 |
| 51 stomatin-like protein 2 | Q9UJZ1 | Cytoskeletal protein | Y124 | YGVEDPEyAVTQLAQ | SEQ ID NO: 51 |
| 52 talin 1 | Q9Y490 | Cytoskeletal protein | Y70 | EAGKALDyYMLRNGD | SEQ ID NO: 52 |
| 53 tubulin, alpha-1 | P05209 | Cytoskeletal protein | Y272 | IHFPLATyAPVISAE | SEQ ID NO: 53 |
| 54 tubulin, gamma complex component 2 | Q9BSJ2 | Cytoskeletal protein | Y83 | RNLDPLVyLLSKLTE | SEQ ID NO: 54 |
| 55 VASP | P50552 | Cytoskeletal protein | Y38 | QAFSRVQiYHNPTAN | SEQ ID NO: 55 |
| 56 vimentin | P08670 | Cytoskeletal protein | Y116 | LNDRFANyIDKVRFL | SEQ ID NO: 56 |
| 57 profilin 1 | P07737 | Cytoskeletal protein; Actin binding protein | Y128 | GLINKKCyEMASHLR | SEQ ID NO: 57 |
| 58 H4 | P02304 | DNA binding protein | Y51 | KRISGLIyEETRGVL | SEQ ID NO: 58 |
| 59 RoXaN | Q9UGR2 | DNA binding protein | Y664 | KVWLLQQySGMTHED | SEQ ID NO: 59 |
| 60 zinc finger, CCHC domain-containing 3 | Q9NUD5 | DNA binding protein | Y202 | GMDPSDIyAVIQIPG | SEQ ID NO: 60 |
| 61 hnRNP U | Q00839 | DNA binding protein; RNA binding protein | Y472 | YFPIPEEyTFIQNVP | SEQ ID NO: 61 |
| 62 APE1 | P27695 | DNA repair | Y261 | HLYPNTPyAYTFWTY | SEQ ID NO: 62 |
| 63 aldolase A | P04075 | Enzyme, cellular metabolism | Y203 | HDLKRCQyVTEKVLA | SEQ ID NO: 63 |

TABLE 1-continued

Newly-Discovered ALCL-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 64 enolase, alpha | P06733 | Enzyme, cellular metabolism | Y286 | YKSFIKDyPVVSIED | SEQ ID NO: 64 |
| 65 enolase, alpha | P06733 | Enzyme, cellular metabolism | Y43 | SGASTGIyEALELRD | SEQ ID NO: 65 |
| 66 enolase, neural | P09104 | Enzyme, cellular metabolism | Y43 | SGASTGIyEALELRD | SEQ ID NO: 66 |
| 67 G6PD | P11413 | Enzyme, cellular metabolism | Y400 | VQPNEAVyTKMMTKK | SEQ ID NO: 67 |
| 68 GAPDH | P04406 | Enzyme, cellular metabolism | Y41 | DPFIDLNyMVYMFQY | SEQ ID NO: 68 |
| 69 GART | P22102 | Enzyme, cellular metabolism | Y348 | SKGYPGDyTKGVEIT | SEQ ID NO: 69 |
| 70 IMP dehydrogenase 2 | P12268 | Enzyme, cellular metabolism | Y400 | TTEAPGEyFFSDGIR | SEQ ID NO: 70 |
| 71 LDH-A | P00338 | Enzyme, cellular metabolism | Y238 | KQVVESAyEVIKLKG | SEQ ID NO: 71 |
| 72 LDH-B | P07195 | Enzyme, cellular metabolism | Y239 | KMVVESAyEVIKLKG | SEQ ID NO: 72 |
| 73 PFK-B | P17858 | Enzyme, cellular metabolism | Y633 | RNEKCHDyYTTEFLY | SEQ ID NO: 73 |
| 74 phosphoglycerate kinase 1 | P00558 | Enzyme, cellular metabolism | Y195 | LMKKELNyFAKALES | SEQ ID NO: 74 |
| 75 pyruvate kinase M | P14618 | Enzyme, cellular metabolism | Y104 | FASDPILyRPVAVAL | SEQ ID NO: 75 |
| 76 pyruvate kinase M | P14618 | Enzyme, cellular metabolism | Y389 | REAEAAIyHLQLFEE | SEQ ID NO: 76 |
| 77 pyruvate kinase M | P14618 | Enzyme, cellular metabolism | Y465 | TARQAHLyRGIFPVL | SEQ ID NO: 77 |
| 78 pyruvate kinase M | P14618 | Enzyme, cellular metabolism | Y82 | FSHGTHEyHAETIKN | SEQ ID NO: 78 |
| 79 Nit2 | Q9NQR4 | Enzyme, misc. | Y145 | FSTFDTPyCRVGLGI | SEQ ID NO: 79 |
| 80 PFKP | Q01813 | Enzyme, misc. | Y651 | NYTTDFIyQLYSEEG | SEQ ID NO: 80 |
| 81 ATP-citrate lyase | P53396 | Enzyme, misc.; Lyase | Y131 | YATREGDyVLFHHEG | SEQ ID NO: 81 |
| 82 ATP-citrate lyase | P53396 | Enzyme, misc.; Lyase | Y682 | SRTTDGVyEGVAIGG | SEQ ID NO: 82 |
| 83 Dcp1b | Q8IZD4 | Enzyme, misc.; RNA binding protein | Y110 | RNARLSIyGIWFYDK | SEQ ID NO: 83 |
| 84 Dcp1b | Q8IZD4 | Enzyme, misc.; RNA binding protein | Y133 | LMKNLTQyEQLKAHQ | SEQ ID NO: 84 |
| 85 Dcp1b | Q8IZD4 | Enzyme, misc.; RNA binding protein | Y191<br>Y333 | ITSSSAIyDNPNLIK<br>VNRKSDIyVCMISYA | SEQ ID NO: 85<br>SEQ ID NO: 86 |
| 86 Rab GDI alpha | P31150 | G protein regulator, misc. | | | |

TABLE 1-continued

Newly-Discovered ALCL-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 87 Ran | P17080 | G protein, monomeric (non-Rab) | Y147 | RKKNLQYyDISAKSN | SEQ ID NO: 87 |
| 88 TBC1D1 | Q86T10 | GTPase activating protein, misc. | Y113 | HNSHDPSyFACLIKE | SEQ ID NO: 88 |
| 89 RasGAP | P20936 | GTPase activating protein, Ras | Y615 | VKHFTNPyCNIYLNS | SEQ ID NO: 89 |
| 90 VAV1 | P15498 | Guanine nucleotide exchange factor, Rac/Rho | Y826 | GWWRGEIyGRVGWFP | SEQ ID NO: 90 |
| 91 Dicer1 | Q9UPY3 | Helicase | Y654 | ELPDGTFySTLYLPI | SEQ ID NO: 91 |
| 92 Werner helicase interacting protein | Q96S55 | Helicase | Y534 | EGGEDPLyVARRLVR | SEQ ID NO: 92 |
| 93 Werner helicase interacting protein | Q96S55 | Helicase | Y562 | LTQAVAAyQGCHFMG | SEQ ID NO: 93 |
| 94 DDX5 | P17844 | Helicase; RNA binding protein | Y297 | AEDFLKDyIHINIGA | SEQ ID NO: 94 |
| 95 HDAC1 | Q13547 | Hydrolase, esterase | Y221 | IGAGKGKyYAVNYPL | SEQ ID NO: 95 |
| 96 deoxycytidylate deaminase | P32321 | Hydrolase, non-esterase | Y79 | ENKLDTKyPYVCHAE | SEQ ID NO: 96 |
| 97 oligoribo-nuclease | Q9Y3B8 | Hydrolase, non-esterase | Y122 | ITLQQAEyEFLSFVR | SEQ ID NO: 97 |
| 98 oligoribo-nuclease | Q9Y3B8 | Hydrolase, non-esterase | Y184 | RRWYPEEyEFAPKKA | SEQ ID NO: 98 |
| 99 UDPase | Q9Y227 | Hydrolase, non-esterase | Y385 | QQNGQTIyLRGTGDF | SEQ ID NO: 99 |
| 100 cysteinyl-tRNA synthetase | P49589 | Ligase | Y260 | QKIVDNGyGYVSNGS | SEQ ID NO: 100 |
| 101 glutaminyl-tRNA synthetase | P47897 | Ligase | Y491 | YGRLNLHyAVVSKRK | SEQ ID NO: 101 |
| 102 succinyl-CoA synthetase, betaA chain | Q9P2R7 | Ligase | Y84 | AKSPDEAyAIAKKLG | SEQ ID NO: 102 |
| 103 E-FABP | Q01469 | Lipid binding protein | Y131 | NVTCTRIyEKVE | SEQ ID NO: 103 |
| 104 vigilin | Q00341 | Lipid binding protein; RNA binding protein; Transporter, facilitator | Y437 | DLINRMDyVEINIDH | SEQ ID NO: 104 |
| 105 ATP-citrate lyase | P53396 | Lyase; Enzyme, misc. | Y131 | YATREGDyVLFHHEG | SEQ ID NO: 105 |
| 106 ATP-citrate lyase | P53396 | Lyase; Enzyme, misc. | Y682 | SRTTDGVyEGVAIGG | SEQ ID NO: 106 |
| 107 MDS024 | Q9HC13 | Methyltransferase; RNA binding protein | Y44 | FASSQETyGKSPFWI | SEQ ID NO: 107 |

TABLE 1-continued

Newly-Discovered ALCL-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 108 MKLP1 | Q02241 | Motor protein; Calcium-binding protein | Y29 | LKDPVGVyCRVRPLG | SEQ ID NO: 108 |
| 109 glutathione reductase | P00390 | Oxidoreductase | Y65 | AAGAVASyDYLVIGG | SEQ ID NO: 109 |
| 110 malate dehydrogenase 2 | P40926 | Oxidoreductase | Y56 | LVSRLTLyDIAHTPG | SEQ ID NO: 110 |
| 111 thioredoxin reductase 1 | Q16881 | Oxidoreductase | Y11 | PEDLPKSyDYDLIII | SEQ ID NO: 111 |
| 112 thioredoxin reductase 1 | Q16881 | Oxidoreductase | Y13 | DLPKSYDyDLIIIGG | SEQ ID NO: 112 |
| 113 thioredoxin reductase 1 | Q16881 | Oxidoreductase | Y131 | KVVYENAyGQFIGPH | SEQ ID NO: 113 |
| 114 thioredoxin reductase 1 | Q16881 | Oxidoreductase | Y422 | SRDNNKCyAKIICNT | SEQ ID NO: 114 |
| 115 nudix-type motif 5 | Q9UKK9 | Phosphatase | Y74 | VLQRTLHyECIVLVK | SEQ ID NO: 115 |
| 116 INPP4 | O15326 | Phosphatase, lipid | Y355 | DGGSDQNyDIVTIGA | SEQ ID NO: 116 |
| 117 Casp8 | Q14790 | Protease (non-proteasomal); Apoptosis | Y334 | DGQEAPIyELTSQFT | SEQ ID NO: 117 |
| 118 Proteasome component C3 | P25787 | Protease (proteasomal subunit) | Y23 | GKLVQIEyALAAVAG | SEQ ID NO: 118 |
| 119 Proteasome component C3 | P25787 | Protease (proteasomal subunit) | Y97 | RKLAQQYyLVYQEPI | SEQ ID NO: 119 |
| 120 proteasome component C8 | P25788 | Protease (proteasomal subunit) | Y160 | PSGVSYGyWGCAIGK | SEQ ID NO: 120 |
| 121 proteasome component N3 | P28070 | Protease (proteasomal subunit) | Y102 | MLGASGDyADFQYLK | SEQ ID NO: 121 |
| 122 proteasome component Poh1 | O00487 | Protease (proteasomal subunit) | Y32 | VDTAEQVyISSLALL | SEQ ID NO: 122 |
| 123 proteasome component Z | Q99436 | Protease (proteasomal subunit) | Y154 | DVTGPHLySIYPHGS | SEQ ID NO: 123 |
| 124 A6r | Q9Y3F5 | Protein kinase | Y309 | ELTAEFLyDEVHPKQ | SEQ ID NO: 124 |
| 125 A6 | Q12792 | Protein kinase, dual-specificity | Y327 | ELTADFLyEEVHPKQ | SEQ ID NO: 125 |
| 126 DYRK1A | Q13627 | Protein kinase, dual-specificity | Y145 | DGYDDDNyDYIVKNG | SEQ ID NO: 126 |
| 127 DYRK3 | O43781 | Protein kinase, dual-specificity | Y209 | RDHLAYRyEVLKIIG | SEQ ID NO: 127 |
| 128 Cdc2 | P06493 | Protein kinase, Ser/Thr (non-receptor) | Y19 | EGTYGVVyKGRHKTT | SEQ ID NO: 128 |

TABLE 1-continued

Newly-Discovered ALCL-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 129 GSK3-alpha | P49840 | Protein kinase,<br>Ser/Thr (non-<br>receptor) | Y279 | RGEPNVSyICSRYYR | SEQ ID NO: 129 |
| 130 HIPK1 | Q86Z02 | Protein kinase,<br>Ser/Thr (non-<br>receptor) | Y352 | SKAVCSTyLQSRYYR | SEQ ID NO: 130 |
| 131 HIPK3 | O14632 | Protein kinase,<br>Ser/Thr (non-<br>receptor) | Y359 | SKTVCSTyLQSRYYR | SEQ ID NO: 131 |
| 132 PRP4 | Q13523 | Protein kinase,<br>Ser/Thr (non-<br>receptor) | Y849 | ADNDITPyLVSRFYR | SEQ ID NO: 132 |
| 133 SgK223 | Q86YV5 | Protein kinase,<br>Ser/Thr (non-<br>receptor) | Y390 | ATQPEPIyAESTKRK | SEQ ID NO: 133 |
| 134 Ack | Q07912 | Protein kinase,<br>tyrosine (non-<br>receptor) | Y518 | GGVKKPTyDPVSEDQ | SEQ ID NO: 134 |
| 136 SHP-2 | Q06124 | Protein<br>phosphatase,<br>tyrosine (non-<br>receptor) | Y62 | KIQNTGDyYDLYGGE | SEQ ID NO: 136 |
| 137 laminin receptor 1 | P08865 | Receptor, misc.;<br>Adhesion | Y139 | QPLTEASyVNLPTIA | SEQ ID NO: 137 |
| 138 ALK | Q9UM73 | Receptor tyrosine<br>kinase | Y1078 | MELQSPEyKLSKLRT | SEQ ID NO: 138 |
| 139 ALK | Q9UM73 | Receptor tyrosine<br>kinase | Y1092 | TSTIMTDyNPNYCFA | SEQ ID NO: 139 |
| 140 ALK | Q9UM73 | Receptor tyrosine<br>kinase | Y1131 | HGAFGEVyEGQVSGM | SEQ ID NO: 140 |
| 141 ALK | Q9UM73 | Receptor tyrosine<br>kinase | Y1278 | FGMARDIyRASYYRK | SEQ ID NO: 141 |
| 142 ALK | Q9UM73 | Receptor tyrosine<br>kinase | Y1282 | RDIYRASyYRKGGCA | SEQ ID NO: 142 |
| 143 ALK | Q9UM73 | Receptor tyrosine<br>kinase | Y1584 | FPCGNVNyGYQQQGL | SEQ ID NO: 143 |
| 144 hnRNP H | P31943 | RNA binding<br>protein | Y306 | RATENDIyNFFSPLN | SEQ ID NO: 144 |
| 145 hnRNP-A1 | P09651 | RNA binding<br>protein | Y346 | PYGGGGQyFAKPRNQ | SEQ ID NO: 145 |
| 146 LSm2 | Q9Y333 | RNA binding<br>protein | Y35 | TLHSVDQyLNIKLTD | SEQ ID NO: 146 |
| 147 mRNA cleavage factor Im | O43809 | RNA binding<br>protein | Y40 | LERTINLyPLTNYTF | SEQ ID NO: 147 |
| 148 mRNA cleavage factor, 50 kDa subunit | Q05048 | RNA binding<br>protein | Y367 | VFNHTEDyVLLPDER | SEQ ID NO: 148 |
| 149 MVP | Q14764 | RNA binding<br>protein | Y13 | FIIRIPPyHYIHVLD | SEQ ID NO: 149 |
| 150 PABP 1 | P11940 | RNA binding<br>protein | Y364 | IVATKPLyVALAQRK | SEQ ID NO: 150 |

TABLE 1-continued

Newly-Discovered ALCL-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 151 PABP 1 | P11940 | RNA binding protein | Y54 | ITRRSLGyAYVNFQQ | SEQ ID NO: 151 |
| 152 PABP 4 | Q13310 | RNA binding protein | Y140 | DENGSKGyAFVHFET | SEQ ID NO: 152 |
| 153 RNA-binding protein S1 | Q15287 | RNA binding protein | Y205 | HPHLSKGyAYVEFEN | SEQ ID NO: 153 |
| 154 snRNP B | P08579 | RNA binding protein | Y151 | VPDYPPNyILFLNNL | SEQ ID NO: 154 |
| 155 splicing factor 2 | Q07955 | RNA binding protein | Y188 | SHEGETAyIRVKVDG | SEQ ID NO: 155 |
| 156 splicing factor 3A subunit 1 | Q15459 | RNA binding protein | Y759 | AGKQKLQyEGIFIKD | SEQ ID NO: 156 |
| 157 splicing factor 3A subunit 3 | Q12874 | RNA binding protein | Y414 | NCEICGNyTYRGPKA | SEQ ID NO: 157 |
| 158 splicing factor 3B subunit 4 | Q15427 | RNA binding protein | Y56 | VTGQHQGyGFVEFLS | SEQ ID NO: 158 |
| 159 splicing factor 3B, 14 kDa subunit | Q9Y3B4 | RNA binding protein | Y86 | GFNVCNRyLVVLYYN | SEQ ID NO: 159 |
| 160 splicing factor, Arg/Ser-rich 4 | Q08170 | RNA binding protein | Y53 | RDADDAVyELNGKDL | SEQ ID NO: 160 |
| 161 nucleolysin, TIA-1-related | Q01085 | RNA binding protein; Apoptosis | Y50 | EHTSNDPyCFVEFYE | SEQ ID NO: 161 |
| 162 prohibitin, D | Q99623 | RNA binding protein; Chaperone | Y128 | YQRLGLDyEERVLPS | SEQ ID NO: 162 |
| 163 hnRNP U | Q00839 | RNA binding protein; DNA binding protein | Y454 | YFPIPEEyTFIQNVP | SEQ ID NO: 163 |
| 164 Dcp1b | Q8IZD4 | RNA binding protein; Enzyme, misc. | Y110 | RNARLSIyGIWFYDK | SEQ ID NO: 164 |
| 165 Dcp1b | Q8IZD4 | RNA binding protein; Enzyme, misc. | Y133 | LMKNLTQyEQLKAHQ | SEQ ID NO: 165 |
| 166 Dcp1b | Q8IZD4 | RNA binding protein; Enzyme, misc. | Y191 | ITSSSAIyDNPNLIK | SEQ ID NO: 166 |
| 167 DDX5 | P17844 | RNA binding protein; Helicase | Y297 | AEDFLKDyIHINIGA | SEQ ID NO: 167 |
| 168 MDS024 | Q9HC13 | RNA binding protein; Methyltransferase | Y44 | FASSQETyGKSPFWI | SEQ ID NO: 168 |
| 169 vigilin | Q00341 | RNA binding protein; Transporter, facilitator; Lipid binding protein | Y437 | DLINRMDyVEINIDH | SEQ ID NO: 169 |
| 170 GRF-1 | Q9NRY4 | Transcription factor | Y1105 | RNEEENIySVPHDST | SEQ ID NO: 170 |
| 171 HZF2 | Q14586 | Transcription factor | Y520 | IHTGENLyKCKVCAK | SEQ ID NO: 171 |

TABLE 1-continued

Newly-Discovered ALCL-Related Phosphorylation Sites.

| Protein Name (short) | Accession Number | Protein Type | Phospho-Residue | Phosphorylation Site Sequence | SEQ ID NO: |
|---|---|---|---|---|---|
| 172 transcription factor 20 | Q9UGU0 | Transcription factor | Y548 | STSSDTTyKGGASEK | SEQ ID NO: 172 |
| 173 zinc finger protein 147 | Q14258 | Transcription factor | Y278 | NSKFDTIyQILLKKK | SEQ ID NO: 173 |
| 174 zinc finger protein 174 | Q15697 | Transcription factor | Y382 | IHTGEKPyQCGQCGK | SEQ ID NO: 174 |
| 175 zinc finger protein 24 | P17028 | Transcription factor | Y279 | IHSGEKPyGCVECGK | SEQ ID NO: 175 |
| 176 zinc finger protein 24 | P17028 | Transcription factor | Y335 | IHTGEKPyECVQCGK | SEQ ID NO: 176 |
| 177 zinc finger protein 264 | O43296 | Transcription factor | Y231 | IHSGVKPyECTECGK | SEQ ID NO: 177 |
| 178 zinc finger protein 264 | O43296 | Transcription factor | Y343 | VHSGENPyECLECGK | SEQ ID NO: 178 |
| 179 zinc finger protein 264 | O43296 | Transcription factor | Y483 | IHTGEKPyECVECGK | SEQ ID NO: 179 |
| 180 zinc finger protein 264 | O43296 | Transcription factor | Y511 | IHSGEKPyECVECGK | SEQ ID NO: 180 |
| 181 Sui1 | P41567 | Transcription initiation complex | Y30 | LPAGTEDyIHIRIQQ | SEQ ID NO: 181 |
| 182 SSRP1 | Q08945 | Transcription initiation complex; Transcription, coactivator/core-pressor | Y311 | KNMSGSLyEMVSRVM | SEQ ID NO: 182 |
| 183 EBNA-2 coactivator | Q13122 | Transcription, coactivator/core-pressor | Y84 | KTPQGREyGMIYLGK | SEQ ID NO: 183 |
| 184 TRIP13 | Q15645 | Transcription, coactivator/core-pressor | Y58 | HNIVFGDyTWTEFDE | SEQ ID NO: 184 |
| 185 SSRP1 | Q08945 | Transcription, coactivator/core-pressor; Transcription initiation complex | Y311 | KNMSGSLyEMVSRVM | SEQ ID NO: 185 |
| 186 DNA primase 2A | P49643 | Transferase | Y381 | NPPSQGDyHGCPFRH | SEQ ID NO: 186 |
| 187 farnesyltrans-ferase beta | P49356 | Transferase | Y300 | NKLVDGCySFWQAGL | SEQ ID NO: 187 |
| 188 glycogen branching enzyme | Q04446 | Transferase | Y173 | REGDNVNyDWIHWDP | SEQ ID NO: 188 |
| 189 spermine synthase | P52788 | Transferase | Y147 | VYDEDSPyQNIKILH | SEQ ID NO: 189 |
| 190 transketolase | P29401 | Transferase | Y275 | EQIIQEIySQIQSKK | SEQ ID NO: 190 |
| 191 eEF1A-2 | Q05639 | Translation initiation complex | Y141 | REHALLAyTLGVKQL | SEQ ID NO: 191 |
| 192 eIF3-beta | Q13347 | Translation initiation complex | Y308 | SSGGEDGyVRIHYFD | SEQ ID NO: 192 |
| 193 eIF3-eta | P55884 | Translation initiation complex | Y525 | HWQKNGDyLCVKVDR | SEQ ID NO: 193 |

TABLE 1-continued

Newly-Discovered ALCL-Related Phosphorylation Sites.

| A<br>Protein Name<br>(short) | C<br>Accession<br>Number | D<br>Protein Type | F<br>Phospho-<br>Residue | G<br>Phosphorylation<br>Site Sequence | H<br>SEQ ID NO: |
|---|---|---|---|---|---|
| 194 eIF3-zeta | O15371 | Translation initiation complex | Y318 | NLAMEATyINHNFSQ | SEQ ID NO: 194 |
| 195 eIF6 | P56537 | Translation initiation complex | Y113 | NVTTCNDyVALVHPD | SEQ ID NO: 195 |
| 196 ribosomal protein L12 | P30050 | Translation initiation complex | Y14 | PNEIKVVyLRCTGGE | SEQ ID NO: 196 |
| 197 ribosomal protein L18a | Q02543 | Translation initiation complex | Y63 | KSSGEIVyCGQVFEK | SEQ ID NO: 197 |
| 198 ribosomal protein L23 | P23131 | Translation initiation complex | Y38 | NTGAKNLyIISVKGI | SEQ ID NO: 198 |
| 199 ribosomal protein L31 | P12947 | Translation initiation complex | Y103 | EDSPNKLyTLVTYVP | SEQ ID NO: 199 |
| 200 ribosomal protein L31 | P12947 | Translation initiation complex | Y108 | KLYTLVTyVPVTTFK | SEQ ID NO: 200 |
| 201 ribosomal protein L7 | P18124 | Translation initiation complex | Y139 | MLRIVEPyIAWGYPN | SEQ ID NO: 201 |
| 202 ribosomal protein L7 | P18124 | Translation initiation complex | Y195 | EDLIHEIyTVGKRFK | SEQ ID NO: 202 |
| 203 ribosomal protein L8 | P25120 | Translation initiation complex | Y132 | LARASGNyATVISHN | SEQ ID NO: 203 |
| 204 ribosomal protein P0 | P05388 | Translation initiation complex | Y24 | IIQLLDDyPKCFIVG | SEQ ID NO: 204 |
| 205 ribosomal protein S10 | P46783 | Translation initiation complex | Y12 | KKNRIAIyELLFKEG | SEQ ID NO: 205 |
| 206 ribosomal protein S13 | Q02546 | Translation initiation complex | Y37 | DDVKEQIyKLAKKGL | SEQ ID NO: 206 |
| 207 RanBP7 | O95373 | Transporter, facilitator | Y311 | LLKVLYQyKEKQYMA | SEQ ID NO: 207 |
| 208 vigilin | Q00341 | Transporter, facilitator; RNA binding protein; Lipid binding protein | Y437 | DLINRMDyVEINIDH | SEQ ID NO: 208 |
| 209 sequestosome 1 | Q13501 | Ubiquitin conjugating system | Y148 | KCSVCPDyDLCSVCE | SEQ ID NO: 209 |
| 210 adaptin, beta | P21851 | Vesicle protein | Y737 | THRQGHIyMEMNFTN | SEQ ID NO: 210 |
| 211 HEP-COP | P53621 | Vesicle protein | Y249 | VDTCRGHyNNVSCAV | SEQ ID NO: 211 |

The short name for each protein in which a phosphorylation site has presently been identified is provided in Column A, and it accession number (human) is provided Column C. The protein type/group into which each protein falls is provided in Column D. The identified tyrosine residue at which phosphorylation occurs in a given protein is identified in Column F, and the amino acid sequence of the phosphorylation site encompassing the tyrosine residue is provided in Column G (lower case y=the tyrosine (identified in Column F) at which phosphorylation occurs. Table 1 above is identical to FIG. 2, except that the latter includes the full protein name (Column B) and indicates the ALCL cell line(s) in which a given phosphorylation site was discovered (Column I).

The identification of these 211 phosphorylation sites is described in more detail in Part A below and in Example 1.

Definitions.

As used herein, the following terms have the meanings indicated:

"Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. The term "does not bind" with respect to an antibody's binding to one phospho-form of a sequence means does not substantially react with as compared to the antibody's binding to the other phospho-form of the sequence for which the antibody is specific.

"ALCL-related signaling protein" means any protein (or polypeptide derived therefrom) enumerated in Column A of Table 1/FIG. 2, which is disclosed herein as being phosphorylated in one or more Anaplastic Large Cell Lymphoma (ALCL) cell line(s). An ALCL-related signaling protein may also be phosphorylated in other non-ALCL cell lines.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below.

"Protein" is used interchangeably with polypeptide, and includes protein fragments and domains as well as whole protein.

"Phosphorylatable amino acid" means any amino acid that is capable of being modified by addition of a phosphate group, and includes both forms of such amino acid.

"Phosphorylatable peptide sequence" means a peptide sequence comprising a phosphorylatable amino acid.

"Phosphorylation site-specific antibody" means an antibody that specifically binds a phosphorylatable peptide sequence/epitope only when phosphorylated, or only when not phosphorylated, respectively. The term is used interchangeably with "phospho-specific" antibody.

A. Identification of Novel ALCL-Related Phosphorylation Sites.

The 211 novel ALCL-related signaling protein phosphorylation sites disclosed herein and listed in Table 1/FIG. 2 were discovered by employing the modified peptide isolation and characterization techniques described in described in "Immunoaffinity Isolation of Modified Peptides From Complex Mixtures," U.S. Patent Publication No. 20030044848, Rush et al. (the teaching of which is hereby incorporated herein by reference, in its entirety) using cellular extracts from two recognized ALCL tumor cell lines: Karpas 299 cells and SU-DHL1 cells. The isolation and identification of phosphopeptides from these ALCL cell lines, using an immobilized general phosphotyrosine-specific antibody, is described in detail in Example 1 below. In addition to the 211 previously unknown protein phosphorylation sites discovered, many known phosphorylation sites were also identified (but are described herein). The immunoaffinity/mass spectrometric technique described in the '848 patent Publication (the "IAP" method)—and employed as described in detail in the Examples—is briefly summarized below.

The IAP method employed generally comprises the following steps: (a) a proteinaceous preparation (e.g. a digested cell extract) comprising phosphopeptides from two or more different proteins is obtained from an organism; (b) the preparation is contacted with at least one immobilized general phosphotyrosine-specific antibody; (c) at least one phosphopeptide specifically bound by the immobilized antibody in step (b) is isolated; and (d) the modified peptide isolated in step (c) is characterized by mass spectrometry (MS) and/or tandem mass spectrometry (MS-MS). Subsequently, (e) a search program (e.g. Sequest) may be utilized to substantially match the spectra obtained for the isolated, modified peptide during the characterization of step (d) with the spectra for a known peptide sequence. A quantification step employing, e.g. SILAC or AQUA, may also be employed to quantify isolated peptides in order to compare peptide levels in a sample to a baseline.

In the IAP method as employed herein, a general phosphotyrosine-specific monoclonal antibody (commercially available from Cell Signaling Technology, Inc., Beverly, Mass., Cat #9411 (p-Tyr-100)) was used in the immunoaffinity step to isolate the widest possible number of phospho-tyrosine containing peptides from the ALCL cell extracts.

Extracts from Karpas 299 and SU-DHL1 cell lines, both derived from anaplastic large cell lymphomas (ALCL), were employed. Although the two cell lines are derived from different patients, both express the oncogenic fusion kinase ALK-NPM, which possesses constitutive tyrosine kinase activity and can transform non-malignant cells.

As described in more detail in the Examples, lysates were prepared from both cell lines and digested with trypsin after treatment with DTT and iodoacetamide to alkylate cysteine residues. Before the immunoaffinity step, peptides were pre-fractionated by reversed-phase solid phase extraction using Sep-Pak $C_{18}$ columns to separate peptides from other cellular components. The solid phase extraction cartridges were eluted with varying steps of acetonitrile. Each lyophilized peptide fraction was redissolved in PBS and treated with phosphotyrosine antibody (P-Tyr-100, CST #9411) immobilized on protein G-Sepharose. Immunoaffinity-purified peptides were eluted with 0.1% TFA and a portion of this fraction was concentrated with Stage tips and analyzed by LC-MS/MS, using a ThermoFinnigan LCQ Deca XP Plus ion trap mass spectrometer. Peptides were eluted from a 10 cm×75 µm reversed-phase column with a 45-min linear gradient of acetonitrile. MS/MS spectra were evaluated using the program Sequest with the NCBI human protein database.

This revealed a total of 117 novel tyrosine phosphorylation sites in SU-DHL-1 and 84 novel tyrosine phosphorylation sites in Karpas 299. As expected there was large overlap (72%) between the phosphorylation sites found in these two similar cell lines. The identified phosphorylation sites and their parent proteins are enumerated in Table 1/FIG. 2. The tyrosine (human sequence) at which phosphorylation occurs is provided in Column F, and the peptide sequence encompassing the phosphorylatable tyrosine residue at the site is provided in Column G.

As a result of the discovery of these phosphorylation sites, phospho-specific antibodies and AQUA peptides for the detection of and quantification of these sites and their parent proteins may now be produced by standard methods, described below. These new reagents will prove highly useful in studying the signaling pathways and events underlying the progression of ALCL and the identification of new biomarkers and targets for its diagnosis and treatment.

B. Antibodies and Cell Lines

Isolated phosphorylation site specific antibodies that specifically bind an ALCL-related signaling protein disclosed in Column A of Table 1 only when phosphorylated (or only when not phosphorylated) at the corresponding amino acid and phosphorylation site listed in Columns F and G of Table 1 may now be produced by standard antibody production methods, such as anti-peptide antibody methods, using the phosphorylation site sequence information provided in Column G of Table 1. For example, seven new ALK phosphorylation sites (tyrosines 139, 1078, 1092, 1131, 1278, 1282, and 1584) (see Rows 139-144 of Table 1) are presently disclosed. Thus, antibodies that specifically bind any one of these novel ALK sites can now be produced by using (all or part on the amino acid sequence encompassing the respective phosphorylated residue as a peptide antigen used to immunize an animal (e.g. a peptide antigen comprising the sequence set forth in Row 141, Column G, of Table 1 (which encompasses the phosphorylated tyrosine as position 1131 in ALK) may be employed to produce an antibody that only binds ALK when phosphorylated at tyr1131).

Polyclonal antibodies of the invention may be produced according to standard techniques by immunizing a suitable animal (e.g., rabbit, goat, etc.) with a peptide antigen corresponding to the ALCL-related phosphorylation site of interest (i.e. a phosphorylation site enumerated in Column G of Table 1, which comprises the corresponding phosphorylatable amino acid listed in Column F of Table 1), collecting immune serum from the animal, and separating the polyclonal antibodies from the immune serum, in accordance with known procedures. For example, a peptide antigen comprising the novel Ack phosphorylation site disclosed herein (SEQ ID NO: 134=GGVKKPTyDPVSEDQ, encompassing phosphorylated tyrosine 518 (see Row 135 of Table 1)) may be used to produce antibodies that only bind Ack when phosphorylated at Tyr518. Similarly, a peptide comprising any of the phosphorylation site sequences provided in Column G of Table 1 may employed as an antigen to produce an antibody that only binds the corresponding protein listed in Column A of Table 1 when phosphorylated (or when not phosphorylated) at the corresponding residue listed in Column F. If an antibody that only binds the protein when phosphorylated at the disclosed site is desired, the peptide antigen includes the phosphorylated form of the amino acid. Conversely, if an antibody that only binds the protein when not phosphorylated at the disclosed site is desired, the peptide antigen includes the non-phosphorylated form of the amino acid.

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85: 21-49 (1962)).

It will be appreciated by those of skill in the art that longer or shorter phosphopeptide antigens may be employed. See Id. For example, a peptide antigen may consist of the full sequence disclosed in Column G of Table 1, or it may comprise additional amino acids flanking such disclosed sequence, or may comprise of only a portion of the disclosed sequence immediately flanking the phosphorylatable amino acid (indicated in Column G by lowercase "y"). Polyclonal antibodies produced as described herein may be screened as further described below.

Monoclonal antibodies of the invention may be produced in a hybridoma cell line according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246:1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)).

The preferred epitope of a phosphorylation-site specific antibody of the invention is a peptide fragment consisting essentially of about 8 to 17 amino acids including the phosphorylatable tyrosine, wherein about 3 to 8 amino acids are positioned on each side of the phosphorylatable tyrosine (for example, the MVP tyrosine 13 phosphorylation site sequence disclosed in Row 150, Column G of Table 1), and antibodies of the invention thus specifically bind a target ALCL polypeptide comprising such epitopic sequence. Particularly preferred epitopes bound by the antibodies of the invention comprise all or part of a phosphorylatable site sequence listed in Column G of Table 1, including the phosphorylatable amino acid.

Included in the scope of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., *Nature* 312: 604 (1984). Such equivalent non-antibody reagents may be suitably employed in the methods of the invention further described below.

Antibodies provided by the invention may be any type of immunoglobulins, including IgG, IgM, IgA, IgD, and IgE, including Fab or antigen-recognition fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

The invention also provides immortalized cell lines that produce an antibody of the invention. For example, hybridoma clones, constructed as described above, that produce monoclonal antibodies to the ALCL-related signaling protein phosphorylation sties disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Phosphorylation site-specific antibodies of the invention, whether polyclonal or monoclonal, may be screened for epitope and phospho-specificity according to standard techniques. See, e.g. Czernik et al., *Methods in Enzymology,* 201: 264-283 (1991). For example, the antibodies may be screened against the phospho and non-phospho peptide library by ELISA to ensure specificity for both the desired antigen (i.e. that epitope including a phosphorylation site sequence enumerated in Column G of Table 1) and for reactivity only with the phosphorylated (or non-phosphorylated) form of the antigen. Peptide competition assays may be carried out to confirm lack of reactivity with other phospho-epitopes on the given ALCL-related signaling protein. The antibodies may also be tested by Western blotting against cell preparations containing the signaling protein, e.g. cell lines over-expressing the target protein, to confirm reactivity with the desired phosphorylated epitope/target.

Specificity against the desired phosphorylated epitope may also be examined by constructing mutants lacking phosphorylatable residues at positions outside the desired epitope known to be phosphorylated, or by mutating the desired phospho-epitope and confirming lack of reactivity. Phosphorylation-site specific antibodies of the invention may exhibit some limited cross-reactivity related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify sites highly homologous to the ALCL-related signaling protein epitope for which the antibody of the invention is specific. In certain cases, polyclonal antisera may be exhibit some undesirable general cross-reactivity to phosphotyrosine, which may be removed by further purification of antisera, e.g. over a phosphotyramine column. Antibodies of the invention specifically bind their target protein (i.e. a protein listed in Column A of Table 1) only when phosphorylated (or only when not phosphorylated, as the case may be) at the site disclosed in corresponding Columns F/H, and do not (substantially) bind to the other form (as compared to the form for which the antibody is specific).

Antibodies may be further characterized via immunohistochemical (IHC) staining using normal and diseased tissues to examine ALCL-related phosphorylation and activation status in diseased tissue. IHC may be carried out according to well known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry (Communications in Clinical Cytometry)* 46:72-78 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37° C. followed by permeabilization in 90% methanol for 30 minutes on ice. Cells may then be stained with the primary phosphorylation-site specific antibody of the invention (which detects an ALCL-related signal transduction protein enumerated in Table 1), washed and labeled with a fluorescent-labeled secondary antibody. Additional fluorochrome-conjugated marker antibodies (e.g. CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies.

Phosphorylation-site specific antibodies of the invention specifically bind to a human ALCL-related signal transduction protein only when phosphorylated at a disclosed site, but are not limited only to binding the human species, per se. The invention includes antibodies that also bind conserved and highly-homologous phosphorylation sites in respective ALCL-related proteins from other species (e.g. mouse, rat, monkey, yeast), in addition to binding the human phosphorylation site. Highly-homologous sites conserved in other species can readily be identified by standard sequence comparisons, such as using BLAST, with the human ALCL-signal transduction protein phosphorylation sites disclosed herein.

C. Heavy-Isotope Labeled Peptides (AQUA Peptides).

The novel ALCL-signaling protein phosphorylation sites disclosed herein now enable the production of corresponding heavy-isotope labeled peptides for the absolute quantification of such signaling proteins (both phosphorylated and not phosphorylated at a disclosed site) in biological samples. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures. Because an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP-LC-MS/MS method within in a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or MS" spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

In accordance with the present invention, AQUA internal peptide standards (heavy-isotope labeled peptides) may now be produced, as described above, for any of the 211 novel ALCL-related signaling protein phosphorylation sites disclosed herein (see Table 1/FIG. 2). Peptide standards for a given phosphorylation site (e.g. the tyrosine 849 site in PRP4—see Row 133 of Table 1) may be produced for both the phosphorylated and non-phosphorylated forms of the site (e.g. see PRP4 site sequence in Column G, Row 1133 of Table 1) and such standards employed in the AQUA methodology to detect and quantify both forms of such phosphorylation site in a biological sample.

The phosphorylation site peptide sequences disclosed herein (see Column G of Table 1/FIG. 2) are particularly well suited for development of corresponding AQUA peptides, since the IAP method by which they were identified (see Part A above and Example 1) inherently confirmed that such peptides are in fact produced by enzymatic digestion (trypsinization) and are in fact suitably fractionated/ionized in MS/MS. Thus, heavy-isotope labeled equivalents of these peptides (both in phosphorylated and unphosphorylated form) can be readily synthesized and their unique MS and LC-SRM signature determined, so that the peptides are validated as AQUA peptides and ready for use in quantification experiments.

Accordingly, the invention provides heavy-isotope labeled peptides (AQUA peptides) for the detection and/or quantification of any of the ALCL-related phosphorylation sites disclosed in Table 1 (see Column G) and/or their corresponding parent proteins (see Column A). Each such phosphorylation sequence may be considered a preferred AQUA peptide of the invention. Optimally, an AQUA peptide of the invention consists of a phosphorylation site sequence enumerated in Table 1. For example, an AQUA peptide comprising the sequence KIQNTGDyYDLYGGE (SEQ ID NO: 136) (where y may be either phosphotyrosine or tyrosine, and where L=labeled leucine (e.g. $^{14}C$)) is provided for the quantification of phosphorylated (or non-phosphorylated) SHP-2 (tyr62) in a biological sample (see Row 137 of Table 1, tyrosine 62 being the phosphorylatable residue within the site). However, it will be appreciated that a larger AQUA peptide comprising the disclosed phosphorylation site sequence (and additional residues downstream or upstream of it) may also be constructed. Similarly, a smaller AQUA peptide comprising less than all of the residues of a disclosed phosphorylation site sequence (but still comprising the phosphorylatable residue enumerated in Column F) may alternatively be constructed. Such larger or shorter AQUA peptides are within the scope of the present invention, and the selection and production of preferred AQUA peptides may be carried out as described above (see Gygi et al., Gerber et al. supra.).

Certain particularly preferred subsets of AQUA peptides provided by the invention are described above (corresponding to particular protein types/groups in Table 1, for example, Protein Kinases or RNA Binding Proteins). Example 4 is provided to further illustrate the construction and use, by standard methods described above, of exemplary AQUA peptides provided by the invention. For example, AQUA peptides corresponding to the both the phosphorylated and non-phosphorylated forms of the disclosed SHP-2 tyrosine 62 phosphorylation site (KIQNTGDyYDLYGGE (SEQ ID NO: 136)—see Row 137 of Table 1/FIG. 2) may be used to quantify the amount of phosphorylated SHP-2 (tyr62) in biological sample, e.g. an ALCL tumor cell sample (or a sample before or after treatment with a test drug).

AQUA peptides of the invention may also be employed within a kit that comprises one or multiple AQUA peptide(s) provided herein (for the quantification of an ALCL-related signal transduction protein disclosed in Table 1), and, optionally, a second detecting reagent conjugated to a detectable group. For example, a kit may include AQUA peptides for both the phosphorylation and non-phosphorylated form of a phosphorylation site disclosed herein. The reagents may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

AQUA peptides provided by the invention will be highly useful in the further study of signal transduction anomalies underlying ALCL, and in identifying diagnostic/bio-markers of this disease, new potential drug targets, and/or in monitoring the effects of test compounds on ALCL-related signal transduction proteins and pathways.

D. Immunoassay Formats

Antibodies provided by the invention may be advantageously employed in a variety of standard immunological assays (the use of AQUA peptides provided by the invention is described separately above). Assays may be homogeneous assays or heterogeneous assays. In a homogeneous assay the immunological reaction usually involves a phosphorylation-site specific antibody of the invention), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, a phosphorylation-site specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof that may be useful for carrying out the methods disclosed herein are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of a target ALCL-related signal transduction protein is detectable compared to background.

ALCL-related phosphorylation site-specific antibodies disclosed herein may be conjugated to a solid support suitable for a diagnostic assay (e.g., beads, plates, slides or wells formed from materials such as latex or polystyrene) in accordance with known techniques, such as precipitation. Antibodies, or other target protein or target site-binding reagents, may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Antibodies of the invention may also be optimized for use in a flow cytometry assay to determine the activation/phosphorylation status of a target ALCL-related signal transduction protein in patients before, during, and after treatment with a drug targeted at inhibiting phosphorylation at such a protein at the phosphorylation site disclosed herein. For example, bone marrow cells or peripheral blood cells from patients may be analyzed by flow cytometry for target ALCL-related protein phosphorylation, as well as for markers identifying various hematopoietic cell types. In this manner, activation status of the malignant cells may be specifically characterized. Flow cytometry may be carried out according to standard methods. See, e.g. Chow et al., Cytometry (Communications in Clinical Cytometry) 46: 72-78 (2001). Briefly and by way of example, the following protocol for cytometric analysis may be employed: fixation of the cells with 1% paraformaldehyde for 10 minutes at 37° C. followed by permeabilization in 90% methanol for 30 minutes on ice. Cells may then be stained with the primary antibody (a phospho-specific antibody of the invention), washed and labeled with a fluorescent-labeled secondary antibody. Alternatively, the cells may be stained with a fluorescent-labeled primary antibody. The cells would then be analyzed on a flow cytometer (e.g. a Beckman Coulter EPICS-XL) according to the specific protocols of the instrument used. Such an analysis would identify the presence of activated ALCL-related signal transduction protein(s)elated in the malignant cells and reveal the drug response on the targeted protein.

Alternatively, antibodies of the invention may be employed in immunohistochemical (IHC) staining to detect differences in signal transduction or protein activity using normal and diseased ALCL tissues. IHC may be carried out according to well-known techniques. See, e.g., ANTIBODIES: A LABORATORY MANUAL, supra. Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies of the invention may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., Oncogene 20(16): 1981-89 (2001)). Accordingly, in another embodiment, the invention provides a method for the multiplex detection of ALCL-related protein phosphorylation in a biological sample, the method comprising utilizing at two or more antibodies or AQUA peptides of the invention to detect the presence of two or more phosphorylated ALCL-related signaling proteins enumerated in Column A of Table 1/FIG. 2. In one preferred embodiment, two to five antibodies or AQUA peptides of the invention are employed in the method. In another preferred embodiment, six to ten antibodies or AQUA peptides of the invention are employed, while in another preferred embodiment eleven to twenty are employed.

Antibodies and/or AQUA peptides of the invention may also be employed within a kit that comprises at least one phosphorylation site-specific antibody or AQUA peptide of the invention (which binds to or detects an ALCL-related signal transduction protein disclosed in Table 1), and, optionally, a second antibody conjugated to a detectable group. In some embodies, the kit is suitable for multiplex assays and comprises two or more antibodies or AQUA peptides of the invention, and in some embodiments, comprises two to five, six to ten, or eleven to twenty reagents of the invention. The kit may also include ancillary agents such as buffering agents and protein stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container along with a sheet of printed instructions for carrying out the test.

The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Isolation of Phosphotyrosine-Containing Peptides from Extracts of Karpas-299 and SUDHL-1 Cells and Identification of Novel Phosphorylation Sites In order to discover previously unknown ALCL-related signal transduction protein phosphorylation sites, IAP isolation techniques were employed to identify phosphotyrosine containing peptides in cell extracts from Karpas 299 and SU-DHL-1 cells, which are derived from anaplastic large cell lymphomas (ALCL). See Pulford et al. *Blood* 89: 394-1404 (1997). The majority of ALCL is characterized by the presence of the t(2; 5)(p23; q35) chromosomal translocation that causes the fusion of the nucleophosmin and anaplastic lymphoma kinase genes. See Morris S W, *Science* 263: 1281-1284 (1994). Although the two cell lines are derived from different patients, both express the oncogenic fusion kinase NPM-ALK, which possesses constitutive tyrosine kinase activity and can transform non-malignant cells. See Fujimoto, supra.

Tryptic phosphotyrosine peptides were purified and analyzed from extracts of the two ALCL cell lines as follows. Cells were grown in a 5% $CO_2$ incubator at 37° C. Karpas 299 cells were cultured to a density of $0.5$-$0.8 \times 10^6$ cells/ml in RPMI 1640 medium containing 10% calf serum. SU-DHL-1 cells were cultured the same or to a density of $1.2$-$1.4 \times 10^6$ cells/ml in RPMI 1640 medium containing 10% fetal bovine serum. Cells were washed with PBS at 4° C., resuspended at $1.25 \times 10^8$ cells/ml in lysis buffer (20 mM HEPES pH 8.0, 9 M urea, 1 mM sodium vanadate) and sonicated. In some experiments, the PBS wash step was omitted.

Sonicated cell lysates were cleared by centrifugation at 20,000×g, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and immobilized TLCK-trypsin (Pierce) was added at 1-2.5 ml beads (200 TAME units trypsin/ml) per $10^9$ cells. For digestion with chymotrypsin, endoproteinase GluC, and elastase, lysates were diluted in 20 mM HEPES pH 8.0 to a final concentration of 1 M urea, and GluC (Worthington Biochemicals) or elastase (Roche) was added at 0.5 mg per $10^9$ cells. Chymotrypsin (Worthington Biochemicals) was added at 10 mg per $10^9$ cells. Digestion was performed for 1-2 days at room temperature.

Trifluoroacetic acid (TFA) was added to protein digests to a final concentration of 1%, precipitate was removed by centrifugation, and digests were loaded onto Sep-Pak $C_{18}$ columns (Waters) equilibrated with 0.1% TFA. A column volume of 0.7-1.0 ml was used per $2 \times 10^8$ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to $2 \times 10^8$ cells were dissolved in 1 ml of IAP buffer (20 mM Tris/HCl or 50 mM MOPS pH 7.2, 10 mM sodium phosphate, 50 mM NaCl) and insoluble matter (mainly in peptide fractions III) was removed by centrifugation. IAP was performed on each peptide fraction separately. The phosphotyrosine monoclonal antibody P-Tyr-100 (Cell Signaling Technology, Inc., catalog number 9411) was coupled at 4 mg/ml beads to protein G agarose (Roche). Immobilized antibody (15 μl, 60 μg) was added as 1:1 slurry in IAP buffer to 1 ml of each peptide fraction, and the mixture was incubated overnight at 4° C. with gentle rotation. The immobilized antibody beads were washed three times with 1 ml IAP buffer and twice with 1 ml water, all at 4° C. Peptides were eluted from beads by incubation with 75 μl of 0.1% TFA at room temperature for 10 min.

Analysis by MALDI-TOF Mass Spectrometry.

A thin layer of α-cyano-4-hydroxy-cinnamic acid (ACHA) matrix was applied to a Bruker 384-spot MALDI target by spreading 5 μl of a saturated solution in MeCN/water (2/1, v/v) over an entire row of spots on the target; drying occurred in 2-5 sec. The IAP eluate (10 μl) was loaded onto an 0.2 μl C-18 ZipTip (Millipore), which then was washed with 5% formic acid. Peptide was eluted with 1 μl of 10 mg/ml ACHA in 60% methanol, 5% formic acid onto the MALDI target containing the thin layer of matrix. Samples were analyzed on a Bruker BiFlex III MALDI-TOF instrument in positive ion mode.

Analysis by LC-MS/MS Mass Spectrometry.

40 μl of IAP eluate were purified by 0.2 μl Stage tips. Peptides were eluted from the microcolumns with 1 μl of 40% MeCN, 0.1% TFA (fractions I and II) or 1 μl of 60% MeCN, 0.1% TFA (fraction III) into 7.6 μl of 0.4% acetic acid/0.005% heptafluorobutyric acid. This sample was loaded onto a 10 cm×75 μm PicoFrit capillary column (New Objective) packed with Magic C18 AQ reversed-phase resin (Michrom Bioresources) using a Famos autosampler with an inert sample injection valve (Dionex). The column was then developed with a 45-min linear gradient of acetonitrile delivered at 200 nl/min (Ultimate, Dionex), and tandem mass spectra were collected in a data-dependent manner with an LCQ Deca XP Plus ion trap mass spectrometer essentially as described by Gygi et al., supra.

Database Analysis & Assignments.

MS/MS spectra were evaluated using TurboSequest in the Sequest Browser package (v. 27, rev. 12) supplied as part of BioWorks 3.0 (ThermoFinnigan). Individual MS/MS spectra were extracted from the raw data file using the Sequest Browser program CreateDta, with the following settings: bottom MW, 700; top MW, 4,500; minimum number of ions, 20; minimum TIC, $4 \times 10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the NCBI human protein database (for all other studies) (released on Apr. 29, 2003 and containing 37,490 protein sequences). Cysteine carboxamidomethylation was specified as a static modification, and phosphorylation was allowed as a variable modification on serine, threonine, and tyrosine residues or on tyrosine residues alone. It was determined that restricting phosphorylation to tyrosine residues had little effect on the number of phosphorylation sites assigned.

In proteomics, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al. Mol Cell Proteomics 3: 531-533 (2004), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site. For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted or rejected following a conservative, two-step process. In the first step, a subset of high-scoring sequence assignments was selected by filtering for XCorr values of at least 1.5 for a charge state of +1, 2.2 for +2, and 3.3 for +3, allowing a maximum RSp value of 10. Assignments in this subset were rejected if any of the following criteria were satisfied: (i) the spectrum contained at least one major peak (at least 10% as intense as the most intense ion in the spectrum) that could not be mapped to the assigned sequence as an a, b, or y ion, as an ion arising from neutral-loss of water or ammonia from a b or y ion, or as a multiply protonated ion; (ii) the spectrum did not contain an series of b or y ions equivalent to at least six uninterrupted residues; or (iii) the sequence was not observed at least five times in all the studies we have conducted (except for overlapping sequences due to incomplete proteolysis or use of proteases other than trypsin). In the second step, assignments with below-threshold scores were accepted if the low-scoring spectrum showed a high degree of similarity to a high-scoring spectrum collected in another study, which simulates a true reference library-searching strategy. All spectra supporting the final list of assigned sequences enumerated in Table 1/FIG. 2 herein were reviewed by at least three people to establish their credibility.

EXAMPLE 2

Production of Phospho-specific Polyclonal Antibodies for the Detection of ALCL-Related Protein Phosphorylation Polyclonal antibodies that specifically bind an ALCL-related signal transduction protein only when phosphorylated at the respective phosphorylation site disclosed herein (see Table 1) are produced according to standard methods by first constructing a synthetic peptide antigen comprising the phosphorylation site sequence and then immunizing an animal to raise antibodies against the antigen, as further described below. Production of exemplary polyclonal antibodies is provided below.

A. ALK (Tyrosine 1282).

A 15 amino acid phospho-peptide antigen, RDIYRASy*YRKGGCA (SEQ ID NO: 142) (where y*=phosphotyrosine), that corresponds to the tyrosine 1282 phosphorylation site in human anaplastic lymphoma kinase (ALK) (see Row 143 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific ALK(tyr1282) polyclonal antibodies as described in Immunization/Screening below.

B. IRS-1 (Tyrosine 46).

A 15 amino acid phospho-peptide antigen, GGPARLEy*YENEKKW (SEQ ID NO: 16) (where y*=phosphotyrosine), that corresponds to the tyrosine 46 phosphorylation site in human Insulin Receptor Substrate-1 (IRS-1) (see Row 17 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific IRS-1 (tyr46) polyclonal antibodies as described in Immunization/Screening below.

C. Pyruvate Kinase M (Tyrosine 104).

A 15 amino acid phospho-peptide antigen, FASDPILy*RPVAVAL (SEQ ID NO: 75) (where y*=phosphotyrosine) that corresponds to the tyrosine 104 phosphorylation site in human Pyrvuate Kinase M (PKM) (see Row 76 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals to produce (and subsequently screen) phospho-specific PKM(tyr104) antibodies as described in Immunization/Screening below.

Immunization/Screening.

A synthetic phospho-peptide antigen as described in A-C above is coupled to KLH, and rabbits are injected intradermally (ID) on the back with antigen in complete Freunds adjuvant (500 μg antigen per rabbit). The rabbits are boosted with same antigen in incomplete Freund adjuvant (250 μg antigen per rabbit) every three weeks. After the fifth boost, bleeds are collected. The sera are purified by Protein A-affinity chromatography by standard methods (see ANTIBODIES: A LABORATORY MANUAL, Cold Spring Harbor, supra.). The eluted immunoglobulins are further loaded onto a non-phosphorylated synthetic peptide antigen-resin Knotes column to pull out antibodies that bind the non-phosphorylated form of the phosphorylation site. The flow through fraction is collected and applied onto a phospho-synthetic peptide antigen-resin column to isolate antibodies that bind the phosphorylated form of the site. After washing the column extensively, the bound antibodies (i.e. antibodies that bind a phosphorylated peptide described in A-C above, but do not bind the non-phosphorylated form of the peptide, are eluted and kept in antibody storage buffer.

The isolated antibody is then tested for phospho-specificity using Western blot assay using an appropriate cell line the expresses (or overexpresses) target phospho-protein (i.e. phosphorylated ALK, IRS-1, or PKM), for example, SUDHL-1 and Karpas299 cell lines. Cells are cultured in DMEM supplemented with 10% FCS and 5U/ml IL-3. Before stimulation, the cells are starved in serum-free DMEM medium for 4 hours. The cells are then stimulated ligand (e.g. 50 ng/ml) for 5 minutes. Cell are collected, washed with PBS and directly lysed in cell lysis buffer. The protein concentration of cell lysates are then measured. The loading buffer is added into cell lysate and the mixture is boiled at 10.0° C. for 5 minutes. 20 μl (10 μg protein) of sample is then added onto 7.5% SDS-PAGE gel.

A standard Western blot may be performed according to the Immunoblotting Protocol set out in the CELL SIGNALING TECHNOLOGY, INC. 2003-04 Catalogue, p. 390. The isolated phospho-specific antibody is used at dilution 1:1000. Phosphorylation-site specificity of the antibody will be shown by binding of only the phosphorylated form of the target protein. Isolated phospho-specific polyclonal antibody does not recognize the target protein when not phosphorylated at the appropriate phosphorylation site in the non-stimulated cells (e.g. ALK is not bound when not phosphorylated at tyrosine 1282).

In order to confirm the specificity of the isolated antibody, different cell lysates containing various phosphorylated signal transduction proteins other than the target protein are prepared. The Western blot assay is preformed again using these cell lysates. The phospho-specific polyclonal antibody isolated as described above is used (1:1000 dilution) to test reactivity with the different phosphorylated non-target proteins on Western blot membrane. The phospho-specific antibody does not significantly cross-react with other phosphorylated signal transduction proteins, although occasionally slight binding with a highly-homologous phosphorylation-site on another protein may be observed. In such case the antibody may be further purified using affinity chromatography, or the specific immunoreactivity cloned by rabbit hybridoma technology.

EXAMPLE 3

Production of Phospho-Specific Monoclonal Antibodies for the Detection of ALCL-Related Protein Phosphorylation Monoclonal antibodies that specifically bind an ALCL-related signal transduction protein only when phosphorylated at the respective phosphorylation site disclosed herein (see Table 1) are produced according to standard methods by first constructing a synthetic peptide antigen comprising the phosphorylation site sequence and then immunizing an animal to raise antibodies against the antigen, and harvesting spleen cells from such animals to produce fusion hybridomas, as further described below. Production of exemplary monoclonal antibodies is provided below.

A. ALK (Tyrosine 1078).

A 15 amino acid phospho-peptide antigen, MELQSPEy*KLSKLRT (SEQ ID NO: 138) (where y*=phosphotyrosine) that corresponds to the tyrosine 1078 phosphorylation site in human Anaplastic Lymphoma Kinase (ALK) (see Row 139 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal ALK(tyr1078) antibodies as described in Immunization/Fusion/Screening below.

B. Thioredoxin Reductase 1 (Tyrosine 11).

A 15 amino acid phospho-peptide antigen, PEDLPKSy*DYDLIII (SEQ ID NO: 111) (where y*=phosphotyrosine) that corresponds to the tyrosine 11 phosphorylation site in human Thioredoxin Reductase 1 (TR-1) (see Row 112 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal TR-1 (tyr11) antibodies as described in Immunization/Fusion/Screening below.

C. PABP1 (Tyrosine 54).

A 15 amino acid phospho-peptide antigen, ITRRSLGy*AYVNFQQ (SEQ ID NO: 151) (where y*=phosphotyrosine) that corresponds to the tyrosine 54 phosphorylation site in human PABP 1 (see Row 152 of Table 1), plus cysteine on the C-terminal for coupling, is constructed according to standard synthesis techniques using, e.g., a Rainin/Protein Technologies, Inc., Symphony peptide synthesizer. See ANTIBODIES: A LABORATORY MANUAL, supra.; Merrifield, supra. This peptide is then coupled to KLH and used to immunize animals and harvest spleen cells for generation (and subsequent screening) of phospho-specific monoclonal PABP1 (tyr54) antibodies as described in Immunization/Fusion/Screening below.

Immunization/Fusion/Screening.

A synthetic phospho-peptide antigen as described in A-C above is coupled to KLH, and BALB/C mice are injected intradermally (ID) on the back with antigen in complete Freunds adjuvant (e.g. 50 μg antigen per mouse). The mice are boosted with same antigen in incomplete Freund adjuvant (e.g. 25 μg antigen per mouse) every three weeks. After the fifth boost, the animals are sacrificed and spleens are harvested.

Harvested spleen cells are fused to SP2/0 mouse myeloma fusion partner cells according to the standard protocol of Kohler and Milstein (1975). Colonies originating from the fusion are screened by ELISA for reactivity to the phospho-peptide and non-phospho-peptide forms of the antigen and by Western blot analysis (as described in Example 1 above). Colonies found to be positive by ELISA to the phospho-peptide while negative to the non-phospho-peptide are further characterized by Western blot analysis. Colonies found to be positive by Western blot analysis are subcloned by limited dilution. Mouse ascites are produced from a single clone obtained from subcloning, and tested for phospho-specificity (against the ALK, TR-1, or Beta Actin phospho-peptide antigen, as the case may be) on ELISA. Clones identified as positive on Western blot analysis using cell culture supernatant as having phospho-specificity, as indicated by a strong band in the induced lane and a weak band in the uninduced lane of the blot, are isolated and subcloned as clones producing monoclonal antibodies with the desired specificity.

Ascites fluid from isolated clones may be further tested by Western blot analysis. The ascites fluid should produce similar results on Western blot analysis as observed previously with the cell culture supernatant, indicating phospho-specificity against the phosphorylated target (e.g. ALK phosphorylated at tyrosine 1078).

EXAMPLE 4

Production and Use of AQUA Peptides for the Quantification of ALCL-Related Signaling Protein Phosphorylation Heavy-isotope labeled peptides (AQUA peptides (internal standards)) for the detection and quantification of an ALCL-related signal transduction protein only when phosphorylated at the respective phosphorylation site disclosed herein (see Table 1) are produced according to the standard AQUA methodology (see Gygi et al., Gerber et al., supra.) methods by first constructing a synthetic peptide standard corresponding to the phosphorylation site sequence and incorporating a heavy-isotope label. Subsequently, the MS$^n$ and LC-SRM signature of the peptide standard is validated, and the AQUA peptide is used to quantify native peptide in a biological sample, such as a digested cell extract. Production and use of exemplary AQUA peptides is provided below.

A. Caspase 8 (Tyrosine 334).

An AQUA peptide having a sequence corresponding to the tyrosine 334 phosphorylation site in human Caspase 8, DGQEAPIy*ELTSQFT (y*=phosphotyrosine) (see Row 118 in Table 1 (SEQ ID NO: 117)) but incorporating $^{14}C/^{15}N$-labeled leucine (indicated by bold L) is constructed according to standard synthesis techniques using, e.g., a Rainin/Protein Technologies, Inc., Symphony peptide synthesizer (see Merrifield, supra.) as further described below in Synthesis & MS/MS Signature. The Caspase 8(tyr334) AQUA peptide is then spiked into a biological sample to quantify the amount of phosphorylated Caspase 8(tyr334) in the sample, as further described below in Analysis & Quantification.

B. Intersectin 2 (Tyrosine 858).

An AQUA peptide having a sequence corresponding to the tyrosine 858 phosphorylation site in human Intersectin 2, QPASVTDy*QNVSFSN (y*=phosphotyrosine) (see Row 15 in Table 1 (SEQ ID NO: 14)) but incorporating $^{14}C/^{15}N$-labeled proline (indicated by bold P) is constructed according to standard synthesis techniques using, e.g., a Rainin/Protein Technologies, Inc., Symphony peptide synthesizer (see Merrifield, supra.) as further described below in Synthesis & MS/MS Signature. The Intersectin 2(tyr19) AQUA peptide is then spiked into a biological sample to quantify the amount of phosphorylated Intersectin 2 (tyr19) in the sample, as further described below in Analysis & Quantification.

C. Dicer1 (Tyrosine 654).

An AQUA peptide having a sequence corresponding to the tyrosine 654 phosphorylation site in human Enolase alpha, ELPDGTFy*STLYLPI (y*=phosphotyrosine) (see Row 92 in Table 1 (SEQ ID NO: 91)) but incorporating $^{14}C/^{15}N$-labeled leucine (indicated by bold L) is constructed according to standard synthesis techniques using, e.g., a Rainin/Protein Technologies, Inc., Symphony peptide synthesizer (see Merrifield, supra.) as further described below in Synthesis & MS/MS Signature. The Dicer1 (tyr654) AQUA peptide is then spiked into a biological sample to quantify the amount of phosphorylated Dicer1 (tyr654) in the sample, as further described below in Analysis & Quantification.

D. Glutathione Reductase (Tyrosine 56).

An AQUA peptide having a sequence corresponding to the tyrosine 56 phosphorylation site in human Glutathione Reductase (GR), AGAVASy*DYLVIGG (y*=phosphotyrosine) (see Row 110 in Table 1 (SEQ ID NO: 109)) but incorporating $^{14}C/^{15}N$-labeled leucine (indicated by bold L) is constructed according to standard synthesis techniques using, e.g., a Rainin/Protein Technologies, Inc., Symphony peptide synthesizer (see Merrifield, supra.) as further described below in Synthesis & MS/MS Signature. The GR(tyr56) AQUA peptide is then spiked into a biological sample to quantify the amount of phosphorylated GR(tyr56) in the sample, as further described below in Analysis & Quantification.

Synthesis & MS/MS Spectra.

Fluorenylmethoxycarbonyl (Fmoc)-derivatized amino acid monomers may be obtained from AnaSpec (San Jose, Calif.). Fmoc-derivatized stable-isotope monomers containing one $^{15}N$ and five to nine $^{13}C$ atoms may be obtained from Cambridge Isotope Laboratories (Andover, Mass.). Preloaded Wang resins may be obtained from Applied Biosystems. Synthesis scales may vary from 5 to 25 µmol. Amino acids are activated in situ with 1-H-benzotriazolium, 1-bis (dimethylamino) methylene]-hexafluorophosphate(1-),3-oxide:1-hydroxybenzotriazole hydrate and coupled at a 5-fold molar excess over peptide. Each coupling cycle is followed by capping with acetic anhydride to avoid accumulation of one-residue deletion peptide byproducts. After synthesis peptide-resins are treated with a standard scavenger-containing trifluoroacetic acid (TFA)-water cleavage solution, and the peptides are precipitated by addition to cold ether. Peptides (i.e. a desired AQUA peptide described in A-D above) are purified by reversed-phase C18 HPLC using standard TFA/ acetonitrile gradients and characterized by matrix-assisted laser desorption ionization-time of flight (Biflex III, Bruker Daltonics, Billerica, Mass.) and ion-trap (ThermoFinnigan, LCQ DecaXP) MS.

MS/MS spectra for each AQUA peptide should exhibit a strong y-type ion peak as the most intense fragment ion that is suitable for use in an SRM monitoring/analysis. Reverse-phase microcapillary columns (0.1 Å~150-220 mm) are prepared according to standard methods. An Agilent 1100 liquid chromatograph may be used to develop and deliver a solvent gradient [0.4% acetic acid/0.005% heptafluorobutyric acid (HFBA)/7% methanol and 0.4% acetic acid/0.005% HFBA/ 65% methanol/35% acetonitrile] to the microcapillary column by means of a flow splitter. Samples are then directly loaded onto the microcapillary column by using a FAMOS inert capillary autosampler (LC Packings, San Francisco) after the flow split. Peptides are reconstituted in 6% acetic acid/0.01% TFA before injection.

Analysis & Quantification.

Target protein (e.g. a phosphorylated protein of A-D above) in a biological sample is quantified using a validated AQUA peptide (as described above). The IAP method is then applied to the complex mixture of peptides derived from proteolytic cleavage of crude cell extracts to which the AQUA peptides have been spiked in.

LC-SRM of the entire sample is then carried out. MS/MS may be performed by using a ThermoFinnigan (San Jose, Calif.) mass spectrometer (LCQ DecaXP ion trap or TSQ Quantum triple quadrupole). On the DecaXP, parent ions are isolated at 1.6 m/z width, the ion injection time being limited to 150 ms per microscan, with two microscans per peptide averaged, and with an AGC setting of $1 \times 10^8$; on the Quantum, Q1 is kept at 0.4 and Q3 at 0.8 m/z with a scan time of 200 ms per peptide. On both instruments, analyte and internal standard are analyzed in alternation within a previously known reverse-phase retention window; well-resolved pairs of internal standard and analyte are analyzed in separate retention segments to improve duty cycle. Data are processed by integrating the appropriate peaks in an extracted ion chromatogram (60.15 m/z from the fragment monitored) for the native and internal standard, followed by calculation of the ratio of peak areas multiplied by the absolute amount of internal standard (e.g., 500 fmol).

What is claimed is:

1. An isolated phosphorylation site-specific antibody that specifically binds a human Anaplastic Large Cell Lymphoma (ALCL)-related signaling protein, wherein said signaling protein is prohibitin D, only when said signaling protein is phosphorylated at the tyrosine at position 128, comprised within the phosphorylatable peptide sequence listed in SEQ ID NO: 40, wherein said antibody does not bind said signaling protein when not phosphorylated at said tyrosine.

2. An immortalized cell line producing the antibody of claim 1.

3. The cell line of claim 2, wherein said immortalized cell line is a rabbit hybridoma or a mouse hybridoma.

* * * * *